United States Patent [19]
Chen et al.

[11] Patent Number: 5,905,068
[45] Date of Patent: May 18, 1999

[54] RETROVIRAL PROTEASE INHIBITING COMPOUNDS

[75] Inventors: Xiaoqi Chen, Libertyville; Brian E. Green, Wonder Lake; Dale J. Kempf, Libertyville, all of Ill.; Lin Li, San Diego, Calif.; Daniel W. Norbeck, Crystal Lake; Hing L. Sham, Mundelein, both of Ill.

[73] Assignee: Abbott Laboratories, Abbott Park, Ill.

[21] Appl. No.: 08/718,882

[22] Filed: Sep. 24, 1996

[51] Int. Cl.[6] .......................... A61K 38/05; A61K 39/00
[52] U.S. Cl. ...................... 514/19; 514/885; 424/185.1; 544/242; 548/217; 548/305.1; 548/305.4; 549/546
[58] Field of Search ................ 514/19, 885; 424/185.1; 544/242; 548/217, 305.1, 305.4; 549/546

[56] References Cited

FOREIGN PATENT DOCUMENTS 9414436  7/1994  WIPO .
9418192  8/1994  WIPO .

OTHER PUBLICATIONS

Caplus Abstract No. 118: 192283 (1993) to Kempf et al. EP 486 948 (May, 1992).
Chen, X., et al., "Novel Furofuran Containing HIV Protease Inhibitors", *Book of Abstracts,* 211th ACS National Meeting, New Orleans, LA, (Mar. 24–28, 1996).
Kempf, D. J., et al., "Evaluation of Substituted Benzamides as P2 Ligands for Symmetry–based Inhibitors of HIV Protease", *Bioorganic & Medicinal Chemistry Letters,* 5(22):2725–2728 (1995).
Kempf, D. J., et al., "HIV Protease Inhibitors", *Current Pharmaceutical Design,* 2:225–246 (1996).

*Primary Examiner*—Cecilia J. Tsang
*Assistant Examiner*—Bennett Celsa
*Attorney, Agent, or Firm*—Steven R. Crowley; Dianne Casuto

[57] ABSTRACT

A compound of the formula:

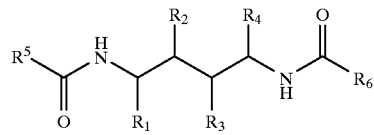

is disclosed as a retroviral protease inhibitor compound. Also disclosed are methods and compositions for inhibiting an HIV infection.

13 Claims, No Drawings

RETROVIRAL PROTEASE INHIBITING COMPOUNDS

TECHNICAL FIELD

The present invention relates to novel compounds, compositions and methods for inhibiting retroviral proteases and in particular for inhibiting human immunodeficiency virus (HIV) protease. The present invention also relates to novel compositions and methods for inhibiting a retroviral infection and in particular an HIV infection, and to processes for making the compounds and synthetic intermediates employed in the processes.

BACKGROUND OF THE INVENTION

Retroviruses are those viruses which utilize a ribonucleic acid (RNA) intermediate and an RNA-dependent deoxyribonucleic acid (DNA) polymerase, reverse transcriptase, during their life cycle. Retroviruses include, but are not limited to, the RNA viruses of the Retroviridae family, and also the DNA viruses of the Hepadnavirus and Caulimovirus families. Retroviruses cause a variety of disease states in man, animals and plants. Some of the more important retroviruses from a pathological standpoint include human immunodeficiency viruses (HIV-1 and HIV-2), which cause acquired immune deficiency syndrome (AIDS) in man, hepatitis B virus, which causes hepatitis and hepatic carcinomas in man, human T-cell lymphotrophic viruses I, II, IV and V, which cause human acute cell leukemia, and bovine and feline leukemia viruses which cause leukemia in domestic animals.

Proteases are enzymes which cleave proteins at specific peptide bonds. Many biological functions are controlled or mediated by proteases and their complementary protease inhibitors. For example, the protease renin cleaves the peptide angiotensinogen to produce the peptide angiotensin I. Angiotensin I is further cleaved by the protease angiotensin converting enzyme (ACE) to form the hypotensive peptide angiotensin II. Inhibitors of renin and ACE are known to reduce high blood pressure in vivo. An inhibitor of a retroviral protease will provide a therapeutic agent for diseases caused by the retrovirus.

The genomes of retroviruses encode a protease that is responsible for the proteolytic processing of one or more polyprotein precursors such as the pol and gag gene products. See Wellink, Arch. Virol. 98 1 (1988). Retroviral proteases most commonly process the gag precursor into core proteins, and also process the pol precursor into reverse transciptase and retroviral protease. In addition, retroviral proteases are sequence specific. See Pearl, Nature 328 482 (1987).

The correct processing of the precursor polyproteins by the retroviral protease is necessary for the assembly of infectious virions. It has been shown that in vitro muitagenesis that produces protease-defective virus leads to the production of immature core forms which lack infectivity. See Crawford, J. Virol. 53 899 (1985); Katoh, et al., Virology 145 280 (1985). Therefore, retroviral protease inhibition provides an attractive target for antiviral therapy. See Mitsuya, Nature 325 775 (1987).

Current treatments for viral diseases usually involve administration of compounds that inhibit viral DNA synthesis. Current treatments for AIDS involve administration of compounds such as 3'-azido-3'-deoxythymidine (AZT), 2',3'-dideoxycytidine (DDC) and 2',3'-dideoxyinosine (DDI) and compounds which treat the opportunistic infections caused by the immunosuppression resulting from HIV infection. None of the current AIDS treatments have proven to be totally effective in treating and/or reversing the disease. In addition, many of the compounds currently used to treat AIDS cause adverse side effects including low platelet count, renal toxicity and bone marrow cytopenia. Recently the HIV protease inhibitors ritonavir, indinavir and saquinavir were approved in the U.S. for treatment of HIV infections. However, there is a continuing need for improved HIV protease inhibitors.

DISCLOSURE OF THE INVENTION

In accordance with the present invention and in a first embodiment, there is a compound of the formula I:

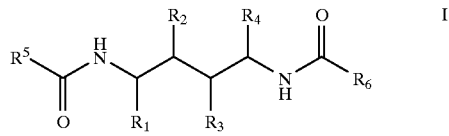

or a pharmaceutically acceptable salt, ester or prodrug thereof wherein $R_1$ and $R_4$ are independently selected from the group consisting of loweralkyl, cycloalkylalkyl and arylalkyl;

$R_2$ is —H and $R_3$ is —OH or $R_2$ is —OH and $R_3$ is —H;

one of $R_5$ and $R_6$ is —$L_1L_2$ wherein $L_1$ is —O— or —$NR_{101}$— wherein $R_{101}$ is hydrogen or loweralkyl and $L_2$ is a heterocycle having one oxygen atom or a bicycloheterocycle having at least one oxygen atom in each cyclic ring and wherein the heterocycle or bicycloheterocycle is unsubstituted or substituted with loweraLkyl or cycloalkyl; and the other of $R_5$ and $R_6$ is 1) —$L_1L_2$ wherein $L_1$ and $L_2$ are independently as defined above,
2) —$L_3L_4R_7$ wherein
 $L_3$ is -alkylenyl-, -alkenylenyl-, or —$OCH_2$—;
 $L_4$ is absent or is selected from the group consisting of —O—, —S—, —S(O)—, —$S(O)_2$—, and —$N(R_8)$— wherein
  $R_8$ is —H, loweralkyl, cycloaLlyl or cycloalkylalkyl; and
  $R_7$ is aryl or a heterocycle,
3) aryl or
4) an N-protecting group
with the proviso that when $R_5$ is —O— bis-tetrahydrofuran, $R_6$ is other than —O— bis-tetrahydrofuran.

Preferred compounds of the invention are compounds of the formula I wherein $R_1$ and $R_4$ are independently selected from the group consisting of (i) benzyl unsubstituted or substituted with one, two or three of —OH or —$C_1$-$C_3$-alkoxy and (ii) —$C_5$-$C_7$-cycloalkylmethyl unsubstituted or substituted with one, two or three of —OH or —$C_1$-$C_3$-alkoxy, and $R_2$, $R_3$, $R_5$, and $R_6$ are as defined above.

More preferred compounds of the invention are compounds of the formula I wherein $R_1$ and $R_4$ are unsubstituted benzyl, and $R_2$, $R_3$, $R_5$ and $R_6$ are as defined above.

Even more preferred compounds of the invention are compounds of the formula I wherein $R_1$ and $R_4$ are unsubstituted benzyl, $R_2$ and $R_3$ are as defined above, one of R₅ and R₆ is —L₁L₂ wherein L₁ is —O— and L₂ is -bis-tetrahydrofuran and the other of R₅ and R₆ is —L₃L₄R₇ wherein L₃ is -alkylenyl-, L₄ is —O— and R₇ is
- a) phenyl substituted with one to five substituents independently selected from the group consisting of i) loweralkyl, ii) hydroxy, iii) amino, iv) hydroxyaLkyl, and v) halogen or
- b) a heterocycle selected from the group consisting of i) pyridyl, ii) pyrimidinyl, iii) benzimidazolyl, iv) benzoxazolyl, and v) benzimidazolinonyl wherein the heterocycle is unsubstituted or substituted with one, two or three substituents independently selected from the group consisting of aa) loweralkyl, bb) hydroxy, cc) amino, and dd) halogen.

Even more preferred compounds of the invention are compounds of the formula I wherein $R_1$ and $R_4$ are unsubstituted benzyl, $R_2$ and $R_3$ are as defined above, one of R₅ and R₆ is —L₁L₂ wherein L₁ is —O— and L₂ is -bis-tetrahydrofuran and the other of R₅ and R₆ is —L₃L₄R₇ wherein L₃ is -alkylenyl-, L₄ is —O— and R₇ is
- a) phenyl substituted with one or two substituents independently selected from the group consisting of methyl, ethyl and propyl and optionally further substituted with loweralkyl, amino, halogen, hydroxy or hydroxymethyl or
- b) a heterocycle selected from the group consisting of i) pyridyl, ii) pyrimidinyl, iii) benzimidazolyl, iv) benzoxazolyl, and v) benzimidazolinonyl wherein the heterocycle is unsubstituted or substituted with two methyl substituents and optionally with a third substituent selected from the group consisting of aa) loweralkyl, bb) hydroxy, cc) amino, and dd) halogen.

Most preferred compounds of formula I are (2S,3S,5S)-5-(2,6-Dimethyl-4-amino-phenoxyacetyl) amino-2-((3R,3aS,6aR)-bis-tetrahydrofuran-3-yl-oxycarbonyl)amino-1,6-diphenyl-3-hydroxyhexane;

(2S,3S,5S)-5-(2,6-Dimethyl-4-amino-phenoxyacetyl) amino-2-((3S,3aR,6aS)-bis-tetrahydrofuran-3-yl-oxycarbonyl)amino-1,6-diphenyl-3-hydroxyhexane;

(2S,3S,5S)-2-(2,6-Dimethyl-4-amino-phenoxyacetyl) amino-5-((3R,3aS,6aR)-bis-tetrahydrofuran-3-yl-oxycarbonyl)amino-1,6-diphenyl-3-hydroxyhexane;

(2S,3S,5S)-5-(2,4,6-Trimethyl-3-amino-phenoxyacetyl) amino-2-((3R,3aS,6aR)-bis-tetrahydrofuran-3-yl-oxycarbonyl)amino-1,6-diphenyl-3-hydroxyhexane;

(2S,3S,5S)-5-(2,6-Dimethyl-phenoxyacetyl)amino-2-((3R,3aS,6aR)-bis-tetrahydrofuran-3-yl-oxycarbonyl) amino-1 ,6-diphenyl-3-hydroxyhexane;

(2S,3S,5S)-2-(2,6-Dimethyl-phenoxyacetyl)amino-5-((3R,3aS,6aR)-bis-tetrahydrofuran-3-yl-oxycarbonyl) amino-1,6-diphenyl-3-hydroxyhexane;

(2S,3S,5S)-5-(2-Hydroxymethyl-6-methyl-phenoxyacetyl)amino-2-((3R,3aS,6aR)-bis-tetrahydrofuran-3-yl-oxycarbonyl)amino-1,6-diphenyl-3-hydroxyhexane;

(2S,3S,5S)-5-(4,6-Dimethyl-pyrimidinyl-5-oxyacetyl) amino-2-((3R,3aS,6aR)-bis-tetrahydrofuran-3-yl-oxycarbonyl)amino-1,6-diphenyl-3-hydroxyhexane;

(2S,3S,5S)-5-(N-(2,6-Dimethyl-phenyl)aminoacetyl) amino-2-((3R,3aS,6aR)-bis-tetrahydrofuran-3-yl-oxycarbonyl)amino-1,6-diphenyl-3-hydroxyhexane;

(2S,3S,5S)-5-(2,6-Dimethyl-pyridin-3-yl-oxyacetyl) amino-2-((3R,3aS,6aR)-bis-tetrahydrofuran-3-yl-oxycarbonyl)amino-1,6-diphenyl-3-hydroxyhexane;

(2S,3S,5S)-5-(2,4,6-Trimethyl-phenoxyacetyl)amino-2-((3R,3aS,6aR)-bis-tetrahydrofuran-3-yl-oxycarbonyl) amino-1,6-diphenyl-3-hydroxyhexane;

(2S,3S,5S)-5-(2-Methoxy-6-methylphenoxyacetyl) amino-2-((3R,3aS,6aR)-bis-tetrahydrofuran-3-yl-oxycarbonyl)amino-1,6-diphenyl-3-hydroxyhexane;

(2S,3S,5S)-5-(N-(2,6-Dimethyl-phenyl)-N-methyl-aminoacetyl)amino-2-((3R,3aS,6aR)-bis-tetrahydrofuran-3-yl-oxycarbonyl)amino-1,6-diphenyl-3-hydroxyhexane;

(2S,3S,5S)-5-(2,6-Dimethyl-4-fluoro-phenoxyacetyl) amino-2-((3R,3aS,6aR)-bis-tetrahydrofuran-3-yl-oxycarbonyl)amino-1,6-diphenyl-3-hydroxyhexane;

(2S,3S,5S)-5-(2,6-Dimethyl-4-fluoro-phenoxyacetyl) amino-2-((3R,3aS,6aR)-bis-tetrahydrofuran-3-yl-oxycarbonyl)amino-1,6-diphenyl-3-hydroxyhexane;

(2S,3S,5S)-5-(2,6-Dimethyl-3-amino-phenoxyacetyl) amino-2-((3R,3aS,6aR)-bis-tetrahydrofuran-3-yl-oxycarbonyl)amino-1,6-diphenyl-3-hydroxyhexane;

(2S,3S,5S)-5-(2,6-Dimethyl-4-aminoacetyl)amino-2-((3R,3aS,6aR)-bis-tetrahydrofuran-3-yl-oxycarbonyl) amino-1,6-diphenyl-3-hydroxyhexane;

(2S,3S,5S)-5-(2,6-Dimethyl-4-amino-phensulfonylacetyl)amino-2-((3R,3aS,6aR)-bis-tetrahydrofuran-3-yl-oxycarbonyl)amino-1,6-diphenyl-3-hydroxyhexane;

(2S,3S,5S)-5-(2,6-Dimethyl-4-amino-phenylsulfinylacetyl)amino-2-((3R,3aS,6aR)-bis-tetrahydrofuran-3-yl-oxycarbonyl)amino-1,6-diphenyl-3-hydroxyhexane;

(2S,3S,5S)-2,5-Di-((3R,3aS,6aR)-bis-Tetrahydrofuran-3-yl-oxycarbonyl)amino-1,6-diphenyl-3-hydroxyhexane;

(2S,3S,5S)-2,5-Di-((3S,3aR,6aS)-bis-Tetrahydrofuran-3-yl-oxycarbonyl)amino-1,6-diphenyl-3-hydroxyhexane;

(2S,3S,5S)-2-((3R,3aS,6aR)-bis-Tetrahydrofuran-3-yl-oxycarbonyl)amino-5-((3S,3aR,6aS)-bis-Tetrahydrofuran-3-yl-oxycarbonyl)amino-1,6-diphenyl-3-hydroxyhexane;

(2S,3S,5S)-2-((3S,3aR,6aS)-bis-Tetrahydrofuran-3-yl-oxycarbonyl)amino-5-((3R,3aS,6aR)-bis-tetrahydrofuran-3-yl-oxycarbonyl)amino-1,6-diphenyl-3-hydroxyhexane;

(2S,3S,5S)-5-(4,6-Dimethyl-benzimidazol-5-yloxy-acetyl)amino-2-((3R,3aS,6aR)-bis-tetrahydrofuran-3-yl-oxycarbonyl)amino-1,6-diphenyl-3-hydroxyhexane;

(2S,3S,5S)-5-(4,6-Dimethyl-benzimidazolinon-5-yloxy-acetyl)amino-2-((3R,3aS,6aR)-bis-tetrahydrofuran-3-yl-oxycarbonyl)amino-1,6-diphenyl-3-hydroxyhexane;

(2S,3S,5S)-5-(4,6-Dimethyl-benzoxazol-5-yloxy-acetyl) amino-2-((3R,3aS,6aR)-bis-tetrahydrofuran-3-yl-oxycarbonyl)amino-1,6-diphenyl-3-hydroxyhexane;

(2S,3S,5S)-2-((5-Thiazolyl)methoxycarbonyl)amino-5-((3R,3aS,6aR), (3S,3aR,6aS)-bis-tetrahydrofuran-3-yl-oxycarbonyl)amino-1,6-diphenyl-3-hydroxyhexane;

(2S,3S,5S)-2-((5-Thiazolyl)methoxycarbonyl)amino-5-((3S,3aR,6aS)-bis-tetrahydrofuran-3-yl-oxycarbonyl) amino-1,6-diphenyl-3-hydroxyhexane;

(2S,3S,5S)-5-((5-Thiazolyl)methoxycarbonyl)amino-2-((3R,3aS,6aR), (3S,3aR,6aS)-bis-tetrahydrofuran-3-yl-oxycarbonyl)amino-1,6-diphenyl-3-hydroxyhexane;

(2S,3S,5S)-2,5-((3R,3aS,6aR)-bis-Tetrahydrofuran-3-yloxycarbonyl)amino-1,6-diphenyl-3-hydroxyhexane;

(2S,3S,5S)-5-(4-Hydroxy-benzoyl)amino-2-((3S,3aR,6aS)-bis-tetrahydrofuran-3-yl-oxycarbonyl)amino-1,6-diphenyl-3-hydroxyhexane;

(2S,3S,5S)-5-(4-Acetoxy-benzoyl)amino-2-((3R,3aS, 6aR)-bis-tetrahydrofuran-3-yl-oxycarbonyl)amino-1, 6-diphenyl-3-hydroxyhexane;
(2S,3S,5S)-5-(4-Hydroxy-benzoyl)amino-2-((3R,3aS, 6aR)-bis-tetrahydrofuran-3-yl-oxycarbonyl)amino-1, 6-diphenyl-3-hydroxyhexane;
(2S,3S,5S)-5-(4-Acetoxy-benzoyl)amino-2-((3S,3aR, 6aS)-bis-tetrahydrofuran-3-yl-oxycarbonyl)amino-1,6-diphenyl-3-hydroxyhexane;
(2S,3S,5S)-5-(2-Chloro-4-hydroxy-benzoyl)amino-2-((3R,3aS,6aR)-bis-tetrahydrofuran-3-yl-oxycarbonyl) amino-1,6-diphenyl-3-hydroxyhexane;
(2S,3S,5S)-5-(3-Hydroxy-benzoyl)amino-2-((3S,3aR, 6aS)-bis-tetrahydrofuran-3-yl-oxycarbonyl)amino-1,6-diphenyl-3-hydroxyhexane;
(2S,3S,5S)-2-(3-Hydroxy-2-methyl-benzoyl)amino-5-((3R,3aS,6aR)-bis-tetrahydrofuran-3-yl-oxycarbonyl) amino-1,6-diphenyl-3-hydroxyhexane;
(2S,3S,5S)-2-(3-Hydroxy-2-methyl-benzoyl)amino-5-((3S,3aR,6aS)-bis-tetrahydrofuran-3-yl-oxycarbonyl) amino-1,6-diphenyl-3-hydroxyhexane;
(2S,3S,5S)-2-(3-Amino-2-methyl-benzoyl)amino-5-((3R,3aS,6aR)-bis-tetrahydrofuran-3-yl-oxycarbonyl) amino-1,6-diphenyl-3-hydroxyhexane;
(2S,3S,5S)-2-(3-Amino-6-chloro-benzoyl)amino-5-((3R,3aS,6aR)-bis-tetrahydrofuran-3-yl-oxycarbonyl) amino-1,6-diphenyl-3-hydroxyhexane;
(2S,3S,5S)-2-(3-Amino-6-chloro-benzoyl)amino-5-((3S,3aR,6aS)-bis-tetrahydrofuran-3-yl-oxycarbonyl) amino-1,6-diphenyl-3-hydroxyhexane;
(2S,3S,5S)-2-(4-Hydroxy-benzoyl)amino-5-((3R,3aS, 6aR)-bis-tetrahydrofuran-3-yl-oxycarbonyl)amino-1, 6-diphenyl-3-hydroxyhexane;
(2S,3S,5S)-2-(4-Hydroxy-benzoyl)amino-5-((3S,3aR, 6aS)-bis-tetrahydrofuran-3-yl-oxycarbonyl)amino-1,6-diphenyl-3-hydroxyhexane;
(2S,3S,5S)-2-(3-Hydroxy-benzoyl)amino-5-((3R,3aS, 6aR)-bis-tetrahydrofuran-3-yl-oxycarbonyl)amino-1, 6-diphenyl-3-hydroxyhexane;
(2S,3S,5S)-2-(3-Hydroxy-benzoyl)amino-5-((3S,3aR, 6aS)-bis-tetrahydrofuran-3-yl-oxycarbonyl)amino-1,6-diphenyl-3-hydroxyhexane;
(2S,3S,5S)-2-(Benzoyl)amino-5-((3R,3aS,6aR)-bis-tetrahydrofuran-3-yl-oxycarbonyl)amino-1,6-diphenyl-3-hydroxyhexane;
(2S,3S,5S)-2-(Benzoyl)amino-5-((3S,3aR,6aS)-bis-tetrahydrofuran-3-yl-oxycarbonyl)amino-1,6-diphenyl-3-hydroxyhexane;
(2S,3S,5S)-2-(4-Acetoxy-benzoyl)amino-5-((3R,3aS, 6aR)-bis-tetrahydrofuran-3-yl-oxycarbonyl)amino-1, 6-diphenyl-3-hydroxyhexane;
(2S,3S,5S)-2-(4-Amino-2-chloro-benzoyl)amino-5-((3R, 3aS,6aR)-bis-tetrahydrofuran-3-yl-oxycarbonyl) amino-1,6-diphenyl-3-hydroxyhexane;
(2S,3S,5S)-2-(4-Amino-2-chloro-benzoyl)amino-5-((3S, 3aR,6aS)-bis-tetrahydrofuran-3-yl-oxycarbonyl) amino-1,6-diphenyl-3-hydroxyhexane;
(2S,3S,5S)-2-(3-Methoxy-4-hydroxy-benzoyl)amino-5-((3R,3aS,6aR)-bis-tetrahydrofuran-3-yl-oxycarbonyl) amino-1,6-diphenyl-3-hydroxyhexane; and
(2S,3S,5S)-5-(2,6-Dimethyl-3-hydroxy-phenoxyacetyl) amino-2-((3R,3aS, 6aR)-bis-tetrahydrofuran-3-yl-oxycarbonyl)amino-1,6-diphenyl-3-hydroxyhexane.

Most highly preferred compounds of the formula I are
(2S,3S,5S)-5-(2,6-Dimethyl-3-amino-phenoxyacetyl) amino-2-((3R,3aS, 6aR)-bis-tetrahydrofuran-3-yl-oxycarbonyl)amino-1,6-diphenyl-3-hydroxyhexane and
(2S,3S,5S)-5-(2,6-Dimethyl-3-hydroxy-phenoxyacetyl) amino-2-((3R,3aS, 6aR)-bis-tetrahydrofuran-3-yl-oxycarbonyl)amino-1,6-diphenyl-3-hydroxyhexane or a pharmaceutically acceptable salt, ester or prodrug thereof.

In a second embodiment of the invention, there is a compound of the formula II:

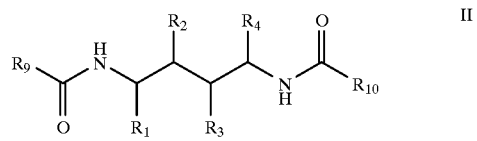

or a pharmaceutically acceptable salt, ester or prodrug thereof wherein $R_1$ and $R_4$ are independently selected from the group consisting of loweralkyl, cycloalkylalkyl and arylalkyl;

$R_2$ is —H and $R_3$ is —OH or $R_2$ is —OH and $R_3$ is —H;

one of $R_9$ and $R_{10}$ is —$L_1L_2$ wherein $L_1$ is —O— or —$NR_{101}$— wherein $R_{101}$ is hydrogen or loweralkyl and $L_2$ is a heterocycle having one oxygen atom or a bicycloheterocycle having at least one oxygen atom in each cyclic ring and wherein the heterocycle or bicycloheterocycle is unsubstituted or substituted with loweralkyl or cycloalkyl; and the other of $R_9$ and $R_{10}$ is

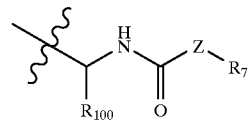

wherein $R_{100}$ is loweralkyl,

Z is —$L_5L_6$ wherein
 $L_5$ is —O— or —$N(R_8)$— wherein $R_8$ is —H, loweralkyl, cycloalkyl or cycloalkylalkyl, and
 $L_6$ is alkylenyl; and $R_7$ is aryl or a heterocycle.

Preferred compounds of the invention are compounds of the formula II wherein $R_1$ and $R_4$ are independently selected from the group consisting of (i) benzyl unsubstituted or substituted with one, two or three of —OH or —$C_1$–$C_3$-alkoxy and (ii) —$C_5$–$C_7$-cycloalkylmethyl unsubstituted or substituted with one, two or three of —OH or —$C_1$–$C_3$-alkoxy, and $R_2$, $R_3$, $R_9$, and $R_{10}$ are as defined above.

More preferred compounds of the invention are compounds of the formula II wherein $R_1$ and $R_4$ are unsubstituted benzyl, and $R_2$, $R_3$, $R_9$, and $R_{10}$ are as defined above.

Even more preferred compounds of the invention are compounds of the formula II wherein $R_1$ and $R_4$ are unsubstituted benzyl, $R_2$ and $R_3$ are as defined above, one of $R_9$ and $R_{10}$ is —$L_1L_2$ wherein $L_1$ is —O— and $L_2$ is -bis-tetrahydrofuran and the other of $R_9$ and $R_{10}$ is

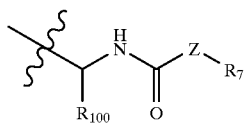

wherein
$R_{100}$ is methyl, ethyl, propyl, isopropyl, isobutyl, or t-butyl,
Z is —$L_5L_6$ wherein $L_5$ is —O— or —N($R_8$)— wherein $R_8$ is as defined above and $L_6$ is -alkylenyl-, and
$R_7$ is a 5-membered heterocycle having one or two heteroatoms independently selected from the group consisting of —S—, —N—, and —O—, wherein the heterocycle is unsubstituted or substituted with loweralkyl or hydroxyalkyl.

Most preferred compounds of the formula II are
(2S,3S,5S)-5-(N-(N-((N-Methyl-N-((2-isopropyl-4-thiazolyl)methyl)amino)carbonyl)-L-valinyl)amino)-2-((3R,3aS,6aR), (3S,3aR,6aS)-bis-tetrahydrofuran-3-yl-oxycarbonyl)amino-1,6-diphenyl-3-hydroxyhexane;

(2S,3S,5S)-5-(N-(N-((2-Isopropyl-4-thiazolyl)methyl) oxycarbonyl)-D-valinyl)amino)-2-((3R,3aS,6aR), (3S,3aR,6aS)-bis-tetrahydrofuran-3-yl-oxycarbonyl) amino-1,6-diphenyl-3-hydroxyhexane;

(2S,3S,5S)-5-(N-(N-((2-Isopropyl-4-thiazolyl)methyl) oxycarbonyl)-L-valinyl)amino)-2-((3R,3aS,6aR), (3S,3aR,6aS)-bis-tetrahydrofuran-3-yl-oxycarbonyl) amino-1,6-diphenyl-3-hydroxyhexane;

(2S,3S,5S)-5-(N-(N-((N-Methyl-N-((2-isopropyl-4-thiazolyl)methyl)amino)carbonyl)-D-valinyl)amino)-2-((3R,3aS,6aR), (3S,3aR,6aS)-bis-tetrahydrofuran-3-yl-oxycarbonyl)amino-1,6-diphenyl-3-hydroxyhexane;

(2S,3S,5S)-5-(N-(N-((5-Thiazolyl)methoxycarbonyl)-L-valinyl)amino)-2-((3R,3aS,6aR)-bis-tetrahydrofuran-3-yl-oxycarbonyl)amino-1,6-diphenyl-3-hydroxyhexane;

(2S,3S,5S)-5-(N-(N-((5-Thiazolyl)methoxycarbonyl)-D-valinyl)amino)-2-((3R,3aS,6aR)-bis-tetrahydrofuran-3-yl-oxycarbonyl)amino-1,6-diphenyl-3-hydroxyhexane;

(2S,3S,5S)-5-(N-(N-((N-Methyl-N-((5-thiazolyl)methyl) amino)carbonyl)-D-valinyl)amino)-2-((3R,3aS,6aR)-bis-tetrahydrofuran-3-yl-oxycarbonyl)amino-1,6-diphenyl-3-hydroxyhexane;

(2S,3S,5S)-5-(N-(N-((N-Methyl-N-((5-thiazolyl)methyl) amino)carbonyl)-L-valinyl)amino)-2-((3R,3aS,6aR)-bis-tetrahydrofuran-3-yl-oxycarbonyl)amino-1,6-diphenyl-3-hydroxyhexane;

(2S,3S,5S)-2-(N-(N-((N-Methyl-N-((2-isopropyl-4-thiazolyl)methyl)amino)carbonyl)-L-valinyl)amino)-5-((3R,3aS,6aR)-bis-tetrahydrofuran-3-yl-oxycarbonyl) amino-1,6-diphenyl-3-hydroxyhexane;

(2S,3S,5S)-5-(N-(N-((N-Methyl-N-((2-methyl-4-thiazolyl)methyl)amino)carbonyl)-L-valinyl)amino)-2-((3S,3aR,6aS)-bis-tetrahydrofuran-3-yl-oxycarbonyl) amino-1,6-diphenyl-3-hydroxyhexane;

(2S,3S,5S)-5-(N-(N-((N-Methyl-N-((2-isopropyl-4-thiazolyl)methyl)amino)carbonyl)-L-valinyl)amino)-2-((3S,3aR,6aS)-bis-tetrahydrofuran-3-yl-oxycarbonyl) amino-1,6-diphenyl-3-hydroxyhexane;

(2S,3S,5S)-5-(N-(N-((N-Methyl-N-((2-methyl-4-thiazolyl)methyl)amino)carbonyl)-L-valinyl)amino)-2-

((3R,3aS,6aR)-bis-tetrahydrofuran-3-yl-oxycarbonyl) amino-1,6-diphenyl-3-hydroxyhexane;

(2S,3S,5S)-5-(N-(N-((N-Methyl-N-((2-isopropyl-4-thiazolyl)methyl)amino)carbonyl)-L-valinyl)amino)-2-(3S-tetrahydrofuran-3-yl-oxycarbonyl)amino-1,6-diphenyl-3-hydroxyhexane;

(2S,3S,5S)-5-(N-(N-((N-Methyl-N-((2-isopropyl-4-thiazolyl)methyl)amino)carbonyl)-D-valinyl)amino)-2-((3R,3aS,6aR)-bis-tetrahydrofuran-3-yl-oxycarbonyl)amino-1,6-diphenyl-3-hydroxyhexane;

(2S,3S,5S)-5-(N-(N-((N-Methyl-N-((2-methyl-4-thiazolyl)methyl)amino)carbonyl)-L-valinyl)amino)-2-((3R,3aS,6aR),(3S,3aR,6aS)-bis-tetrahydrofaran-3-yl-oxycarbonyl)amino-1,6-diphenyl-3-hydroxyhexane.

A most highly preferred compound of the formula II is
(2S,3S,5S)-2-(N-(N-((N-Methyl-N-((2-isopropyl-4-thiazolyl)methyl)amino)carbonyl)-L-valinyl)amino)-5-((3R,3aS,6aR)-bis-tetrahydrofuran-3-yl-oxycarbonyl)amino-1,6-diphenyl-3-hydroxyhexane;

In a third embodiment of the invention, there is a compound of the formula III:

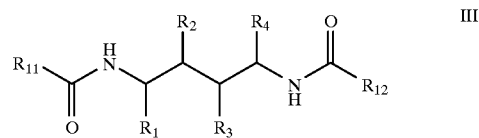

or a pharmaceutically acceptable salt, ester or prodrug thereof wherein
$R_1$ and $R_4$ are independently selected from the group consisting of loweralkyl, cycloalkylalkyl and arylalkyl;
$R_2$ is —H and $R_3$ is —OH or $R_2$ is —OH and $R_3$ is —H; and
one of $R_{11}$ and $R_{12}$ is —$L_7L_8$ wherein $L_7$ is absent or —O— and $L_8$ is a 5- or 6-membered heterocycle having one heteroatom which is —S—, —S(O)— or —S(O)$_2$—, and wherein the heterocycle is unsubstituted or substituted with one or two independently selected loweralkyl groups and
the other of $R_{11}$ and $R_{12}$ is
1) —$L_3L_4R_7$ wherein
$L_3$ is -alkylenyl-, -alkenylenyl-, or —OCH$_2$—;
$L_4$ is absent or is selected from the group consisting of —O—, —S—, —S(O)—, —S(O)$_2$—, and —N($R_8$)— wherein
$R_8$ is —H, loweralkyl, cycloaLkyl or cycloalkylalkyl; and
$R_7$ is aryl or a heterocycle, or
2) an N-protecting group.

Preferred compounds of the invention are compounds of the formula III wherein
$R_1$ and $R_4$ are independently selected from the group consisting of (i) benzyl unsubstituted or substituted with one, two or three of —OH or —$C_1$–$C_3$-alkoxy and (ii) —$C_5$–$C_7$-cycloalkylmethyl unsubstituted or substituted with one, two or three of —OH or —$C_1$–$C_3$-alkoxy, and
$R_2$, $R_3$, $R_{11}$, and $R_{12}$ are as defined above.

More preferred compounds of the invention are compounds of the formula III wherein
$R_1$ and $R_4$ are unsubstituted benzyl, and
$R_2$, $R_3$, $R_{11}$, and $R_{12}$ are as defined above.

Even more preferred compounds of the invention are compounds of the formula III wherein $R_1$ and $R_4$ are unsubstituted benzyl, $R_2$ and $R_3$ are as defined above, one of $R_{11}$ and $R_{12}$ is —$L_7L_8$ wherein —$L_7L_8$ is as defined above, and the other of $R_{11}$ and $R_{12}$ is —$L_3L_4R_7$ wherein $L_3$ is -alkylenyl-, $L_4$ is —O— and $R_7$ is phenyl substituted one to five substituents independently selected from the group consisting of i) loweralkyl, ii) hydroxy, iii) amino, iv) hydroxyalkyl, and v) halogen.

Most preferred compounds of formula III are (2S,3S,5S)-2-(2,6-Dimethylphenoxyacetyl)amino-5-(3 (R,S)-2(R,S)-isopropyl-tetrahydrothienyloxycarbonyl) amino-1,6-diphenyl-3-hydroxyhexane;

(2S,3S,5S)-2-(2,6-Dimethylphenoxyacetyl)amino-5-(1,1-dioxo-3(R,S)-2(R,S)-isopropyl-tetrahydrothienyloxycarbonyl)amino-1,6-diphenyl-3-hydroxyhexane;

(2S,3S,5S)-2-(2,6-Dimethylphenoxyacetyl)amino-5-(1,1-dioxo-3(R,S)-tetrahydrothiopyranyloxycarbonyl) amino-1,6-diphenyl-3-hydroxyhexane;

(2S,3S,5S)-2-(2,6-Dimethylphenoxyacetyl)amino-5-(3 (R,S)-tetrahydrothienyloxycarbonyl)amino-1,6-diphenyl-3-hydroxyhexane;

(2S,3S,5S)-2-(2,6-Dimethylphenoxyacetyl)amino-5-(3 (R,S)-tetrahydrothiopyranyloxycarbonyl)amino-1,6-diphenyl-3-hydroxyhexane;

(2S,3S,5S)-2-(2,6-Dimethylphenoxyacetyl)amino-5-(3R-2,2-dimethyltetrahydrothienyloxycarbonyl)amino-1,6-diphenyl-3-hydroxyhexane;

(2S,3S,5S)-2-(2,6-Dimethylphenoxyacetyl)amino-5-(3R-2,2-dimethyl-1,1-dioxytetrahydrothienyloxycarbonyl) amino-1,6-diphenyl-3-hydroxyhexane.

A most highly preferred compound of the formula III is (2S,3S,5S)-2-(2,6-Dimethylphenoxyacetyl)amino-5-(3R-2,2-dimethyl-1,1-dioxytetrahydrothienyloxycarbonyl) amino-1,6-diphenyl-3-hydroxyhexane.

In a fourth embodiment of the invention, there is a compound of the formula IV:

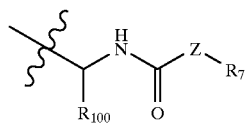

IV or a pharmaceutically acceptable salt, ester or prodrug thereof wherein $R_1$ and $R_4$ are independently selected from the group consisting of loweralkyl, cycloalkylalkyl and arylalkyl;

$R_2$ is —H and $R_3$ is —OH or $R_2$ is —OH and $R_3$ is —H; and one of $R_{13}$ and $R_{14}$ is —$L_7L_8$ wherein $L_7$ is absent or —O— and $L_8$ is a 5- or 6-membered heterocycle having one heteroatom which is —S—, —S(O)— or —S(O)$_2$—, and wherein the heterocycle is unsubstituted or substituted with one or two independently selected loweralkyl groups and the other of $R_{13}$ and $R_{14}$ is

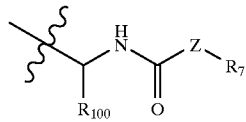

wherein $R_{100}$ is loweralkyl,

Z is —$L_5L_6$ wherein $L_5$ is —O— or —N($R_8$)— wherein $R_8$ is —H, loweralkyl, cycloalkyl or cycloalkylalkyl, and $L_6$ is alkylenyl; and $R_7$ is aryl or a heterocycle.

Preferred compounds of the invention are compounds of the formula IV wherein $R_1$ and $R_4$ are independently selected from the group consisting of (i) benzyl unsubstituted or substituted with one, two or three of —OH or —$C_1$-$C_3$-alkoxy and (ii) —$C_5$-$C_7$-cycloalkylmethyl unsubstituted or substituted with one, two or three of —OH or —$C_1$-$C_3$-alkoxy, and $R_2$, $R_3$, $R_{13}$, and $R_{14}$ are as defined above.

More preferred compounds of the invention are compounds of the formula IV wherein $R_1$ and $R_4$ are unsubstituted benzyl, and $R_2$, $R_3$, $R_{13}$, and $R_{14}$ are as defined above.

Even more preferred compounds of the invention are compounds of the formula IV wherein $R_1$ and $R_4$ are unsubstituted benzyl, $R_2$ and $R_3$ are as defined above, one of $R_{13}$ and $R_{14}$ is —$L_7L_8$ wherein is $L_7L_8$ is as defined above; and the other of $R_{13}$ and $R_{14}$ is

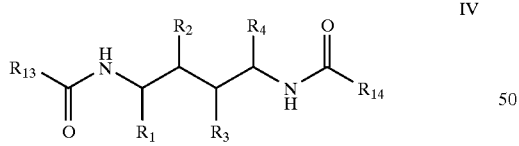

wherein $R_{100}$ is methyl, ethyl, propyl, isopropyl, butyl or t-butyl;

Z is —$L_5L_6$ wherein $L_5$ is —O— or —N($R_8$)— wherein $R_8$ is as defined above and $L_6$ is -alkylenyl-; and $R_7$ is a 5-membered heterocycle having one or two heteroatoms independently selected from the group consisting of —S—, —N— and —O—, wherein the heterocycle is unsubstituted or substituted with loweralkyl or hydroxyalkyl.

A most highly preferred compound of the formula IV is (2S, 3S, 5S)-2-(N-(N-((2-isopropyl-4-thiazolyl) methoxycarbonyl)-L-valinyl)amino)-5-(3R-2,2-dimethyl-1,1-dioxytetrahydrothienyloxycarbonyl)amino-1,6-diphenyl-3-hydrohexane.

The compounds of the invention may comprise asymmetrically substituted carbon atoms. As a result, all stereoisomers of the compounds of the invention are meant to be included in the invention, including racemic mixtures, mixtures of diastereomers, as well as single diastereomers of the compounds of the invention.

The terms "S" and "R" configuration are as defined by the ILLPAC 1974 Recommendations for Section E, Fundamental Stereochemistry, Pure Appl. Chem. (1976) 45, 13–30.

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, -chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, , -dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "activated ester derivative" as used herein refers to acid halides such as acid chlorides, and activated esters including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 2,4,5-trichlorophenol derived esters and the like.

The term "alkanoyl" as used herein refers to $R_{17}C(O)$— wherein $R_{17}$ is a loweraLkyl group.

The term "alkanoyloxy" as used herein refers to $R_{17a}$—O— wherein $R_{17}a$ is an alkanoyl group.

The term "alkenylenyl" as used herein refers to a divalent group derived from a straight or branched chain hydrocarbon containing from 2 to 10 carbon atoms and also containing at least one carbon-carbon double bond. Examples of alkenylene include —CH=CH—, —CH$_2$CH=CH—, —C(CH$_3$)=CH—, —CH$_2$CH=CHCH$_2$—, and the like.

The terms "alkoxy" and "thioalkoxy" as used herein refer to $R_{18}$O— and $R_{18}$S—, respectively, wherein $R_{18}$ is a loweralkyl group.

The term "alkoxyalkoxy" as used herein refers to $R_{19}$O—$R_{20}$O— wherein $R_{19}$ is loweralkyl as defined above and $R_{20}$ is an alkylenyl group. Representative examples of alkoxyalkoxy groups include methoxymethoxy, ethoxymethoxy, t-butoxymethoxy and the like.

The term "alkoxyalkyl" as used herein refers to an alkoxy group appended to a loweralkyl radical.

The term "alkoxycarbonyl" as used herein refers to $R_{21}C(O)$— wherein $R_{21}$ is an alkoxy group.

The term "alkylamino" as used herein refers to —NHR$_{22}$ wherein $R_{22}$ is a loweralkyl group.

The term "alkylaminocarbonyl" as used herein refers to $R_{23}C(O)$— wherein $R_{23}$ is an alkylamino group.

The term "alkylenyl" as used herein refers to a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like.

The term "aminocarbonyl" as used herein refers to —C(O)NH$_2$.

The term "aryl" as used herein refers to a mono- or bicyclic carbocyclic ring system comprising 6 to 12 carbon atoms and having one or two aromatic rings including, but not limited to, phenyl, naphthyl, tetrahydronaphthyl, indanyl, indenyl and the like. Aryl groups can be unsubstituted or substituted with one, two, three or four substituents independently selected from loweralkyl, halo, haloalkyl, haloalkoxy, hydroxyalkyl, alkoxyalkyl, alkanoyloxy, alkoxy, alkoxycarbonyl, thioalkoxy, amino, alkylamino, dialkylamino, aminocarbonyl, mercapto, nitro, carboxaldehyde, carboxy and hydroxy.

The term "arylalkyl" as used herein refers to an aryl group as previously defined, appended to a loweralkyl radical, for example, benzyl and the like.

The term "cycloalkyl" as used herein refers to an aliphatic ring system having 3 to 8 carbon atoms including, but not limited to, cyclopropyl, cyclopentyl, cyclohexyl, and the like.

The term "cycloalkylalkyl" as used herein refers to a cycloalkyl group appended to a loweralkyl radical, including but not limited to cyclohexylmethyl.

The term "dialkylamino" as used herein refers to —NR$_{24}$R$_{25}$ wherein $R_{24}$ and $R_{25}$ are independently selected from loweralkyl groups.

The term "dialkylaminocarbonyl" as used herein refers to $R_{26}$C(O)— wherein $R_{26}$ is a dialkylamino group.

The term "halo" or "halogen" as used herein refers to —Cl, —Br, —I or —F.

The term "haloalkoxy" as used herein refers to $R_{27}$O— wherein $R_{27}$ is a haloalkyl group.

The term "haloalkyl" as used herein refers to a loweralkyl group in which one or more hydrogen atoms are replaced by halogen, for example, chloromethyl, chloroethyl, trifluoromethyl and the like.

The term "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three heteroatoms independently selected from the group consisting of nitrogen, oxygen and sulfur or a 5-membered ring containing 4 nitrogen atoms; and includes a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; two sulfur atoms in non-adjacent positions; two sulfur atoms in adjacent positions and one nitrogen atom; two adjacent nitrogen atoms and one sulfur atom; two non-adjacent nitrogen atoms and one sulfur atom; two non-adjacent nitrogen atoms and one oxygen atom. The 5-membered ring has 0–2 double bonds and the 6- and 7-membered rings have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, benzofuryl, bistetrahydrofuranyl or benzothienyl and the like). Heterocyclics include: azetidinyl, pyrrolyl, pyrrolinyl, pyrrolidinyl, pyrazolyl, pyrazolinyl, pyrazolidinyl, irnidazolyl, imidazolinyl, imidazolidinyl, pyridyl, piperidinyl, homopiperidinyl, pyrazinyl, piperazinyl, pylimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, tetrahydrofuranyl, tetrahydrothienyl, thiazolidinyl, isothiazolyl, triazolyl, tetrazolyl, isoxazolyl, oxadiazolyl, thiadiazolyl, pyrrolyl, pyrimidyl and benzothienyl. Heterocyclics also include compounds of the formnula

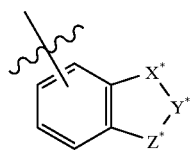

wherein $X^*$ is $-CH_2-$, $-NH-$ or $-O-$, $Y^*$ is $-C(O)-$ or $[-C(R")_2-]_v$ wherein $R"$ is hydrogen or $C_1-C_4$-alkyl and v is 1,2 or 3 and $Z^*$ is $-O-$ or $-NH-$; such as 1,3-benzodioxolyl, 1,4-benzodioxanyl and the like.

Heterocyclics can be unsubstituted or substituted with one, two, three or four substituents independently selected from the group consisting of hydroxy, halo, oxo (=O), alkylimino ($R^*N$=wherein $R^*$ is a loweralkyl group), amino, alkylamino, dialkylamino, alkoxy, alkoxyalkoxy, haloalkyl, cycloalkyl, aryl, arylalkyl, —COOH, —SO$_3$H and loweralkyl. In addition, nitrogen containing heterocycles can be N-protected.

The term "hydroxyalkyl" as used herein refers to a loweralkyl radical to which is appended an hydroxy group.

The term "loweralkyl" as used herein refers to a straight or branched chain alkyl radical containing from 1 to 6 carbon atoms including, but not limited to, methyl, ethyl, n-propyl, isopropyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "thioalkoxyalkyl" as used herein refers to a thioalkoxy group appended to a loweralkyl radical.

The compounds of the invention can be prepared as shown in Schemes I–II. As outlined in Scheme I, intermediates 1 and 2 (wherein $P^1$ is an N-protecting group, for example, t-butyloxycarbonyl and R' represents any of $R_5$, $R_9$, $R_{11}$, $R_{13}$, and $R_{15}$) can be coupled using standard peptide coupling reagents and methods known in the art For example, when intermediate 1 is a carboxylic acid derivative (wherein A is —OH and R' is a group attached to the intermediate via a carbon atom), intermediates 1 and 2 can be reacted in the presence of 1-hydroxybenzotriazole and a diimide such as dicyclohexylcarbodiimide (DCC) or N-ethyl-N'-dimethylaminopropyl carbodiimide (EDAC) and the like to give intermediate 3. Alternatively, an activated ester derivative of intermediate 1 can be reacted with intermediate 2. In this case, R' is a group attached to the intermediate 1 via a heteroatom and A is —OX wherein —OX is an carbonyl activating group such as a para-nitrophenol.

Compound 3 can be N-deprotected to give compound 4. Compound 5 or an activated ester derivative thereof (as described above only R' is replaced with R" wherein R" represents any of $R_6$, $R_{10}$, $R_{12}$, $R_{14}$, and $R_{16}$) can then be coupled to compound 4 to give the compound of the invention 6.

SCHEME 1

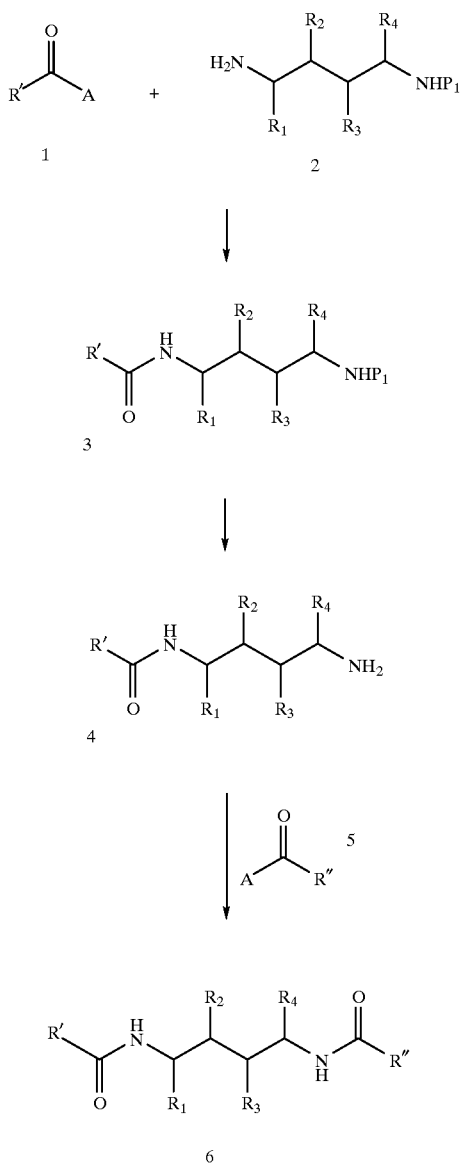

An alternative process is shown in Scheme II. Compound 7 (wherein $P_2$ is an N-protecting group, for example, benzyloxycarbonyl) can be coupled to compound 5, or an activated ester derivative thereof (as described above), to give 8. Compound 8 can be N-deprotected to give 9. Compound 9 can be coupled with compound 1, or an activated ester derivative thereof, to give the compound of the invention 6.

SCHEME 2

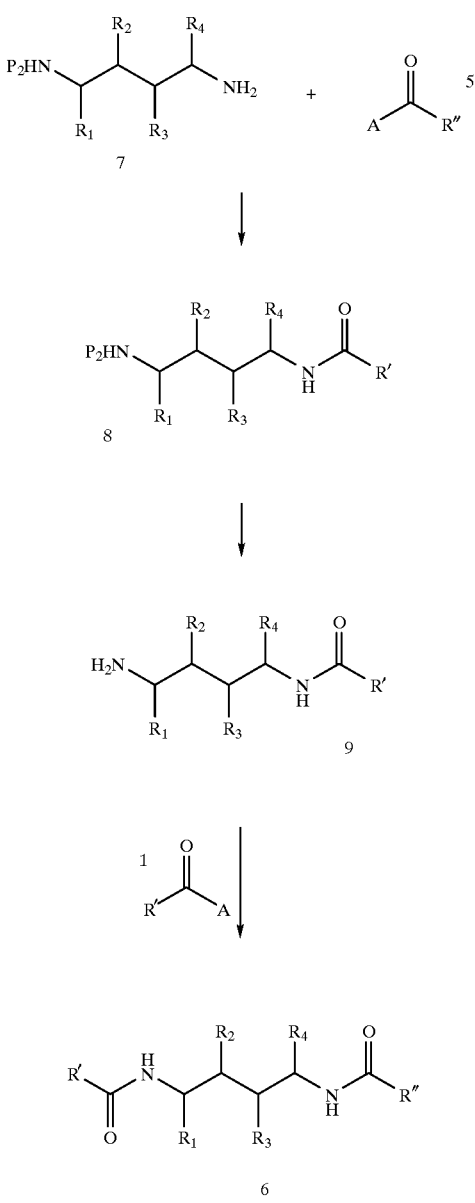

The following examples will serve to further illustrate the preparation of the compounds of the invention.

EXAMPLE 1

(2S,3S,5S)-5-(2,6-Dimethyl-4-amino-phenoxyaceiyl)amino-2-((3R,3aS,6aR)-bis-tetrahydrofuran-3-yl-oxycarbonyl)amino-1,6-diphenyl-3-hydroxyhexane A. ((3R,3aS,6aR)-bis-tetrahydrofuran-3-yl-oxycarbonyl) oxy-4-nitro-benzene: A solution of 582 mg (4.47 mmol) of 3-hydroxyl-(3R,3aS,6aR)-bis-tetrahydrofuran in 10 mL of dichloromethane at 0 ° C under nitrogen atmosphere was treated sequentially with 1.0 mL (9.4 mmol) of 4-methylmorpholine and 993 mg (4.9 mmol) of 4-nitrophenyl chloroformate. The resulting solution was allowed to slowly warm up to ambient temperature and was stirred for 18 h. After washing with three portions of 10% aqueous $NaHCO_3$ and one portion of saturated brine, the solution was dried over $Na_2SO_4$ and concentrated in vacua. The residue was purified by silica gel chromatography by eluting with 1:1 ethyl acetate:hexanes to provide 1.2 g (90%) of the desired compound. $^1$H NMR ($CDCl_3$) δ 1.40 (s, 9H), 1.65 (m, 5H), 2.75 (d, J=6.3 Hz, 2H), 2.86 (d, J=6.3 Hz, 2H), 2.97 (m, 2H), 3.67 (m, 1H), 3.72 (d, J=9.3, 6.0 Hz, 1H), 3.78 (m, 2H), 3.89 (dt, J=7.5, 3.0 Hz, 2H), 4.00 (dd, J=6.6, 6.0 Hz, 1H), 4.54 (br d, J=6.0 Hz, 1H), 5.06 (dt, J=6.3, 2.4 Hz, 1H), 5.68 (d, J=5.6 Hz, 1H), 7.09–7.31 (m, 10H). Mass spectrum: $(M+NH_4)^+$=558.

B. 2-((3R,3aS,6aR)-bis-tetrahydrofuran-3-yl-oxycarbonyl)amino-3-hydroxy-5-(t-butyloxycarbonylamino)-1,6-diphenylhexane: To a solution of 106 mg (0.36 mmol) of ((3R,3aS,6aR)-bis-tetrahydrofuran-3-yl-oxycarbonyl)oxy-4-nitro benzene in 3 mL of 1,2-dichloroethane was added (2S,3S,5S)-2-amino-3-hydroxy-5-(t-butyloxycarbonylamino)-1,6-diphenylhexane. The resulting solution was refluxed for 12 h. After washing with three portions of 10% aqueous $NaHCO_3$ and one portion of saturated brine, the solution was dried over $Na_2SO_4$ and concentrated in vacuo. The residue was purified by silica gel chromatography by eluting with 30–50% of ethyl acetate:hexanes to provide 163 mg (84%) of the desired compound. $^1$H NMR ($CDCl_3$) δ 1.40 (s, 9H), 1.65 (m, 5H), 2.75 (d, J=6.3 Hz, 2H), 2.86 (d, J=6.3 Hz, 2H), 2.97 (m, 2H), 3.67 (m, 1H), 3.72 (dd, J=9.3, 6.0 Hz, 1H), 3.78 (m, 2H), 3.89 (dt, J=7.5, 3.0 Hz, 2H), 4.00 (dd, J=6.6, 6.0 Hz, 1H), 4.54 (br d, J=6.0 Hz, 1H), 5.06 (dt, J=6.3, 2.4 Hz, 1H), 5.68 (d, J=5.6 Hz, 1H), 7.09–7.31 (m, 10H). Mass spectrum: $(M+NH_4)^+$=558.

C. 2-((3R,3aS,6aR)-bis-tetrahydrofuran-3-yl-oxycarbonyl)amino-3-hydroxy-5-amino-1,6-diphenylhexane: To a solution of 163 mg (0.30 mmol) of 2-((3R,3aS,6aR)-bis-tetrahydrofuran-3-yl-oxycarbonyl) amino-3-hydroxy-5-(t-butyloxycarbonylamino)-1,6-diphenylhexane in 2.5 mL of dichloromethane was added 200 μL of trifloruacetic acid. After the reaction was finished as indicated by TLC, the solvent was removed under reduced pressure. The residue was dissolved in methylene chloride and washed with saturated aqueous $NaHCO_3$ and saturated brine. The combined organic layer was dried over $Na_2SO_4$ and concentrated in vacuo to give 123 mg (93%) of product as a white solid. The product was used without further purification. $^1$H NMR ($CDCl_3$) δ 1.53 (m, 3H), 1.75 (dt, J=7.5, 2.4 Hz, 1H), 1.74 (d, J=8.1 Hz, 1H), 2.52 (dd, J=8.7, 13.5 Hz, 1H), 2.83 (m, 2H), 2.88 (dd, J=7.3, 3.0 Hz 1H), 2.97 (m, 1H), 3.11 (m, 1H), 3.73 (m, 2H), 3.82 (m, 3H), 3.91 (m, 1H), 4.01 (dd, J=9.3, 6.0 Hz, 1H), 5.11 (dd, J=14.1, 6.0 Hz, 1H), 5.39 (d, J=9.3 Hz, 1H), 5.69 (d, J=9.3 Hz, 1H), 7.08–7.34 (m, 10H). Mass spectrum: $(M+H)^+$=441.

D. 5-(2,6-Dimethyl-4-nitro-phenoxyacetyl)amino)-2-((3R,3aS,6aR)-bis-tetrahydrofuran-3-yl-oxycarbonyl) amino-1,6-diphenyl-3-hydroxyhexane: To a solution of 100 mg (0.23 mmol) of 2-((3R,3aS,6aR)-bis-tetrahydrofuran-3-yl-oxycarbonyl)amino-3-hydroxy-5-amino-1,6-diphenylhexane in 1 mL of THF and 1 mL of methylene chloride was subsequently added 51.1 mg (0.23 mmol) of 2,6-dimethyl-4-nitro-phenyloxy acetic acid, 44 mg (0.23 mmol) of EDIC, 3.1 mg (0.023 mmol) of HOBT, and 63 μL (0.46 mmol) of triethyl amine. The resulting solution was allowed to stir at ambient temperature for 6 h, and concentrated in vacuo. The residue was taken up in ethyl acetate, washed with one portion of 3N HCl solution, one portion of 10% aqueous $NaHCO_3$, and one portion of saturated brine, dried over $MgSO_4$, and concentrated in vacuo. The resulting product mixture was purified by silica gel chromatography using 80% ethyl acetate:hexanes as an eluent to provide 126 mg (85%) of the desired compound. $^1$H NMR (CDCl$_3$) δ 1.68 (m, 2H), 1.72 (m, 2H), 2.18 (s, 6H), 2.70–3.03 (m, 5H), 3.50 (d, J=4.2 Hz, 1H), 3.77 (dd, J=9.0, 6.0 Hz, 1H), 3.79 (m, 1H), 3.88 (dd, J=15.0, 9.0 Hz, 2H), 4.01 (dd, J=9.0, 6.3 Hz, 1H), 4.10 (d, J=15.0 Hz, 1H), 4.28 (d, J=15.0 Hz, 1H), 4.35 (m, 1H), 5.07 (t, J=9.0 Hz, 1H), 5.08 (dd, J=15.0, 6.0 Hz, 2H), 5.69 (d, J=5.4 Hz, 1H), 6.82–7.32 (m, 10H), 7.91 (s, 2H). Mass spectrum: (M+H)$^+$=648.

E. 5-(2,6-Dimethyl-4-amino-phenoxyacetyl)amino-2-((3R,3aS,6aR)-bis-tetrahydrofuran-3-yl-oxycarbonyl)amino-1,6-diphenyl-3-hydroxyhexane: To a solution of 120 mg (0.19 mmol) of 5-(2,6-dimethyl-4-nitro-phenoxyacetyl)amino-2-((3R,3aS,6aR)-bis-tetrahydrofuran-3-yl-oxycarbonyl)amino-1,6-diphenyl-3-hydroxyhexane in 3 mL of methanol was added 20 mg of Pd/C(10%). The reaction mixture was stirred under one atmosphere of hydrogen for 2 h. The Pd/C was removed over a celite pad, and the solvent was evaporated to dryness under reduced pressure to give 110 mg (96%) of desired product as a white solid. $^1$H NMR (CDCl$_3$) δ 1.27 (m, 1H), 1.68 (m, 2H), 1.79 (m, 2H), 2.02 (s, 6H), 2.70–3.03 (m, 5H), 3.74 (m, 3H), 3.88 (dq, J=8.4, 3.0 Hz, 2H), 4.00 (dd, J=6.0, 3.0 Hz, 1H), 4.03 (d, J=15.0 Hz, 1H), 4.18 (d, J=15.0 Hz, 1H), 4.27 (m, 1H), 5.06 (t, J=3.3 Hz, 1H), 5.07 (dd, J=15.0, 7.5 Hz, 1H), 5.68 (d, J=4.5 Hz, 1H), 6.32 (s, 2H), 6.96 (d, J=8.1 Hz, 1H), 7.14–7.30 (m, 10H). Mass spectrum: (M+H)$^+$=618.

EXAMPLE 2

(2S,3S,5S)-5-(2,6-Dimethyl-4-amino-phenoxyactyl)amino-2-((3S,3aR,6aS)-bis-tetrahydrofuran-3-yl-oxycarbonyl)amino-1,6-diphenyl-3-hydroxyhexane A. ((3S,3aR,6aS)-bis-tetrahydrofuran-3-yl-oxycarbonyl)oxy-4-nitro-benzene: To a solution of 460 mg (3.5 mmol) of 3-hydroxyl-(3S,3aR,6aS)-bis-tetrahydrofuran in 10 mL of dichloromethane at 0° C. under nitrogen atmosphere was treated sequentially with 820 μL (7.4 mmol) of 4-methylmorpholine and 785 mg (3.9 mmol) of 4-nitrophenyl chloroformate. The resulting solution was allowed to slowly warm up to ambient temperature and was stirred for 18 h. After washing with three portions of 10% aqueous NaHCO$_3$ and one portion of saturated brine, the solution was dried over Na$_2$SO$_4$ and concentrated in vacuo. The residue was purified by silica gel chromatography by eluting with 1:1 ethyl acetate:hexanes to provide 820 mg (79%) of the desired compound. $^1$H NMR (CDCl$_3$) δ 2.03 (m, 1H), 2.20 (m, 1H), 3.06 (m, 1H), 3.98 (m, 2H), 4.04 (m, 1H), 4.16 (dd, J=9.6, 6.0 Hz, 1H), 5.26 (dd, J=6.3 Hz, 1H), 5.78 (d, J=5.4 Hz, 1H), 7.40 (d, J=9.0 Hz, 2H), 8.31 (d, J=9.0 Hz, 2H). Mass spectrum: (M+NH$_4$)$^+$=313.

B. 2-((3S,3aR,6aS)-bis-tetrahydrofuran-3-yl-oxycarbonyl)amino-3-hydroxy-5-(t-butyloxycarbonylamino)-1,6-diphenylhexane: To a solution of 400 mg (1.36 mmol) of ((3S,3aR,6aS)-bis-tetrahydrofuran-3-yl-oxycarbonyl)oxy-4-nitro benzene in 9 mL of 1,2-dichloroethane was added 521 mg (1.36 mmol) of (2S,3S,5S)-2-amino-3-hydroxy-5-(t-butyloxycarbonylamino)-1,6-diphenylhexane. The resulting solution was refluxed for 12 h. After washing with three portions of 10% aqueous NaHCO$_3$ and one portion of saturated brine, the solution was dried over Na$_2$SO$_4$ and concentrated in vacuo. The residue was purified by silica gel chromatography by eluting with 30–50% of ethyl acetate:hexanes to provide 660 mg (90%) of the desired compound.

C. 2-((3S,3aR,6aS)-bis-tetrahydrofuran-3-yl-oxycarbonyl)amino-3-hydroxy-5-amino-1,6-diphenylhexane: To a solution of 660 mg (1.2 mmol) of 2-((3S,3aR,6aS)-bis-tetrahydrofuran-3-yl-oxycarbonyl)amino-3-hydroxy-5-(t-butyloxycarbonylamino)-1,6-diphenylhexane in 2.5 mL of dichloromethane was added 200 μL of trifluoroacetic acid. After the reaction was finished as indicated by TLC, the solvent was removed under reduced pressure. The residue was dissolved in methylene chloride and washed with saturated aqueous NaHCO$_3$ and saturated brine. The combined organic layer was dried over Na$_2$SO$_4$ and concentrated in vacuo to give 485 mg (92%) of product as a white solid. The product was used without further purification. $^1$H NMR (CDCl$_3$) δ 1.62 (t, J=6.3 Hz, 2H), 1.85 (m, 1 H), 2.02 (m, 1H), 2.73 (d, J=6.0 Hz, 2H), 2.86 (d, J=7.5 Hz, 2H), 3.03 (m, 1H), 3.40 (m, 1H), 3.63 (dd, J=12.0, 6.0 Hz, 2H), 3.74 (q, J=7.8 Hz, 1H), 4.00 (dd, J=9.0, 6.0 Hz, 2H), 4.53 (m 1H), 5.07 (m, 2H), 5.71 (d, J=5.7 Hz, 1H), 7.10 (d, J=7.5 Hz, 2H), 7.16–7.30 (m, 8H). Mass spectrum: (M+H)$^+$=441.

D. 5-(2,6-Dimethyl-4-nitro-phenoxyacetylamino-2-((3S,3aR,6aS6-bis-tetrahydrofuran-3-oxycarbonyl)amino-1,6-diphenyl-3-hydroxyhexane: To a solution of 55 mg (0.12 mmol) of 2-((3S,3aR,6aS)-bis-tetrahydrofuran-3-yl-oxycarbonyl)amino-3-hydroxy-5-amino-1,6-diphenylhexane in 0.6 mL of THF and 0.6 mL of methylene chloride was subsequently added 28 mg (0.12 mmol) of 2,6-dimethyl-4-nitro-phenyloxy acetic acid, 24 mg (0.12 mmol) of EDIC, 2 mg (0.01 mmol) of HOBT, and 50 μL (0.12 mmol) of triethyl amine. The resulting solution was allowed to stir at ambient temperature for 6 h, and concentrated in vacuo. The residue was taken up in ethyl acetate, washed with one portion of 3N HCl solution, one portion of 10% aqueous NaHCO$_3$, and one portion of saturated brine, dried over MgSO$_4$, and concentrated in vacuo. The resulting product mixture was purified by silica gel chromatography using 80% ethyl acetate:hexanes as an eluent to provide 73 mg (90%) of the desired compound. $^1$H NMR (CDCl$_3$) δ 1.80 (t, J=6.3 Hz, 2H), 1.89 (m, 1H), 2.03 (m, 1H), 2.07 (s, 6H), 2.91 (m, 4H), 3.02 (m, 1H), 3.42 (d, J=4.2 Hz, 1H), 3.64 (dd, J=9.0, 63 Hz, 1H), 3.74 (m, 1H), 3.85 (m, 1H), 3.96 (m, 1H), 4.01 (dd, J=9.6, 6.3 Hz, 1H), 4.11 (d, J=15 Hz, 1H), 4.25 (d, J=15 Hz, 1H), 4.33 (m, 1H), 5.07 (m, 2H), 5.72 (d, J=6.80 (d, J=7.5 Hz, 1H), 7.13–7.32 (m, 10H), 7.91 (s, 2H). Mass spectrum: (M+H)$^+$=648.

E. 5-(2,6-Dimethyl-4-amino-phenoxvacetyl)amino-2-((3S,3aR,6aS)-bis-tetrahvdrofuran-3-yl-oxycarbonyl)amino-1,6-diphenyl-3-hydroxyhexane: To a solution of 73 mg (0.11 mmol) of 5-(2,6-dimethyl-4-nitro-phenoxyacetyl)amino-2-((3S,3aR,6aS)-bis-tetrahydrofuran-3-yl-oxycarbonyl)amino-1,6-diphenyl-3-hydroxyhexane in 3 mL of methanol was added 15 mg of Pd/C(10%). The reaction mixture was stirred under one atmosphere of hydrogen for 2 h. The Pd/C was removed over a celite pad, and the solvent was evaporated to dryness under reduced pressure to give 60.4 mg (74%) of desired product as a white solid. $^1$H NMR (CDCl$_3$) δ 1.27 (d, J=3.0 Hz, 1H), 1.77 (m, 2H), 1.87 (m, 1H), 2.02 (s, 6H), 2.78–2.95 (m, 5H), 3.03 (dq, J=15.3, 3.0 Hz, 1H), 3.48 (m, 1 H), 3.62 (dd, J=9.3, 6.0 Hz, 1H), 3.71 (m, 2H), 3.83 (m, 2H), 3.97 (dq, J=8.4, 3.0 Hz, 1H), 4.03 (d, J=15 Hz, 1H), 4.14 (t, J=150 Hz, 1H), 4.27 (m, 1H), 5.07 (t, J=12.9, 8.1 Hz, 1H), 5.09 (dd, J=12.6, 9.0, 1H), 5.71 (d, J=5.4 Hz, 1H), 6.32 (s, 2H), 6.94 (d, J=7.8 Hz, 1H), 7.12–7.32 (m, 10H). Mass spectrum: (M+H)$^{+-}$618.

EXAMPLE 3

(2S,3S,5S)-2-(2, 6-Dimethyl-4-amino-phenoxyacetyl)amino-5-((3R,3aS,6aR)-bis-tetrahydrofuran-3-yl-oxycarbonyl)amino-1,6-diphenyl-3-hydroxyhexane A. 2-(2, 6-Dimethyl-4-nitro-phenoxyacetyl)amino-3-hydroxy-5-(t-butloxycarbonylamino)-1,6-diphenylhexane:

To a solution of 223 mg (0.58 mmol) of (2S,3S,5S)-2-amino-3-hydroxy-5-(t-butyloxycarbonylamino)-1,6-diphenylhexane in 2 mL of THF and 2 mL of methylene chloride was subsequently added 133 mg (0.64 mmol) of 2,6-dimethyl-4-nitro-phenyloxy acetic acid, 122 mg (0.64 mmol) of EDIC, 8.0 mg (0.06 mmol) of HOBT, and 90 μL (0.64 mmol) of triethyl amine. The resulting solution was allowed to stir at ambient temperature for 6 h, and concentrated in vacuo. The residue was taken up in ethyl acetate, washed with one portion of 3N HCl solution, one portion of 10% aqueous $NaCHO_3$, and one portion of saturated brine, dried over $MgSO_4$, and concentrated in vacuo. The resulting product mixture was purified by silica gel chromatography using 40% ethyl acetate:hexanes as an eluent to provide 312 mg (94%) of the desired compound.

B. 2-(2, 6-Dimethyl-4-nitro-phenoxyacetyl)amino-3-hydroxy-5-amino-1,6-diphenylhexane: To a solution of 312 mg (0.54 mmol) of 2-(2, 6-Dimethyl-4-nitro-phenoxyacetyl) amino-3-hydroxy-5-(t-butyloxycarbonylamino)-1,6-diphenylhexane in 3 mL of dichloromethane was added 800 μL of tifloruacetic acid. After the reaction was finished as indicated by TLC, the solvent was removed under reduced pressure. The residue was dissolved in methylene chloride and washed with saturated aqueous $NaCHO_3$ and saturated brine. The combined organic layer was dried over $Na_2SO_4$ and concentrated in vacuo to give 248 mg (96%) of product as a white solid. The product was used without further purification.

C. 2-(2, 6-Dimethyl-4nitro-phenoxyacetyl)amino-5-((3R,3aS.6aR)-bis-tetrahydrofuran-3-yl-oxvcarbonyl)amino-1,6-diphenyl-3-hydroxhexane: To a solution of 160 mg (0.54 mmol) of ((3R,3aS,6aR)-bis-tetrahydrofuran-3-yl-oxycarbonyl)oxy-4-nitro benzene in 3 mL of 1,2-dichloroethane was added 248 mg (0.52 mmol) of 2-(2, 6-dimethyl-4-nitro-phenoxyacetyl)amino-3-hydroxy-5-amino-1,6-diphenylhexane. The resulting solution was refluxed for 12 h. After washing with three portions of 10% aqueous $NaCHO_3$ and one portion of saturated brine, the solution was dried over $Na_2SO_4$ and concentrated in vacuo. The residue was purified by silica gel chromatography by eluting with 60% of ethyl acetate:hexanes to provide 295 mg (87%) of the desired compound.

D. 2-(2,6-Dimethyl-4-amino-phenoxyacetyl)amino-5-((3R,3aS,6aR)-bis-tetrahydrofuran-3-yl-oxycarbonyl)amino-1,6-diphenyl-3-hydroxyhexane: To a solution of 295 mg (0.46 mmol) of 2-(2,6-dimethyl-4-amino-phenoxyacetyl)amino-3-hydroxy-5-((3R,3aS,6aR)-bis-tetrahydrofuran-3-yl-oxycarbonyl)-amino-1,6-diphenylhexane in 4 mL of methanol was added 40 mg of Pd/C(10%). The reaction mixture was stirred under one atmosphere of hydrogen for 2 h. The Pd/C was removed over a celite pad, and the solvent was evaporated to dryness under reduced pressure to give 280 mg (99%) of desired product as a white solid. $^1$H NMR (d$_6$-DMSO) δ 1.44 (m, 2H), 1.52 (m, 3H), 2.01 (s, 6H), 2.65 (m, 1H), 2.82 (d, 2H, J=7.5 Hz, 2H), 3.54 (dd, J=9.0, 3.0, 1H), 3.61 (t, J=6.0 Hz, 2H), 3.64 (d, J=6.3 Hz, 1H), 3.75 (dt, J=8.1, 3.0 Hz, 1H), 3.85 (dd, J=9.3, 6.0 Hz, 2H), 3.96 (d, J=4.5 Hz, 1H), 4.28 (q, J=9.0 Hz, 1H), 4.69 (s, 2H), 4.87 (dd, J=15.0, 6.0 Hz, 1H), 5.03 (d, J=6.0 Hz, 1H), 5.53 (d, J=5.7 Hz, 1H), 6.19 (s, 2H), 7.10–7.26 (m, 10H), 7.42 (d, J=15.0 Hz, 1H ). Mass spectrum: (M+H)$^+$=618.

EXAMPLE 4

(2S,3S,5S)-5-(2,4,6-Trimethyl-3-amino-phenoxyacetyl)amino-2-((3R,3aS,6aR)-bis-tetrahydrofuran-3-yl-oxycarbonyl)amino-1,6-diphenyl-3-hydroxyhexane A. Ethyl 2,4,6-Trimethyl-3-nitro-phenyloxy Acetate: To a −10° C. solution of ethyl 2,4,6-trimethylphenyloxy acetate 4.2 g (0.02 mol) in 20 mL of acetic acid and 10 mL of acetic anhydride was added 2 mL of consentrated nitric acid dropwise over 10 min. The reaction was allowed to warm up to room temperature for over a period of 1 h. An additional 1 mL of consentrated nitric acid was added, and the reaction was stirred overnight. The reaction mixture was dissolved in ether and partioned between ether and water. The organic phase was washed with saturated sodium bicarbonate and brine, dried over sodium sulfate and evaporated to dryness under reduced pressure. The residue was purified by silica gel chromatography by eluting with 10% of ether:hexanes to provide 980 mg (20%) of the desired compound. $^1$H NMR (CDCl$_3$) δ 1.33 (t, J=7.5 Hz, 3H), 2.23 (s, 3H), 2.25 (s, 3H), 2.31 (s, 3H), 4.31 (q, J=7.5 Hz, 2H), 4.38 (s, 2H), 6.95 (s, 1 H). Mass spectrum: (M+H)$^+$=267.

B. 2,4,6-Trimethyl-3-nitro-phenyloxyacetic Acid: To a solution of 0.98 g (0.39 mmol) of ethyl 2,4,6-dimethyl-3-nitro phenoxyacetate in 10 mL of methanol was added 1 mL of 3N sodium hydroxide. After the reaction mixture was stirred at room temperature for 30 min, it was acidified with 3N HCl and partitioned between water and methylene chloride. The combined organic extracts were washed with brine and dried over anhydrous sodium sulfate, filtered and evaporated to dryness under reduced pressure to give 0.82 g (94%) of 2,4,6-dimethyl-3-nitro phenoxyacetic acid which was recrystaiaed in ethyl acetate and hexanes to give 587 mg of desired compound as light yellow prism. $^1$H NMR (d$_6$-DMSO) δ 2.16 (s, 3H), 2.17 (s, 3H), 2.26 (s, 3H), 4.43 (s, 2H), 7.15 (s, 1H), 13.02 (bs, 1H). Mass spectrum: (M+NH$_4$)$^+$=257.

C. 5-(2,4,6-Trimethyl-3-nitro-phenoxyacetyl)amino-2-((3R,3aS,6aR)-bis-tetrahydrofuran-3-yl-oxycarbonyl)amino-1,6-diphenyl-3-hdroxyhexane: To a solution of 100 mg (0.23 mmol) of 2-((3R,3aS,6aR)-bis-tetrahydrofuran-3-yl-oxycarbonyl)amino-3-hydroxy-5-amino-1,6-diphenylhexane in 1 mL of THF and 1 mL of methylene chloride was subsequently added 54 mg (0.23 mmol) of 2,4,6-trimethyl-3-nitro-phenyloxyacetic acid, 44 mg (0.23 mmol) of EDIC, 3.1 mg (0.023 mmol) of HOBT, and 63 μL (0.46 mmol) of triethyl amine. The resulting solution was allowed to stir at ambient temperature for 6 h, and concentrated in vacuo. The residue was taken up in ethyl acetate, washed with one portion of 3N HCl solution, one portion of 10% aqueous NaHCO$_3$, and one portion of saturated brine, dried over MgSO$_4$, and concentrated in vacuo. The resulting product mixture was purified by silica gel chromatography using 80% ethyl acetate:hexanes as an eluent to provide 110 mg (72%) of the desired compound. $^1$H NMR (CDCl$_3$) δ 1.60–1.73 (m, 4H), 2.01 (s, 3H), 2.19 (s, 3H), 2.23 (s, 3H), 2.79–3.01 (m, 5H), 3.75 (dd, J=9.0, 6.0 Hz, 1H), 3.79 (m, 1H), 3.79 (m, 1H), 3.90 (dt, J=8.4, 3.0 Hz, 2H), 4.00 (dd, J=9.0, 6.3 Hz, 1H), 4.04 (d, J=15.0 Hz, 1H), 4.21 (d, J=15.0 Hz, 1H), 4.32 (m, 1H), 5.07 (t, J=5.4 Hz, 1H), 5.08 (q, J=8.4 Hz, 1H) 5.68 (d, J=4.5 Hz, 1H), 6.82 (d, J=7.5 Hz, 1H), 6.93 (s, 1H), 7.12–7.32 (m, 10H). Mass spectrum: (M+H)$^+$=662.

D. 5-(2,4,6-Trimethyl-3-amino-phenoxyacetyl)amino)-2-((3R,3aS,6aR)-bis-tetrahydrofuran-3-yl-oxycarbonyl)amino-1,6-diphenyl-3-hydroxyhexane; To a solution of 110 mg (0.16 mmol) of 5-(2,4,6-trimethyl-3-nitro-phenoxyacetyl)amino-2-((3R,3aS,6aR)-bis-tetrahydrofuran-3-yl-oxycarbonyl)amino-1,6-diphenyl-3-hydroxyhexane in 3 mL of methanol was added 20 mg of Pd/C(10%). The reaction mixture was stirred under one atmosphere of hydrogen for 2 h. The Pd/C was removed over a celite pad, and the solvent was evaporated to dryness under reduced pressure to give 98 mg (97%) of desired product as a white solid. $^1$H NMR (CDCl$_3$) δ 1.68 (m, 3H), 1.80 (t, J=6.0 Hz, 1H), 1.93

(s, 3H), 2.00 (s, 3H), 2.12 (s, 3H), 2.79–3.01 (m, 5H), 3.50 (m, 1H), 3.77 (m, 3H), 3.89 (dq, J=9.6, 6.0 Hz, 1H), 4.02 (dd, J=9.6, 6.0 Hz, 1H), 4.03 (d, J=15.0 Hz, 1H), 4.18 (d, J=15.0 Hz, 1H), 4.29 (m, 1H), 5.08 (q, J=7.5 Hz, 1H), 5.09 (q, J=7.5 Hz, 1H), 5.68 (d, J=6.0 Hz, 1H), 6.74 (s, 1H), 7.00 (d, J=8.1 Hz, 1H), 7.12–7.32 (m, 10H). Mass spectrum: $(M+H)^+$=632.

EXAMPLE 5

(2S,3S,5S)-5-(2,6-Dimethyl-phenoxyacetyl)amino-2-((3R,3aS,6aR)-bis-tetrahydrofuran-3-yl-oxycarbonyl)amino-1,6-diphenyl-3-hydroxyhexane To a solution of 100 mg (0.23 mmol) of 2-((3R,3aS,6aR)-bis-tetrahydrofuran-3-yl-oxycarbonyl)amino-3-hydroxy-5-amino-1,6-diphenylhexane in 1 mL of THF and 1 mL of methylene chloride was subsequently added 41 mg (0.23 mmol) of 2,6-dimethyl-phenyloxy acetic acid, 44 mg (0.23 mmol) of EDIC, 3.1 mg (0.023 mmol) of HOBT, and 63 βL (0.46 mmol) of triethyl amine. The resulting solution was allowed to stir at ambient temperature for 6 h, and concentrated in vacuo. The residue was taken up in ethyl acetate, washed with one portion of 3N HCl solution, one portion of 10% aqueous $NaHCO_3$, and one portion of saturated brine, dried over $MgSO_4$, and concentrated in vacuo. The resulting product mixture was purified by silica gel chromatography using 80% ethyl acetate:hexanes as an eluent to provide 111 mg (90%) of the desired compound. $^1$H NMR ($CD_3OD$) δ 1.48 (m, 1H), 1.56 (m, 1H), 1.77 (m, 2H), 2.15 (s, 6H), 2.73–2.95 (m, 5H), 3.71 (m, 3H), 3.79 (dq, J=7.5, 2.5 Hz, 1H), 3.93 (dd, J=9.0, 6.0 Hz, 1H), 4.02 (d, J=15.0 Hz, 1H), 4.10 (m, 1H), 4.13 (d, J=15.0 Hz, 1H), 4.55 (m, 1H), 4.95 (m, 1H), 4.97 (dd, J=13.5, 6.0 Hz, 1H), 5.60 (d, J=7.1 Hz, 1H), 6.95 (m, 3H), 7.12–7.28 (m, 11H). Mass spectrum: $(M+H)^+$=603.

EXAMPLE 6

(2S,3S,5S)-2-(2,6-Dimethyl-phenoxyacetyl)amino-5-((3R,3aS,6aR)-bis-tetrahydrofuran-3-yl-oxycarbonyl)amino-1,6-diphenyl-3-hydroxyhexane A. 2-(2,6-Dimethyl-phenoxyacetyl)amino-3-hydroxy-5-(t-butyloxycarbonylamino)-1,6-diphenylhexane: To a solution of 162 mg (0.42 mmol) of (2S,3S,5S)-2-amino-3-hydroxy-5-(t-butyloxycarbonylamino)-1,6-diphenylhexane in 3 mL of $CHCl_3$ was added 100 mg (0.64 mmol) of N-(2,6-dimethyl-phenyloxy acetyloxy)succinimide. The resulting solution was refluxed for 4 h. The solvent was removed under reduced pressure, and the residue was purified by silica gel chromatography using 30% ethyl acetate:hexanes as an eluent to provide 205 mg (99%) of the desired compound. $^1$H NMR ($CDCl_3$) δ 1.58 (s, 9H), 1.68 (m, 2H), 2.17 (s, 6H), 2.78 (m, 2H), 2.97 (d, J=7.5 Hz, 2H), 3.75 (m, 2H), 3.90 (q, J=8.1 Hz, 1H), 4.15 (t, J=7.5 Hz, 1H), 4.19 (s, 2H), 4.60 (m, 1H), 6.98 (m, 3H), 7.13 (d, J=6.6 Hz, 1H), 7.18–7.30 (m, 10H). Mass spectrum: $(M+H)^+$=547.

B. 2-(2,6-Dimethyl-phenoxyacetyl)amino-3-hydroxy-5-amino-1,6-diphenylhexane: To a solution of 205 mg (0.38 mmol) of 2-(2,6-dimethyl-phenoxyacetyl)amino-3-hydroxy-5-(t-butyloxycarbonylamino)-1,6-diphenylhexane in 3 mL of dichloromethane was added 300 μL of trifluoroacetic acid. After the reaction was finished as indicated by TLC, the solvent was removed under reduced pressure. The residue was dissolved in methylene chloride and washed with saturated aqueous $NaHCO_3$ and saturated brine. The combined organic layer was dried over $Na_2SO_4$ and concentrated in vacuo to give 126 mg (74%) of product as a white solid. The product was used without further purification. $^1$H NMR ($CDCl_3$) δ 1.39 (dd, J=8.7, 14.4 Hz, 1H), 1.44 (d, J=14.1 Hz, 1H), 1.60 (m, 2H), 2.24 (s, 6H), 2.44 (dd, J=13.5, 7.5 Hz, 1H), 2.81 (dd, J=13.5, 4.5 Hz, 1H), 2.98 (dd, J=8.4, 6.6 Hz, 2H), 3.06 (m, 2H), 3.92 (d, J=13.5 Hz, 1H), 4.17 (q, J=7.8 Hz, 1H), 4.27 (s, 2H), 6.99 (m, 3H), 7.10 (d, J=6.9 Hz, 2H), 7.19–7.33 (m, 8H), 7.44 (d, J=9.6 Hz, 1H). Mass spectrum: $(M+H)^+$=447.

C. 2-(2,6-Dimethy-phenoxyacetyl)amino-5-((3R,3aS,6aR)-bis-tetrahydrofuran-3-yl-oxycarbonyl)amino-1,6-diphenyl-3-hydroxyhexane: To a solution of 160 mg (0.54 mmol) of ((3R,3aS,6aR)-bis-tetrahydrofuran-3-yl-oxycarbonyl)oxy-4-nitro benzene in 3 mL of 1,2-dichloroethane was added 248 mg (0.52 mmol) of 2-(2,6-dimethyl-phenoxyacetyl)amino-3-hydroxy-5-amino-1,6-diphenylhexane. The resulting solution was refluxed for 12 h. After washing with three portions of 10% aqueous $NaHCO_3$ and one portion of saturated brine, the solution was dried over $Na_2SO_4$ and concentrated in vacuo. The residue was purified by silica gel chromatography by eluting with 60% of ethyl acetate:hexanes to provide 295 mg (87%) of the desired compound. $^1$H NMR ($CDCl_3$) δ 1.64–1.78 (m, 4H), 2.17 (s, 6H), 2.81 (d, J=6.3 Hz, 2H), 2.96 (m, 1H), 3.00 (d, J=7.8 Hz, 2H), 3.36 (d, J=6.0 Hz, 1H), 3.72 (dd, J=9.0, 6.0 Hz, 1H), 3.81 (m, 1H), 3.88 (dt, J=8.1, 3.0 Hz, 1H), 3.99 (dd, J=9.0, 6.0, 2H), 4.03 (m, 1H), 4.18 (m, 1H), 4.22 (d, J=6.0 Hz, 1H), 4.91 (d, J=7.8 Hz, 1H), 5.09 (dd, J=13.5, 7.5 Hz, 1H), 5.68 (d, J=5.4 Hz, 1H), 7.00 (m, 3H), 7.13 (d, J=7.5 Hz, 2H), 7.19–7.33 (m, 9H). Mass spectrum: $(M+H)^+$=603.

EXAMPLE 7

(2S,3S,5S)-5-(2-Hydroxymethyl-6-methyl-phenoxyacetyl)amino-2-((3R,3aS,6aR)-bis-tetrahydrofuran-3-yl-oxycarbonyl)amino-1,6-diphenyl-3-hydroxyhexane A. 2-Hydroxymethyl-6-methyl-phenol: To a 0° C. solution of 13 mL of 1N lithium aluminum hydride in THF was added 2 mL of THF solution of 3-methyl salicylate (1.0 g, 6.5 mmol) dropwise over 10 min. The reaction mixture was allowed to slowly warm up to room temperature for 30 min and then stirred at room temperature for 1 h. The reaction was quenched by slow addition of 3N HCl, and partitioned between methylene chloride and water. The organic phase was washed with brine, dried over anhydrous sodium sulfate, filtered and evaporated to dryness under reduced pressure to give 1.0 g (99%) of 2-hydrooxymethyl-6-methyl phenol which was used without further purification. $^1$H NMR ($CDCl_3$) δ 2.27 (s, 3H), 4.87 (s, 2H), 6.76 (t, J=7.5 Hz, 1H), 6.88 (d, J=7.5 Hz, 1H), 7.09 (d, J=7.5 Hz, 1H), 7.38 (s, 1H). Mass spectrum: $(M+NH_4)^+$=156.

B. 2-Tert-butyl-dimethylsilyloxymethyl-6-methyl Phenol: To a stirred solution of 1.44 g (9.34 mmol) of 2-hydroxymethyl-6-methyl phenol in methylene chloride at 0° C. was added 1.41 g (9.34 mmol) of tert-butyl dimethylsilyl chloride and 760 mg (11.2 mmol) of imidazole. After the reaction was stirred for 8 h, it was partitioned between methylene chloride and diluted sodium bicarbonate solution. The combined organic extracts were washed with brine and dried over anhydrous sodium sulfate, filtered and evaporated to dryness under reduced pressure. The residue was purified over a short silica gel column eluting with 5% of ether:hexanes to provide 1.96 g (83%) of the desired compound. $^1$H NMR ($CDCl_3$) δ 0.15 (s, 6H), 0.93 (s, 9H), 2.24 (s, 3H) 4.89 (s, 2H), 6.72 (t, J=7.5 Hz, 1H), 6.79 (d, J=7.5 Hz, 1H), 7.05 (d, J=7.5 Hz, 1H), 8.17 (s, 1H). Mass spectrum: $(M+H)^+$=253.

C. Ethyl 2-Tert-butyl-dimethylsilyloxymethyl-6-methyl-phenoxyacetate: A solution of 1.96 g (7.3 mmol) of 2-tert-butyl-dimethylsilyloxymethyl-6-methyl phenol in 5 mL of dimethylformamide was treated with 2.1 g (15.4 mmol) of potassium carbonate and 850 μL (7.3 mmol) of ethyl bromoacetate. The resulting solution was heated at 70° C. for 4 h. After cooling to room temperature, the reaction mixture was partitioned between ethyl acetate and 3N hydrogen chloride. The combined organic layer was washed with diluted brine, dried over magnesium sulfate, filtered, and evaporated in vacuo. Silica gel chromatography using 5% ethyl acetate:hexanes gave 2.13 g (83%) of desired compound as a light yellow oil. $^1$H NMR (CDCl$_3$): 0.12 (s, 6H), 0.93 (s,9H), 1.33 (t, J=6.3 Hz, 3H), 2.31 (s, 3H), 4.30 (q, J=6.3 Hz, 2H), 4.49 (s, 2H), 4.79 (s, 2H), 7.06 (t, J=7.5 Hz, 1H), 7.10 (d, J=7.5 Hz, 1H), 7.27 (d, J=7.5 Hz, 1H). Mass spectrum: (M+H)$^+$=339.

D. 2-Tert-butyl-dimethylsilyloxymethyl-6-methyl-phenoxyacetic Acid: To a solution of 2.13 g (6.4 mmol) of ethyl 2-tert-butyl-dimethylsilyloxymethyl-6-methyl-phenoxyacetate in 20 mL of methanol was added 4.3 mL of 3N sodium hydroxide. After the reaction mixture was stirred at room temperature for 30 min, it was acidified with 3N HCl and partitioned between water and methylene chloride. The combined organic extracts were washed with brine and dried over anhydrous sodium sulfate, filtered and evaporated to dryness under reduced pressure to give 1.93 g (97%) of 2-tert-butyl-dimethylsilyloxymethyl-6-methyl-phenoxyacetic acid as a white solid. $^1$H NMR (CDCl$_3$): 0.12 (s, 6H), 0.92 (s, 9H), 2.32 (s, 3H), 4.58 (s, 2H), 4.78 (s, 2H), 7.05 (t, J=7.5 Hz, 1H), 7.13 (d, J=7.5 Hz, 1H), 7.16 (d, J=7.5 Hz, 1H), 11.6 (bs, 1H). Mass spectrum: (M+H)$^+$=311.

E. 5-(2-Tert-butyl-dimethylsilyloxymethyl-6-methyl-phenoxyacetyl)amino-2-((3R,3aS,6aR)-bis-tetrahydrofuran-3-yl-oxycarbonyl)amino-1,6-diphenyl-3-hydroxyhexane: To a solution of 100 mg (0.23 mmol) of 2-((3R,3aS,6aR)-bis-tetrahydrofuran-3-yl-oxycarbonyl)amino-3-hydroxy-5-amino-1,6-diphenylhexane in 1 mL of THF and 1 mL of methylene chloride was subsequently added 70.4 mg (0.23 mmol) of 2-tert-butyl-dimethylsilyloxymethyl-6-methyl-phenoxyacetic acid, 44 mg (0.23 mmol) of EDIC, 3.1 mg (0.023 mmol) of HOBT, and 63 μL (0.46 mmol) of triethyl amine. The resulting solution was allowed to stir at ambient temperature for 6 h, and concentrated in vacuo. The residue was taken up in ethyl acetate, washed with one portion of 3N HCl solution, one portion of 10% aqueous NaHCO$_3$, and one portion of saturated brine, dried over MgSO$_4$, and concentrated in vacuo. The resulting product mixture was purified by silica gel chromatography using 50% ethyl acetate:hexanes as an eluent to provide 135 mg (80%) of the desired compound. $^1$H NMR (CDCl$_3$) δ 0.06 (s, 3H), 0.07 (s, 3H), 0.91 (s, 9H), 1.63 (dd, J=7.5, 3.0 Hz, 1H), 1.68 (dd, J=7.5, 1.5 Hz, 1H), 1.79 (m, 2H), 2.10 (s, 3H), 2.89 (m, 3H), 2.96 (m, 1H), 3.73 (m, 4H), 3.79 (dd, J=15.0, 7.5 Hz, 1H), 3.88 (dq, J=15.6, 7.5 Hz, 2H), 4.01 (dd, J=6.0, 9.0 Hz, 1H), 4.26 (AB, J=15.0 Hz, 2H), 4.27 (m, 1H), 4.62 (s, 2H), 5.06 (m, 2H), 5.68 (d, J=6.0 Hz, 1H), 7.08 (m, 3H), 7.15–7.32 (m, 11H). Mass spectrum: (M+H)$^+$=733.

F. 5-(2-Hydroxymethyl-6-Methyl-phenoxyacetyl)amino-2-((3R,3aS,6aR)-bis-tetrahydrofuran-3-yl-oxycarbonyl)amino-1,6-diphenyl-3-hydroxyhexane: To a solution of 135 mg (0.18 mmol) of 5-(2-tert-butyl-dimethylsilyloxymethyl-6-methyl-phenoxyacetyl)amino-2-((3R,3aS,6aR)-bis-tetrahydrofuran-3-yl-oxycarbonyl)amino-1,6-diphenyl-3-hydroxyhexane in 1.5 mL of THF was added 370 μL of 1N tetra-butylammonium fluoride in THF. After the reaction mixture was stirred at room temperature for 2 h, it was partitioned between water and ethyl acetate. The combined organic extracts were washed with brine and dried over anhydrous sodium sulfate, filtered and evaporated to dryness under reduced pressure. The desired compound was purified by silica gel chromatography using 50% ethyl acetate:hexanes as an eluent to provide 135 mg (80%) of 5-(2-hydroxymethyl-6-methyl-phenoxyacetyl)amino-2-((3R,3aS,6aR)-bis-tetrahydrofuran-3-yl-oxycarbonyl)amino-1,6-diphenyl-3-hydroxyhexane as a white solid. $^1$H NMR (CDCl$_3$) δ 1.71 (m, 2H), 1.80 (m, 2H), 2.19 (s, 3H), 2.87–2.97 (m, 6H), 3.75 (m, 2H), 3.82 (m, 2H), 3.88 (m, 2H), 4.01 (dd, J=9.6, 6.0 Hz, 1H), 4.31 (AB, J=15.0 Hz, 2H), 4.32 (m, 1H), 4.49 (m, 2H), 5.08 (m, 2H), 5.68 (d, J=5.4 Hz, 1H), 7.05 (m, 1H), 7.18 (m, 3H), 7.21–7.32 (m, 10H). Mass spectrum: (M+H)$^+$=619.

EXAMPLE 8

(2S,3S,5S)-5-(4,6-Dimethyl-pyrimidinyl-5-oxyacetyl)amino-2-((3R,3aS,6aR)-bis-tetrahydrofuran-3-yl-oxycarbonyl)amino-1,6-diphenyl-3-hydroxyhexane To a solution of 100 mg (0.23 mmol) of 2-((3R,3aS,6aR)-bis-tetrahydrofuran-3-yl-oxycarbonyl)amino-3-hydroxy-5-amino-1,6-diphenylhexane in 1 mL of THF and 1 mL of methylene chloride was subsequently added 38 mg (0.23 mmol) of 4,6-dimethyl pyrimidin-5-oxy-acetic acid, 44 mg (0.23 mmol) of EDIC, 3.1 mg (0.023 mmol) of HOBT, and 63 μL (0.46 mmol) of triethyl amine. The resulting solution was allowed to stir at ambient temperature for 6 h, and concentrated in vacuo. The residue was taken up in ethyl acetate, washed with one portion of 10% aqueous NaHCO$_3$, and one portion of saturated brine, dried over MgSO$_4$, and concentrated in vacuo. The resulting product mixture was purified by silica gel chromatography using 2.5% methanol:chloroform as an eluent to provide 100 mg (79%) of the desired compound. $^1$H NMR (CDCl$_3$) δ 1.65 (m, 2H), 1.81 (t, J=9.0 Hz, 2H), 2.32 (s, 6H), 2.80–3.02 (m, 6H), 3.76 (t, J=9.6 Hz, 2H), 3.77 (dd, J=12.6, 9.0 Hz, 1H), 3.88 (m, 1H), 3.91(dt, J=3.0, 7.5 Hz, 1H), 4.00 (dd, J=12.3, 6.0 Hz, 1H), 4.09 (d, J=15.0 Hz, 1H), 4.28 (d, J=15.0 Hz, 1H), 4.35 (q, J=6.3 Hz, 1H), 5.08 (m, 2 H), 5.68 (d,J=5.4 Hz, 1H), 6.77 (d, J=7.5 Hz, 1H), 7.15–7.32 (m, 10H), 8.74 (s, 1H). Mass spectrum: (M+H)$^+$=605.

EXAMPLE 9

(2S,3S,5S)-5-(N-(2,6-Dimethyl-phenyl)aminoacetyl)amino-2-((3R,3aS,6aR)-bis-tetrahydrofuran-3-yl-oxycarbonyl)amino-1,6-diphenyl-3-hydroxyhexane A. N-(2,6-Dimethyl-phenyl)amino Acetic Acid: To a solution of 6.05 g (0.05 mol) of 2,6-dimethyaniline in 70 mL of DMF was added 8 mL (0.05 mol) of benzyl bromoacetate. The reaction mixture was heated at 50° C. for 1 h. After cooling to room temperature, the solvent was removed under reduced pressure. The desired compound was purified by silica gel chromatography using 20% ethyl acetate:hexanes as an eluent to provide 6.1 g (60%) of benzyl N-(2,6-dimethyl-phenyl)amino acetate as a light yellow oil. $^1$H NMR (CDCl$_3$) δ 2.31 (s, 6H), 3.87 (s, 2H), 5.18 (s, 2H), 6.81 (t, J=8.2 Hz, 1H), 6.97 (d, J=8.2 Hz, 2H), 7.35 (m, 5H). Mass spectrum: (M+H)$^+$=270.

To a solution of 6.1 g (0.02 mol) of benzyl N-(2,6-dimethyl-phenyl)amino acetate in 50 mL of methanol was added 300 mg of Pd/C(10%). The reaction mixture was stirred under 1 atomsphere of hydrogen for 12 h. The Pd/C was removed over a celite pad, and the solvent was evaporated to dryness under reduced pressure. The residue was added 1:1 mixture of ethyl acetate and hexanes, the desired compound was percipitated out to give 3.1 g (76%) of desired product as a white solid. $^1$H NMR (d$_6$-DMSO) δ 2.32 (s, 6H), 3.95 (s, 2H), 6.94 (t, J=7.5 Hz, 1H), 7.04 (d, J=7.5 Hz, 2H), 8.07 (bs, 1H), 11.7 (bs, 1H). Mass spectrum: (M+H)$^{+=}$180.

B. 2-(N-(2,6-Dimethyl-phenyl)amino-acetylamino-3-hydroxy 5-(t-butyloxycarbonylamino)-1,6-diphenylhexane: To a solution of 214 mg (0.56 mmol) of (2S,3S,5S)-2-amino-3-hydroxy-5-(t-butyloxycarbonylamino)-1,6-diphenylhexane in 2.5 mL of THF and 2.5 mL of methylene chloride was subsequently added 100 mg (0.56 mmol) of N-(2,6-dimethyl-phenyl)amino acetic acid, 107 mg (0.56 mmol) of EDIC, 7.5 mg (0.05 mmol) of HOBT, and 160 μL (1.12 mmol) of triethyl amine. The resulting solution was allowed to stir at ambient temperature for 6 h, and concentrated in vacuo. The residue was taken up in ethyl acetate, washed with one portion of 10% aqueous NaHCO$_3$, and one portion of saturated brine, dried over MgSO$_4$, and concentrated in vacuo. The resulting product mixture was purified by silica gel chromatography using 40% ethyl acetate:hexanes as an eluent to provide 245 mg (80%) of the desired compound. $^1$H NMR (CDCl$_3$) δ 1.40 (s, 9H), 1.60 (m, 2H), 2.21 (s, 6H), 2.72 (m, 1H), 2.74 (dd, J=8.4, 6.0 Hz, 2H), 2.93 (d, J=7.5 Hz, 2H), 3.54 (s, 2H), 3.72 (m, 1H), 3.86 (m, 1H), 4.10 (q, J=6.3 Hz, 1H), 4.57 (m, 1H), 6.86 (d, J=7.5 Hz, 2H), 6.98 (d, J=7.5 Hz, 2H), 7.12 (d, J=7.5 Hz, 2H), 7.15–7.32 (m, 10H), 8.74 (s, 1H). Mass spectrum: (M+H)$^+$=546.

C. 2-(N-(2,6-Dimethyl-phenyl)amino acetyl)amino-3-hydroxy-5-amino-1,6-diphenylhexane: To a solution of 245 mg (0.45 mmol) of 2-(N-(2,6-dimethyl-phenyl)amino acetyl)amino-3-hydroxy-5-(t-butyloxycarbonylamino)-1,6-diphenylhexane in 3 mL of dichloromethane was added 400 μL of trifluoroacetic acid. After the reaction was finished as indicated by TLC, the solvent was removed under reduced pressure. The residue was dissolved in methylene chloride and washed with saturated aqueous NaHCO$_3$ and saturated brine. The combined organic layer was dried over Na$_2$SO$_4$ and concentrated in vacuo to give 138 mg (68%) of product as a white solid. The product was used without further purification. $^1$H NMR (CDCl$_3$) δ 0.89 (t, J=6.0 Hz, 1H), 1.30 (m, 2H), 1.53 (dt, J=15.0, 1.0 Hz, 1H), 2.28 (s, 6H), 2.41 (dd, J=13.2, 8.4 Hz, 1H), 2.77 (dd, J=13.5, 5.4 Hz, 1H), 2.93 (dd, J=9.0, 3.0 Hz, 2H), 3.03 (m, 1H), 3.65 (s, 2H), 3.86 (d, J=10.2 Hz, 1H), 4.12 (q, J=8.7 Hz, 1H), 6.85 (d, J=7.5 Hz, 1H), 7.01 (d, J=7.5 Hz, 2H), 7.09 (d, J=7.5 Hz, 2H), 7.18–7.32 (m, 10H). Mass spectrum: (M+H)$^+$=446.

D. 5-(N-(2,6-Dimethyl-phenyl)amino acetyl)amino-2-((3R,3aS,6aR)-bis-tetrahydrofuran-3-yl-oxycarbonyl)amino-1,6-diphenyl-3-hydroxyhexane: To a solution of 66 mg (0.22 mmol) of ((3R,3aS,6aR)-bis-tetrahydrofuran-3-yl-oxycarbonyl)oxy-4-nitro benzene in 3 mL of 1,2-dichloroethane was added 100 mg (0.22 mmol) of 2-(N-(2,6-Dimethyl-phenyl)amino acetyl)amino-3-hydroxy-5-amino-1,6-diphenylhexane. The resulting solution was refluxed for 12 h. After washing with three portions of 10% aqueous NaHCO$_3$ and one portion of saturated brine, the solution was dried over Na$_2$SO$_4$ and concentrated in vacuo. The residue was purified by silica gel chromatography by eluting with 50-80% of ethyl acetate:hexanes to provide 90 mg (68%) of the desired compound. $^1$H NMR (CDCl$_3$) δ 1.58–1.75 (m, 4H), 2.21 (s, 6H), 2.78 (dd, J=7.8, 3.6 Hz, 2H), 2.95 (d, J=7.5 Hz, 2H), 2.99 (m, 1H), 3.57 (s, 2H), 3.72 (m, 2H), 3.78 (m, 1H), 3.88 (dt, J=7.8, 3.0 Hz, 1H), 3.98 (m, 2H), 4.12 (q, J=7.5 Hz, 1H), 4.92 (q, J=7.5 Hz, 1H), 5.08 (q, J=7.8 Hz, 1H), 5.68 (d, J=5.4 Hz, 1H), 6.87 (t, J=7.5 Hz, 1H), 6.99 (d, J=7.5 Hz, 2H), 7.12 (d, J=7.5 Hz, 2H), 7.18–7.32 (m, 10H). Mass spectrum: (M+NH$_4$)$^+$=602.

EXAMPLE 10

(2S,3S,5S)-5-(2,6-Dimethyl-pyridin-3-yl-oxyacetyl) amino-2-((3R,3aS,6aR)-bis-tetrahydrofuran-3-yl-oxycarbonyl)amino-1,6-diphenyl-3-hydroxyhexane To a solution of 100 mg (0.23 mmol) of 2-((3R,3aS,6aR)-bis-tetrahydrofuran-3-yl-oxycarbonyl)amino-3-hydroxy-5-amino-1,6-diphenylhexane in 1 mL of THF and 1 mL of methylene chloride was subsequently added 41 mg (0.23 mmol) of 4,6-dimethyl pyridin-3-oxy acetic acid, 44 mg (0.23 mmol) of EDIC, 3.1 mg (0.023 mmol) of HOBT, and 63 μL (0.46 mmol) of triethyl amine. The resulting solution was allowed to stir at ambient temperature for 6 h, and concentrated in vacuo. The residue was taken up in ethyl acetate, washed with one portion of 10% aqueous NaHCO$_3$, and one portion of saturated brine, dried over MgSO$_4$, and concentrated in vacuo. The resulting product mixture was purified by silica gel chromatography using 5% methanol:chloroform as an eluent to provide 106 mg (76%) of the desired compound. $^1$H NMR (CDCl$_3$) δ 1.65 (m, 3H), 1.82 (m, 1H), 2.01 (s, 3H), 2.34 (s, 3H), 2.80–3.02 (m, 6H), 3.61 (m, 1H), 3.75 (dd, J=9.6 Hz, 2H), 3.80 (m, 1H), 3.90 (dt, J=7.5, 2.0 Hz, 2H), 4.00 (dd, J=9.0, 6.0 Hz, 1H), 4.08 (d, J=15.0 Hz, 1H), 4.26 (d, J=15.0 Hz, 1H), 4.33 (m, 1H), 5.07 (m, 2 H), 5.68 (d, J=4.5 Hz, 1H), 6.86 (d, J=7.5 Hz, 1H), 6.96 (d, J=4.5 Hz, 1H), 7.12–7.35 (m, 10H), 8.16 (d, J=4.5 Hz, 1H). Mass spectrum: (M+H)$^+$=604.

EXAMPLE 11

(2S,3S,5S)-5-(2,4,6-Trimethyl-phenoxyacetyl) amino-2-((3R,3aS,6aR)-bis-tetrahydrofuran-3-yl-oxycarbonyl)amino-1,6-diphenyl-3-hydroxyhexane To a solution of 100 mg (0.23 mmol) of 2-((3R,3aS,6aR)-bis-tetrahydrofuran-3-yl-oxycarbonyl)amino-3-hydroxy-5-amino-1,6-diphenylhexane in 1 mL of THF and 1 mL of methylene chloride was subsequently added 44 mg (0.23 mmol) of 2,4,6-trimethylphenyloxy acetic acid, 44 mg (0.23 mmol) of EDIC, 3.1 mg (0.023 mmol) of HOBT, and 63 μL (0.46 mmol) of triethyl amine. The resulting solution was allowed to stir at ambient temperature for 6 h, and concentrated in vacuo. The residue was taken up in ethyl acetate, washed with one portion of 3N HCl, one portion of 10% aqueous NaHCO$_3$, and one portion of saturated brine, dried over MgSO$_4$, and concentrated in vacuo. The resulting product mixture was purified by silica gel chromatography using 5% methanol:chloroform as an eluent to provide 91 mg (78%) of the desired compound. $^1$H NMR (CDCl$_3$) δ 1.68 (m, 2H), 1.79 (m, 2H), 2.07 (s, 6H), 2.23 (s, 3H), 2.80–3.00 (m, 6H), 3.73 (dd, J=6.0, 2.8 Hz, 1H), 3.76 (m, 2H), 3.88 (m, 2H), 3.90 (m, 1H), 4.02 (dd, J=12.3, 6.6 Hz, 1H), 4.06 (d, J=15.0 Hz, 1H), 4.22 (d, J=15.0 Hz, 1H), 4.29 (m, 1H), 5.08 (m, 2H), 5.68 (d, J=5.7 Hz, 1H), 6.80 (s, 2H), 6.97 (d, J=7.5 Hz, 1H), 7.12–7.30 (m, 10H). Mass spectrum: (M+H)$^+$=617.

EXAMPLE 12

(2S,3S,5S)-5-(2-Methoxy-6-methylphenoxyacetyl) amino-2-((3R,3aS,6aR)-bis-tetrahydrofuran-3-yl-oxycarbonyl)amino-1,6-diphenyl-3-hydroxyhexane A. Ethyl 2-Methoxyl-6-methyl-phenoxyacetate: A solution of 5.0 g (36.2 mmol) of 2-methoxyl-6-methyl phenol in 44 mL of dimethylformamide was treated with 10 g (72.5 mmol) of potassium carbonate and 4.2 mL (38.0 mmol) of ethyl bromoacetate. The resulting solution was heated at 70° C. for 4 h. After cooling to room temperature, the reaction mixture was partitioned between ethyl acetate and 3N hydrogen chloride. The combined organic layer was washed with diluted brine, dried over magnesium sulfate, filtered, and evaporated in vacuo. Silica gel chromatography using 5% ethyl acetate:hexanes gave 6.0 g (74%) of desired compound as a light yellow oil. $^1$H NMR (CDCl$_3$): 1.32 (t, J=7.5 Hz, 3H), 2.33 (s, 3H), 3.82 (s, 3H), 4.27 (q, J=7.5 Hz, 2H), 4.61 (s, 2H), 6.75 (d, J=7.5 Hz, 1H), 6.77 (d, J=7.5 Hz, 1H), 6.95 (t, J=7.5 Hz, 1H). Mass spectrum: (M+H)$^+$=225.

B. 2-Methoxyl-6-methyl-phenoxyacetic Acid: To a solution of 5.6 g (25 mmol) of ethyl 2-methoxyl-6-methyl-phenoxyacetate in 20 mL of methanol was added 16.6 mL of 3N sodium hydroxide. After the reaction mixture was stirred at room temperature for 30 min, it was acidified with 3N HCl and partitioned between water and methylene chloride. The combined organic extracts were washed with brine and dried over anhydrous sodium sulfate, filtered and evaporated to dryness under reduced pressure to give 4.4 g (90%) of desired acid as a white solid. $^1$H NMR (CDCl$_3$): 2.25 (s, 3H), 3.80 (s, 3H), 4.51 (s, 2H), 6.73 (d, J=7.5 Hz, 1H), 6.82 (d, J=7.5 Hz, 1H), 6.93 (t, J=7.5 Hz, 1H). Mass spectrum: (M+NH$_4$)$^+$=214.

C. 5-(2-Methoxyl-6-methyl-phenoxyacetyl)amino-2-((3R,3aS,6aR)-bis-Tetrahydrofuran-3-yl-oxycarbonyl)amino-1,6-diphenyl-3-hydroxyhexane: To a solution of 80 mg (0.18 mmol) of 2-((3R,3aS,6aR)-bis-tetrahydrofuran-3-yl-oxycarbonyl)amino-3-hydroxy-5-amino-1,6-diphenylhexane in 1 mL of THF and 1 mL of methylene chloride was subsequently added 35 mg (0.18 mmol) of 2-methoxyl-6-methyl-phenoxyacetic acid, 35 mg (0.18 mmol) of EDIC, 3 mg (0.02 mmol) of HOBT, and 53 µL (0.38 mmol) of triethyl amine. The resulting solution was allowed to stir at ambient temperature for 6 h, and concentrated in vacuo. The residue was taken up in ethyl acetate, washed with one portion of 3N HCl solution, one portion of 10% aqueous NaHCO$_3$, and one portion of saturated brine, dried over MgSO$_4$, and concentrated in vacuo. The resulting product mixture was purified by silica gel chromatography using 50% ethyl acetate:hexanes as an eluent to provide 94 mg (85%) of the desired compound. $^1$H NMR (CDCl$_3$) δ 1.65 (m, 2H), 1.76 (m, 2H), 2.18 (s, 3H), 2.88 (m, 4H), 2.95 (m, 1H), 3.15 (m, 1H), 3.73 (s, 3H), 3.75 (m, 2H), 3.80 (t, J=7.5 Hz, 1H), 3.89 (dt, J=8.7, 3 Hz, 1H), 4.01 (dd, J=6.0, 9.0 Hz, 1H), 4.27 (m, 1H), 4.35 (AB, J=15.0 Hz, 2H), 5.07 (m, 2H), 5.78 (t, J=7.5 Hz, 2H), 7.00 (t, J=7.5 Hz, 1H), 7.15–7.30 (m, 10H), 7.41 (d, J=8.7 Hz, 1H). Mass spectrum: (M+H)$^+$=619.

EXAMPLE 13

(2S,3S,5S)-5-(N-(2,6-Dimethyl-phenyl)-N-methyl-aminoacetyl)amino-2-((3R,3aS,6aR)-bis-tetrahydrofuran-3-yl-oxycarbonyl)amino-1,6-diphenyl-3-hydroxyhexane A. N-(2,6-Dimethyl-phenyl)-N-Methyl-amino Acetic Acid: To a solution of 2.0 g (7.43 mmol) of benzyl N-(2,6-dimethyl-phenyl)amino acetate in 20 mL of DMF was added 1.85 mL (29.7 mmol) of methyl iodide and 2.6 mL (14.9 mmol) of Hünig's base. The reaction mixture was heated at 60° C. for 24 h. After cooling to room temperature, the reaction mixture was partitioned between ethyl acetate and saturated sodium bicarbonate. The extracts was washed with water and brine, dried over sodium sulfate and the solvent was removed under reduced pressure. The desired compound was purified by passage over a short silica gel column to provide 1.65 g (78%) of benzyl N-(2,6-dimethyl-phenyl)-N-methylamino acetate as a light yellow oil. $^1$H NMR (CDCl$_3$) δ 2.31 (s, 6H), 2.86 (s, 3H), 3.83 (s, 2H), 5.17 (s, 2H), 6.98 (m, 3H), 7.36 (m, 5H). Mass spectrum: (M+H)$^+$=284.

To a solution of 1.65 g (5.8 mol) of benzyl N-(2,6-dimethyl-phenyl)-N-methylamino acetate in 50 mL of methanol was added 1 mL of 3N sodium hydroxide. After the reaction mixture was stirred at room temperature for 30 min, it was acidified with 3N HCl to pH=4 and partitioned between water and methylene chloride. The combined organic extracts were washed with brine and dried over anhydrous sodium sulfate, filtered and evaporated to dryness under reduced pressure to give 0.75 g (67%) of N-(2,6-dimethyl-phenyl)-N-methylamino acetic acid as a light yellow solid. $^1$H NMR (CD$_3$OD): 2.32 (s, 6H), 2.84(s, 3H), 3.73 (s, 2H), 6.95 (m, 3H). Mass spectrum: (M+H)$^+$=194.

B. 5-(N-(2,6-Dimethyl-phenyl)-N-methyl-amino acetyl)amino-2-((3R,3aS,6aR)-bis-tetrahydrofuran-3-yl-oxycarbonyl)amino-1,6-diphenyl-3-hydroxyhexane: To a solution of 100 mg (0.23 mmol) of 2-((3R,3aS,6aR)-bis-tetrahydrofuran-3-yl-oxycarbonyl)amino-3-hydroxy-5-amino-1,6-diphenylhexane in 1 mL of THF and 1 mL of methylene chloride was subsequently added 44 mg (0.23 mmol) of N-(2,6-dimethyl-phenyl)-N-methylamino acetic acid, 44 mg (0.23 mmol) of EDIC, 3.1 mg (0.023 mmol) of HOBT, and 63 µL (0.46 mmol) of triethyl amine. The resulting solution was allowed to stir at ambient temperature for 6 h, and concentrated in vacuo. The residue was taken up in ethyl acetate, washed with one portion of 3N HCl, one portion of 10% aqueous NaHCO$_3$, and one portion of saturated brine, dried over MgSO$_4$, and concentrated in vacuo. The resulting product mixture was purified by silica gel chromatography using 5% methanol:chloroform as an eluent to provide 88 mg (62%) of the desired compound. $^1$H NMR (CDCl$_3$) δ 1.64 (m, 2H), 1.75 (m, 2H), 2.23 (s, 3H), 2.28 (s, 3H), 2.75–3.00 (m, 6H), 3.56 (s, 2H), 3.72 (dd, J=9.0, 6.0 Hz, 2H), 3.76 (m, 1H), 3.82 (dd, J=12.6, 7.5 Hz, 1H), 3.88 (dt, J=7.5, 3.0 Hz, 1H), 3.99 (dd, J=8.7, 6.0 Hz, 1H), 4.22 (m, 1H), 5.07 (m, 2H), 5.67 (d, J=5.4 Hz, 1H), 7.01 (s, 3H), 7.15–7.30 (m, 10H), 7.54 (d, J=7.5 Hz, 1H). Mass spectrum: (M+H)$^+$=616.

EXAMPLE 14

(2S,3S,5S)-5-(2,6-Dimethyl-4-fluoro-phenoxyacetyl)amino-2-((3R,3aS,6aR)-bis-tetrahydrofuran-3-yl-oxycarbonyl)amino-1,6-diphenyl-3-hydroxyhexane A. 2,6-Dimethyl-4-fluoro-phenoxy Acetic Acid: To a solution of 553 mg (2.5 mmol) of ethyl 4-amino-2,6-dimethyl-phenoxyacetate in 2 mL of methylene chloride cooled at −15° C. was added 309 mg (3.0 mmol) and 460 µL (3.75 mmol) of boron trifluoride diethyl etherate. The reaction was allowed to stir at −15° C. for 10 min and then at room temperature for 20 min. The solvent was evaporated to a small volume, and added dropwise into ether. The dark brown solid was collected by filtration, and dried under vacuum. Toluene (10 mL) was added to the residue and refluxed for 3 h. After cooling to room temperature, the reaction mixture was partitioned between ether and water, dried over MgSO$_4$, filter and evaporated to dryness to give 318 mg (56%) of ethyl 2,6-dimethyl-4-fluoro-phenoxy acetate as a yellow oil. $^1$H NMR (CDCl$_3$): 1.33 (t, J=7.5 Hz, 3H), 2.29 (s, 6H), 4.30 (q, J=7.5 Hz, 2H), 4.37 (s, 2H), 6.70 (d, J=9.0 Hz, 2H). Mass spectrum: (M+NH$_4$)$^+$=244.

To a solution of 318 mg (5.8 mmol) of ethyl 2,6-dimethyl-4-fluoro-phenoxyacetate in 50 mL of methanol was added 1 mL of 3N sodium hydroxide. After the reaction mixture was stirred at room temperature for 30 min, it was acidified with 3N HCl to pH=4 and partitioned between water and methylene chloride. The combined organic extracts were washed with brine and dried over anhydrous sodium sulfate, filtered and evaporated to dryness under reduced pressure to give 248 mg (90%) of 2,6-dimethyl-4-fluoro-phenoxy acetic acid as a white solid.

B. 5-(2,6-Dimethyl-4-fluoro-phenoxyacetyl)amino-2-((3R,3aS,6aR)-bis-tetrahydrofuran-3-yl-oxycarbonyl)amino-1,6-diphenyl-3-hydroxyhexane: To a solution of 100 mg (0.23 mmol) of 2-((3R,3aS,6aR)-bis-tetrahydrofuran-3-yl-oxycarbonyl)amino-3-hydroxy-5-amino-1,6-diphenylhexane in 1 mL of THF and 1 mL of methylene chloride was subsequent added 45 mg (0.23 mmol) of 2,6-dimethyl-4-fluoro-phenoxy acetic acid, 44 mg (0.23 mmol) of EDIC, 3.1 mg (0.023 mmol) of HOBT, and 63 µL (0.46 mmol) of triethyl amine. The resulting solution was allowed to stir at ambient temperature for 6 h, and concentrated in vacuo. The residue was taken up in ethyl acetate, washed with one portion of 3N HCl, one portion of 10% aqueous $NaHCO_3$, and one portion of saturated brine, dried over $MgSO_4$, and concentrated in vacuo. The resulting product mixture was purified by silica gel chromatography using 80% ethyl acetate:hexanes as an eluent to provide 32 mg (23%) of the desired compound. $^1$H NMR ($CDCl_3$) δ 1.68 (m, 2H), 1.80 (m, 2H), 2.08 (s, 6H), 2.72–3.01 (m, 5H), 3.77 (m, 4H), 3.88 (m, 3H), 4.01 (dd, J=9.0, 6.0 Hz, 1H), 4.03 (d, J=15.0 Hz, 1H), 4.20 (d, J=15.0 Hz, 1H), 4.30 (m, 1H), 5.08 (m, 2H), 5.69 (d, J=5.4 Hz, 1H), 6.70 (d, J=9.0 Hz, 1H), 6.90 (d, J=6.3 Hz, 1H), 7.15–7.32 (m, 10H). Mass spectrum: $(M+H)^+$=621.

EXAMPLE 15

(2S,3S,5S)-5-(2,6-Dimethyl-4-fluoro-phenoxyacetyl)amino-2-((3R,3aS,6aR)-bis-tetrahydrofuran-3-yl-oxycarbonyl)amino-1,6-diphenyl-3-hydroxyhexane A. 2,6-Dimethyl-4-N, N-dimethylamino-phenoxy Acetic Acid: To a solution of 440 mg (2.0 mmol) of ethyl 4-amino-2,6-dimethyl-phenoxyacetate in 2 mL of DMF was added 150 µL (2.4 mmol) of methyl iodide and 690 µL (3.9 mmol) of Hunig's base. The reaction was allowed to stir at room temperature for 3 h. The solvent was evaporated, the resulting product mixture was purified by silica gel chromatography using 10% ethyl acetate:hexanes as an eluent to provide 194 mg (39%) of ethyl 2,6-dimethyl-4-N-methylamino-phenoxy acetate and 125 mg (27%) of ethyl 2,6-dimethyl-4-N,N-dimethylamino-phenoxy acetate. $^1$H NMR ($CDCl_3$) for ethyl 2,6-dimethyl-4-N-methylamino-phenoxy acetate: 1.33 (t, J=7.5 Hz, 3H), 2.28 (s, 6H), 2.89 (s, 6H), 4.30 (q, J=7.5 Hz, 2H), 4.34 (s, 2H), 6.40 (s, 2H). Mass spectrum: $(M+NH_4)^+$=252.

To a solution of 318 mg (5.8 mmol) of eTo a solution of 194 mg (0.77 mmol) of ethyl 2,6-dimethyl-4-fluoro-phenoxyacetate in 2 mL of methanol was added 1 mL of 3N sodium hydroxide. After the reaction mixture was stirred at room temperature for 30 min, it was acidified with 3N HCl to pH=4 and partitioned between water and methylene chloride. The combined organic extracts were washed with brine and dried over anhydrous sodium sulfate, filtered and evaporated to dryness under reduced pressure to give 147 mg (86%) of 2,6-Dimethyl-4N,N-Dimethylamino-phenoxy acetic acid as a white solid. $^1$H NMR ($CD_3OD$): 2.03 (s, 6H), 2.87 (s, 6H), 4.32 (s, 2H), 6.53 (s, 2H). Mass spectrum: $(M+H)^{+-}$224.

B. 5-(2,6-Dimethyl-4-N, N-dimethylamino-phenoxyacetyl)amino-2-((3R,3aS,6aR)-bis-tetrahydrofuran-3-yl-oxycarbonyl)amino-1,6-diphenyl-3-hydroxyhexane: To a solution of 100 mg (0.23 mmol) of 2-((3R,3aS,6aR)-bis-tetrahydrofuran-3-yl-oxycarbonyl)amino-3-hydroxy-5-amino-1,6-diphenylhexane in 1 mL of THF and 1 mL of methylene chloride was subsequently added 51 mg (0.23 mmol) of 2,6-dimethyl-4-N,N-dimethylamino-phenoxy acetic acid, 44 mg (0.23 mmol) of EDIC, 3.1 mg (0.023 mmol) of HOBT, and 63 µL (0.46 mmol) of triethylamine. The resulting solution was allowed to stir at ambient temperature for 6 h, and concentrated in vacuo. The residue was taken up in ethyl acetate, washed with one portion of 3N HCl, one portion of 10% aqueous $NaHCO_3$, and one portion of saturated brine, dried over $MgSO_4$, and concentrated in vacuo. The resulting product mixture was purified by silica gel chromatography using 2.5% methanol:chloroform as an eluent to provide 66 mg (45%) of the desired compound. $^1$H NMR ($CDCl_3$) δ 1.68 (m, 2H), 1.79 (m, 2H), 2.08 (s, 6H), 2.88 (s, 6H), 2.70–3.00 (m, 6H), 3.73 (dd, J=6.0, 3.0 Hz, 2H), 3.77 (dd, J=6.6, 3.0 Hz, 1H), 3.82 (d, J=6.3 Hz, 1H), 3.89 (dq, J=7.5, 3.0 Hz, 2H), 4.01 (dd, J=6.0, 9.0 Hz, 1H), 4.03 (d, J=15.0 Hz, 1H), 4.20 (d, J=15.0 Hz, 1H), , 4.28 (m, 1H), 5.08 (t, J=8.4 Hz, 1H), 5.10 (m, 1H), 5.69 (d, J=5.4 Hz, 1H), 6.48 (s, 2H), 6.99 (d, J=7.5 Hz, 1H), 7.5–7.32 (m, 10H). Mass spectrum: $(M+H)^+$=646.

EXAMPLE 16

(2S ,3S ,5S)-5-(2.6-Dimethyl-3-amino-phenoxyacetyl)amino-2-((3R,3aS,6aR)-bis-tetrahydrofuran-3-yl-oxycarbonyl)amino-1,6-diphenyl-3-hydroxyhexane A. Ethyl 2,6-Dimethyl-3-nitro-phenoxyacetate: A solution of 0.25 g (1.5 mmol) of 2,6-dimethyl-3-nitro aniline in 0.8 mL of water, 0.5 mL of concentrated sulfric acid, and 1 g of ice was stirred at 0° C. to homogenous. To the above solution was added 150 mg of sodium nitrite in 300 µL of water. The reaction was kept at 0° C. for 20 min, then added dropwise to a boiled solution of 1 mL of sulfric acid and 750 mL of water. Boiling was continued for 20 min after addition. The solution was then partitioned between ether and water. The organic extracts was washed with brine, dried over $MgSO_4$, filtered and evaporated under reduced pressure. The desired compound was purified by silica gel chromatograph eluted with 20% ethyl acetate:hexanes to yield 155 mg (62%) of 2,6-dimethyl-3-nitro-phneol as a yellow solid. $^1$H NMR ($CDCl_3$): 2.32 (s, 3H), 2.42 (s, 3H), 4.96 (s, 1H), 7.08 (d, J=8.4 Hz, 1H), 7.42 (d, J=8.4 Hz, 1H). Mass spectrum: $(M+NH_4)^+$=185.

A solution of 155 mg (0.93 mmol) of 2,6-dimethyl-3-nitro-phenol in 5 mL of dimethylformamide was treated with 384 mg (2.78 mmol) of potassium carbonate and 124 µL (1.11 mmol) of ethyl bromoacetate. The resulting solution was heated at 70° C. for 4 h. After cooling to room temperature, the reaction mixture was partitioned between ethyl acetate and 3N hydrogen chloride. The combined organic layer was washed with diluted brine, dried over magnesium sulfate, filtered, and evaporated in vacuo. Silica gel chromatography using 10% ethyl acetate:hexanes gave 200 mg (85%) of ethyl 2,6-dimethyl-3-nitrophenoxyl acetate as a light yellow oil. $^1$H NMR ($CDCl_3$): 1.34 (t, J=7.5 Hz, 3H), 2.39 (s, 3H), 2.50 (s, 3H), 4.31 (q, J=7.5 Hz, 2H), 4.40 (s, 2H), 7.15 (d, J=8.4 Hz, 1H), 7.66 (d, J=8,4 Hz, 1H). Mass spectrum: $(M+NH_4)^+$=271.

B. 2,6-Dimethyl-3-nitro-phenoxy Acetic Acid: To a solution of 200 mg (0.79 mmol) of ethyl 2,6-dimethyl-3-nitrophenoxyl acetate in 2 mL of methanol was added 600 μL of 3N sodium hydroxide. After the reaction mixture was stirred at room temperature for 10 min, it was acidified with 3N HCl. The reaction was allowed to stir for additional 1 h, and then partitioned between water and methylene chloride. The combined organic extracts were washed with brine and dried over anhydrous sodium sulfate, filtered and evaporated to dryness under reduced pressure. Trituration with hexanes to give 160 mg (90%) of 2,6-dimethyl-3-nitro-phenoxy acetic acid as a white solid. $^1$H NMR (CD$_3$OD): 2.39 (s, 3H), 2.45 (s, 3H), 4.48 (s, 2H), 7.24 (d, J=8.7 Hz, 1H), 7.63 (d, J=8.7 Hz, 1H). Mass spectrum: (M+NH$_4$)$^+$=243.

C. 5-(2,6-Dimethyl-3-nitro-phenoxyacetyl)amino-2-f(3R, 3aS,6aR)-bis-tetrahydrofuran-3-yl-oxycarbonyl)amino-1,6-diphenyl-3-hydroxyhexane: To a solution of 100 mg (0.23 mmol) of 2-((3R,3aS,6aR)-bis-tetrahydrofuran-3-yl-oxycarbonyl)amino-3-hydroxy-5-amino-1,6-diphenylhexane in 1 mL of THF and 1 mL of methylene chloride was subsequently added 51 mg (0.23 mmol) of 2,6-dimethyl-3-nitro-phenoxy acetic acid, 44 mg (0.23 mmol) of EDIC, 3.1 mg (0.023 mmol) of HOBT, and 63 μL (0.46 mmol) of triethyl amine. The resulting solution was allowed to stir at ambient temperature for 6 h, and concentrated in vacao. The residue was taken up in ethyl acetate, washed with one portion of 3N HCl, one portion of 10% aqueous NaHCO$_3$, and one portion of saturated brine, dried over MgSO$_4$, and concentrated in vacuo. The resulting product mixture was purified by silica gel chromatography using 70% ethyl acetate:hexanes as an eluent to provide 150 mg (100%) of the desired compound. $^1$H NMR (CDCl$_3$) δ 1.66 (m, 2H), 1.82 (m, 2H), 2.17 (s, 3H), 2.28 (s, 3H), 2.80–3.03 (m, 5H), 3.76 (dd, J=6.0, 9.0 Hz, 2H), 3.79 (m, 1H), 3.81 (m, 2H), 4.00 (m, 1H), 4.06 (d, J=15.0 Hz, 1H), 4.24 (d, J=15.0 Hz, 1H), 4.33 (m, 1H), 5.06 (m, 2H), 5.68 (d, J=5.4 Hz, 1H), 6.81 (d, J=7.5 Hz, 1H), 7.15–7.32 (m, 12H), 7.68 (d, J=7.5 Hz, 1H). Mass spectrum: (M+H)$^+$=648.

D. 5-(2,6-Dimethyl-3-amino-phenoxyacetyl)amino)=-2-((3R,3aS,6aR)-bis-tetrahydrofuran-3-yl-oxycarbonyl)amino-1,6-diphenyl-3-hydroxyhexane: To a solution of 155 mg (0.23 mmol) of 5-(2,6-dimethyl-3-nitro-phenoxyacetyl)amino)-2-((3S,3aR,6aS)-bis-tetrahydrofuran-3-yl-oxycarbonyl)amino-1,6-diphenyl-3-hydroxyhexane in 3 mL of methanol was added 15 mg of Pd/C(10%). The reaction mixture was stirred under 1 atomsphere of hydrogen for 2 h. The Pd/C was removed over a celite pad, and the solvent was evaporated to dryness under reduced pressure to give 120 mg of desired product as a white solid. The solid recrystalized in methylene chloride and ether gave 99 mg (70%) of pure compound. $^1$H NMR (CDCl$_3$) δ 1.65 (m, 2H), 1.81 (t, J=6.0 Hz, 2H), 1.93 (s, 3H), 2.01 (s, 3H), 2.80–3.03 (m, 2H), 3.79 (m, 1H), 3.88 (m, 2H), 4.01 (dd, J=9.6, 6.0 Hz, 1H), 4.04 (d, J=15.0 Hz, 1H), 4.19 (d, J=15.0 Hz, 1H), 4.31 (m, 1H), 5.08 (m, 1H), 5.13 (d, J=9.3 Hz, 1H), 5.69 (d, J=5.7 Hz, 1H), 6.48 (d, J=7.5 Hz, 1H), 6.82 (d, J=7.5 Hz, 1H), 6.98 (d, J=8.7 Hz, 1H), 7.15–7.32 (m, 12H). Mass spectrum: (M+H)$^+$=618.

EXAMPLE 17

(2S,3S,5S)-5-(2,6-Dimethyl-4-aminoacetyl)amino-2-((3R,3aS,6aR)-bis-tetrahydrofuran-3-yl-oxycarbonyl)amino-1,6-diphenyl-3-hydroxyhexane A. Ethyl 2,6-Dimethyl-4-nitro-phenylthioacetate: To a solution of 3 g (18.0 mmol) of 2,6-dimethyl-4-nitro phenol in 18 mL of methylene chloride cooled at −15° C. was added 7.5 mL (54.0 mmol) of triethyl amine and 4.5 mL (27.0 mmol) of trifluoromethanesulfonic anhydride. After the reaction mixture was stirred at −15° C. for 10 min, it was partitioned between 3N HCl and methylene chloride. The combined organic extracts were washed with saturated sodium bicarbonate, brine, dried over anhydrous sodium sulfate, filtered and evaporated to dryness under reduced pressure to give 4.8 g (100%) of 2,6-dimethyl-4-nitro-phenyltrifluoromethanesulfonate as a light yellow solid.

To a stirred suspension of 570 mg (60% in oil) (14.2 mmol) of sodium hydride in 9 mL of DMF under atmospheric nitrogen at 0° C. was added dropwise 1.64 mL of ethyl thioacetate. After stirring at room temperature for 1 h, it was cooled to 0° C. A solution of 2 g (7.5 mmol) of 2,6-dimethyl-3-nitro-phenyl trifluoromethanesulfonate in 6 mL of DMF was introduced. After stirring at-0° C. for 20 min. it was partitioned between ethyl ether and 3N HCl. The combined organic extracts were washed with brine, dried over MgSO$_4$, filtered and evaporated under reduced pressure. The resulting residue was purified by chromatography using 5% ethyl acetate: hexanes to provide 1.2 g (60%) of 2,6-dimethyl-4-nitro-thiophenol. $^1$H NMR (CDCl$_3$): 2.43 (s, 3H), 3.67 (s, 1H), 7.93 (s, 2H).

A solution of 155 mg (1.48 mmol) of 2,6-dimethyl-4-nitro-thiophenol in 1.6 mL of dimethylformamide was treated with 407 mg (2.95 mmol) of potassium carbonate and 200 μL (1.77 mmol) of ethyl bromoacetate. The resulting solution was stirred at room temperature for 0.5 h. The reaction mixture was partitioned between ethyl acetate and 3N hydrogen chloride. The combined organic layer was washed with diluted brine, dried over magnesium sulfate, filtered, and evaporated in vacuo. Silica gel chromatography using 5% ethyl acetate:hexanes gave 280 mg (70%) of ethyl 2,6-dimethyl-3-nitrophenylthio acetate as a light yellow oil. $^1$H NMR (CDCl$_3$): 1.16 (t, J=7.5 Hz, 3H), 2.64 (s, 6H), 3.43 (s, 2H), 4.06 (q, J=7.5 Hz, 2H), 7.94 (s, 2H). Mass spectrum: (M+NH$_4$)$^+$=287.

B. 2,6-Dimethyl-4-nitro-phenylthio Acetic Acid: To a solution of 280 mg (1.04 mmol) of ethyl 2,6-dimethyl-4-nitrophenylthio acetate in 2 mL of methanol was added 600 μL of 3N sodium hydroxide. After the reaction mixture was stirred at room temperature for 10 min, it was acidified with 3N HCl. The reaction was allowed to stir for additional 1 h, and then partitioned between water and methylene chloride. The combined organic extracts were washed with brine and dried over anhydrous sodium sulfate, filtered and evaporated to dryness under reduced pressure. Trituration with hexanes gave 227 mg (91%) of 2,6-dimethyl-4-nitro-phenylthio acetic acid as a white solid. $^1$H NMR (d$_6$-DMSO): 2.55 (s, 6H), 3.48 (s, 2H), 7.98 (s, 2H), 12.64 (bs, 1H). Mass spectrum: (M+NH$_4$)$^+$=259.

C. 5-(2,6-Dimethyl-4-nitro-phenylthioacetyl)amino-2-((3R,3aS,6aR)-bis-tetrahydrofuran-3-yl-oxycarbonyl)amino-1,6-diphenyl-3-hydroxyhexane: To a solution of 385 mg (0.88 mmol) of 2-((3R,3aS,6aR)-bis-tetrahydrofuran-3-yl-oxycarbonyl)anino-3-hydroxy-5-amino-1,6-diphenylhexane in 3.5 mL of THF and 3.5 mL of methylene chloride was subsequently added 210 mg (0.88 mmol) of 2,6-dimethyl-4-nitro-phenylthio acetic acid, 166 mg (0.88 mmol) of EDIC, 12 mg (0.09 mmol) of HOBT, and 255 μL (1.83 mmol) of triethyl amine. The resulting solution was allowed to stir at ambient temperature for 6 h, and concentrated in vacuo. The residue was taken up in ethyl acetate, washed with one portion of 3N HCl, one portion of 10% aqueous NaHCO$_3$, and one portion of saturated brine, dried over MgSO$_4$, and concentrated in vacuo. The resulting product mixture was triturated with mixture of ethyl acetate and methylene chloride to provide 585 mg (100%) of the desired compound.

D. 5-(2,6-Dimethyl-4-amino-phenylthioacetyl)amino-2-((3R,3aS,6aR)-bis-tetrahydrofuran-3-yl-oxycarbonyl) amino-1,6-diphenyl-3-hydroxybexane: To a solution of 585 mg (0.88 mmol) of 5-(2,6-dimethyl-4-nitro-phenylthio acetyl)amino)-2-((3S,3aR,6aS)-bis-tetrahydrofuran-3-yl-oxycarbonyl)amino-1,6-diphenyl-3-hydroxyhexane in 5 mL of methanol was added 60 mg of Pd/C(10%). The reaction mixture was stirred under one atmosphere of hydrogen for 2 h. The catalyst was removed over a celite pad, and the solvent was evaporated to dryness under reduced pressure to give 550 mg (99%) of desired product as a white solid. $^1$H NMR (CDCl$_3$) δ 1.57 (m, 2H), 1.65 (m, 2H), 2.38 (s, 6H), 2.72–2.82 (m, 4H), 2.94 (m, 1H), 3.18 (s, 2H), 3.23 (m, 1 H), 3.32 (m, 1H), 3.49 (m, 1H), 3.74 (dd, J=9.0, 6.0 Hz, 2H), 3.78 (m, 1H), 3.88 (dt, J=8.4, 2.0 Hz, 1H), 4.02 (m, 3H), 5.08 (m, 2H), 5.68 (d, J=5.4 Hz, 1H), 6.27 (d, J=7.5 Hz, 2H), 6.41 (s, 2H), 7.07 (d, J=8.1 Hz, 2H), 7.18 (d, J=8.1 Hz, 2H), 7.21–7.32 (m, 6H). Mass spectrum: (M+H)$^+$=634.

EXAMPLE 18

(2S,3S,5S)-5-(2,6-Dimethyl-4-amino-phensulfonylacetyl)amino-2-((3R,3aS,6aR)-bis-tetrahydrofuran-3-yl-oxycarbonyl)amino-1,6-diphenyl-3-hydroxyhexane See Example 19 below.

EXAMPLE 19

(2S,3S,5S)-5-(2,6-Dimethyl-4-amino-phenylsulfinylacetyl)amino-2-((3R,3aS,6aR)-bis-tetrahydrofuran-3-yl-oxycarbonyl)amino-1,6-diphenyl-3-hydroxyhexane To a 0° C. solution of 462 mg (0.73 mmol) of 5-(2,6-dimethyl-4-amino-phenylthioacetyl)amino-2-((3R,3aS, 6aR)-bis-tetrahydrofuran-3-yl-oxycarbonyl)-amino-1,6-diphenyl-3-hydroxyhexane in 5 mL of methylene chloride was added dropwise a solution of mCPBA in methylene chloride. The reaction was carefully monitored by TLC. The reaction was stopped when an equal amount of desired compounds was formed. The residue was taken up in methylene chloride, washed with one portion of NaHSO$_3$, one portion of 10% aqueous NaHCO$_3$, and one portion of saturated brine, dried over MgSO$_4$, and concentrated in vacuo. The resulting product mixture was purified on a preparative silica gel TLC developed with 8% methanol:methylene chloride to provide 60 mg of (2S,3S,5S)-5-(2,6-dimethyl-4-amino-phenylsulfoxyacetyl)amino-2-((3R,3aS, 6aR)-bis-tetrahydrofuran-3-yl-oxycarbonyl)amino-1,6-diphenyl-3-hydroxyhexane, and 42 mg of (2S,3S,5S)-5-(2, 6-dimethyl-3-amino-phensulfylacetyl)amino-2-((3R,3aS, 6aR)-bis-tetrahydrofuran-3-yl-oxycarbonyl)amino -1,6-diphenyl-3-hydroxyhexane both as white solids. For Example 18: $^1$H NMR (CDCl$_3$) δ 1.62–1.77 (m, 6H), 2.49 (s, 6H), 2.76–2.87 (m, 4H), 2.94 (m, 1H), 3.25 (d, J=1.20 Hz, 1H), 3.73 (m, 3H), 3.78 (m, 1H), 3.89 (dt, J=7.5, 2.1 Hz, 1H), 4.01 (m, 2H), 4.32 (m, 1H), 5.08 (q, J=6.3 Hz, 1H), 5.10 (t, J=7.5 Hz, 1H), 5.68 (d, J=5.4 Hz, 1H), 6.34 (s, 2H), 6.64 (d, J=7.8 Hz, 1H), 7.12–7.31 (m, 12H). Mass spectrum: (M+H)$^+$=650. For Example 19: $^1$H NMR (CDCl$_3$) δ 1.64 (m, 2H), 1.70 (m, 6H), 2.54 (s, 6H), 2.57 (m, 2H), 2.76–2.86 (m, 3H), 2.95 (m, 1H), 3.67 (m, 1H), 3.77 (dd, J=9.0, 6.0 Hz, 2H), 3.86 (m, 2H), 3.89 (s, 2H), 3.93 (m, 1H), 4.00 (dd, J=9.6, 6.3 Hz, 1H), 4.22 (m, 1H), 5.08 (dd, J=15.0, 6.3 Hz, 2H), 5.16 (t, J=9.3 Hz, 1H), 5.49 (d, J=5.4 Hz, 1H), 6.39 (s, 2H), 6.80 (d, J=7.8 Hz, 1H), 7.12–7.31 (m, 12H). Mass spectrum: (M+H)$^+$=666.

EXAMPLE 20

(2S,3S,5S)-2,5-Di-((3R,3aS,6aR)-bis-Tetrahydrofuran-3-yl-oxycarbonyl)amino-1,6-diphenyl-3-hydroxyhexane A. (2S,3S,5S)-2-amino-3-hydroxy-5-(t-butyloxycarbonylamino)-1,6-diphenylhexane: To a solution of 854 mg (2.22 mmol) of (2S,3S,5S)-2-amino-3-hydroxy-5-(t-butyloxycarbonylamino)-1,6-diphenylhexane in 10 mL of THF was added 1 mL of 6N HCl. The resulting solution was heated at 50° C. for 2 h. After washing with one portion of 3N of aqueous NaOH and one portion of saturated brine, the methylene chloride solution was dried over Na$_2$SO$_4$ and concentrated in vacuo to give 630 mg (100%) of desired compound. The residue was used in reaction (B) below without further purification.

B. (2S,3S,5S)-2, 5-Di-((3R,3aS,6aR)-bis-tetrahydrofuran-3-yl-oxycarbonyl)amino-1,6-diphenyl-3-hydroxyhexane: To a solution of 45 mg (0.16 mmol) of (2S,3S,5S)-2, 5-diamino-3-hydroxy-1,6-diphenylhexane in 2 mL of 1,2-dichloroethane was added 98 mg (0.32 mmol) of ((3R,3aS,6aR)-bis-tetrahydrofuran-3-yl-oxycarbonyl) oxy-4-nitro benzene. The resulting solution was refluxed for 12 h. After washing with three portions of 10% aqueous NaHCO$_3$ and one portion of saturated brine, the solution was dried over Na$_2$SO$_4$ and concentrated in vacuo. The residue was purified by silica gel chromatography by eluting with 60% of ethyl acetate:hexanes to provide 38 mg (40%) of the desired compound. $^1$H NMR (CDCl$_3$) δ 1.70 (m, 6H), 2.73 (m, 2H), 2.84 (M, 4H), 2.95 (m, 2H), 3.72 (m, 4H), 3.77 (m, 2H), 3.88 (m, 2H), 4.00 (m, 2H), 4.72 (d, J=9.3 Hz, 1H), 4.96 (d, J=9.3 Hz, 1H), 5.08 (q, J=8.1 Hz, 2H), 5.67 (d, J=5.4 Hz, 2H), 7.10–7.31 (m, 10H). Mass spectrum: (M+H)$^+$=597.

EXAMPLE 21

(2S,3S,5S)-2,5-Di-((3S,3aR,6aS)-bis-Tetrabydrofuran-3-yl-oxycarbonyl)amino-1,6-diphenyl-3-hydroxyhexane To a solution of 57 mg (0.20 mmol) of (2S,3S,5S)-2, 5-diamino-3-hydroxy-1,6-diphenylhexane in 2 mL of 1,2-dichloroethane was added 120 mg (0.40 mmol) of ((3S,3aR, 6aS)-bis-tetrahydrofuran-3-yl-oxycarbonyl)oxy-4-nitro benzene. The resulting solution was refluxed for 12 h. After washing with three portions of 10% aqueous NaHCO$_3$ and one portion of saturated brine, the solution was dried over Na$_2$SO$_4$ and concentrated in vacuo. The residue was purified by silica gel chromatography by eluting with 40–60% of ethyl acetate:hexanes to provide 52 mg (43%) of the desired compound. $^1$H NMR (CDCl$_3$) δ 1.67 (m, 2H), 1.82–2.00 (m, 4H), 2.70 (m, 2H), 2.83 (m, 2H), 3.03 (m, 2H), 3.65 (m, 2H), 3.82 (m, 4H), 3.99 (m, 4H), 4.00 (m, 2H), 4.79 (d, J=7.8 Hz, 1H), 5.00 (d, J=7.8 Hz, 1H), 5.07 (m, 2H), 5.71 (d, J=5.4 Hz, 2H), 7.10–7.31 (m, 10H). Mass spectrum: (M+H)$^+$=597.

EXAMPLE 22

(2S,3S,5S)-2-((3R,3aS,6aR)-bis-Tetrahydrofuran-3-yl-oxycarbonyl)amino-5-((3S,3aR,6aS)-bis-Tetrahydrofutran-3-yl-oxycarbonyl)amino-1,6-diphenyl-3-hydroxyhexane To a solution of 80 mg (0.18 mmol) of (2S,3S,5S)-2-((3R, 3aS,6aR)-bis-tetrahydrofuran-3-yl-oxycarbonyl)amino-3-hydroxy-5-amino-1,6-diphenylhexane in 2 mL of 1,2-dichloroethane was added 56 mg (0.19 mmol) of ((3S,3aR, 6aS)-bis-tetrahydrofuran-3-yl-oxycarbonyl)oxy-4-nitro benzene. The resulting solution was refluxed for 12 h. After washing with three portions of 10% aqueous NaHCO$_3$ and one portion of saturated brine, the solution was dried over Na$_2$SO$_4$ and concentrated in vacuo. The residue was purified by silica gel chromatography by eluting with 40–60% of ethyl acetate:hexanes to provide 40 mg (37%) of the desired compound. $^1$H NMR (CDCl$_3$) δ 1.67 (m, 2H), 1.78–2.00 (m, 4H), 2.79 (m, 2H), 2.85 (m, 2H), 3.00 (m, 2H), 3.67 (m, 2H), 3.73 (m, 2H), 3.85 (m, 2H), 3.88 (m, 2H), 3.97 (m, 4H), 4.78 (d, J=8.1 Hz, 1H), 4.97 (d, J=9.3 Hz, 1H), 5.08 (m, 2H), 5.68 (d, J=5.7 Hz, 1H), 5.70 (d, J=5.7 Hz, 1H), 7.10–7.31 (m, 10H). Mass spectrum: (M+H)$^+$=597.

EXAMPLE 23

(2S,3S,5S)-2-((3S,3aR,6aS)-bis-tetrahydrofuran-3-yl-oxycarbonyl)amino-5-((3R,3aS,6aR)-bis-tetrahydrofuran-3-yl-oxycarbonyl)amino-1,6-diphenyl-3-hydroxyhexane To a solution of 51 mg (0.12 mmol) of (2S,3S,5S)-2-((3S,3aR,6aS)-bis-tetrahydrofuran-3-yl-oxycarbonyl)amino-3-hydroxy-5-amino-1,6-diphenylhexane in 2 mL of 1,2-dichloroethane was added 35 mg (0.12 mmol) of ((3R,3aS,6aR)-bis-tetrahydrofuran-3-yl-oxycarbonyl)oxy-4-nitro benzene. The resulting solution was refluxed for 12 h. After washing with three portions of 10% aqueous NaHCO$_3$ and one portion of saturated brine, the solution was dried over Na$_2$SO$_4$ and concentrated in vacuo. The residue was purified by silica gel chromatography by eluting with 40–60% of ethyl acetate:hexanes to provide 42 mg (61 %) of the desired compound. $^1$H NMR (CDCl$_3$) δ 1.69 (m, 2H), 1.89 (m,1H), 2.00 (m, 1H), 2.71 (m, 2H), 2.83 (m, 2H), 2.88 (m, 2H), 2.93–3.07 (m, 2H), 3.65 (m, 2H), 3.72 (m, 2H), 3.86 (m, 2H), 3.99 (m, 4H), 4.76 (d, J=9.0 Hz, 1H), 5.03 (d, J=9.0 Hz, 1H), 5.08 (m, 2H), 5.68 (d, J=5.4 Hz, 1H), 5.71 (d, J=5.4 Hz, 1H), 7.10–7.31 (m, 10H). Mass spectrum: (M+H)$^+$=597.

EXAMPLE 24

(2S,3S,5S)-5-(4,6-Dimethyl-benzimidazol-5-yloxy-acetyl)amino-2-((3R,3aS,6aR)-bis-tetrahydrofuran-3-yl-oxycarbonyl)amino-1,6-diphenyl-3-hydroxyhexane A. Ethyl 4-(Allyloxycarbonyl)amino-2,6-Dimethyl-phenoxyacetate: To a solution of 3 g (13.5 mmol) of ethyl 2,6-dimethyltamino phenoxyacetate in 25 mL of ethanol cooled at room temperature was added 2.72 mL (33.6 mmol) of pyridine and 1.7 mL (16.1 mmol) of allyl chloroformate. After the reaction mixture was stirred for 2 h, it was partitioned between 3N HCl and ethyl acetate. The combined organic extracts were washed with saturated sodium bicarbonate, brine, dried over anhydrous sodium sulfate, filtered and evaporated to dryness under reduced pressure to give 4.09 g (99%) of ethyl 4-(allyloxycarbonyl)amino-2,6-dimethyl-phenoxyacetate as a light pink solid. $^1$H NMR (CDCl$_3$) δ 1.33 (t, J=7.2 Hz, 3H), 2.27 (s, 6H), 4.30 (q, J=7.2 Hz, 2H), 4.36 (s, 2H), 4.65 (dt, J=0.9, 7.2 Hz, 2H), 5.26 (dq, J=0.9, 10.5 Hz, 1H), 5.36 (dq, J=0.9, 17.1 Hz, 1H), 5.96 (m, 1H), 6.49 (bs, 1H), 7.04 (s, 2H). Mass spectrum: (M+H)$^+$=325.

B. Ethyl 4-(Allyloxycarbonyl)amino-2,6-dimethyl-3-nitro-phenoxyacetate: To a solution of 3.63 g (11.8 mmol) of ethyl 4-(allyloxycarbonyl)amino-2,6-dimethyl-phenoxyacetate and 1.63 g (23.6 mmol) of sodium nitrite in 20 mL of methylene chloride was added 8 mL of trifluoroacetic acid slowly. After the reaction mixture was stirred at room temperature for 1 h, it was carefully partitioned between saturated sodium bicarbonate solution and methylene chloride. The combined organic extracts were washed with brine and dried over anhydrous sodium sulfate, filtered and evaporated to dryness under reduced pressure. The residues was purified by silica gel chromatography by eluting with 10% of ethyl acetate:hexanes to provide 2.9 g (70%) of the desired compound as a light pink solid. $^1$H NMR (CDCl$_3$) δ 1.34 (t, J=6.9 Hz, 3H), 2.34 (s, 3H), 2.37 (s, 3H), 4.32 (q, J=6.9 Hz, 2H), 4.38 (s, 2H), 4.66 (dt, J=1.5, 6.0 Hz, 2H), 5.26 (dq, J=1.5, 10.5 Hz, 1H), 5.37 (dq, J=1.5, 16.5 Hz, 1H), 5.96 (m, 1H), 7.77 (s, 1H), 7.82 (s, 1H). Mass spectrum: (M+H)$^+$=370.

C. Ethyl 4Amino-2,6-dimethyl-3-nitro-phenoxyacetate: A solution of 180 mg (0.51 mmol) of ethyl 4-(allyloxycarbonyl)amino-2,6-dimethyl-3-nitro-phenoxyacetate in 2 mL of dicloromethane was treated with 54 mg (0.05 mmol) of tetrakis(triphenylphosphine) palladium(0) and 27 mg (0.1 mmol) of triphenyl phosphine. The resulting solution was stirred at room temperature under argon and 128 μL (1.5 mmol) of pyrolidine was added. After stirring at room temperature for 10 min, the reaction mixture was evaporated under reduced pressure. Silica gel chromatography using 50% ethyl acetate:hexanes gave 135 mg (99%) of ethyl 4-amino-2,6-dimethyl-3-nitro-phenoxyacetate. $^1$H NMR (CDCl$_3$) δ 1.34 (t, J=6.6 Hz, 3H), 2.27 (s, 3H), 2.40 (s, 3H), 4.30 (q, J=6.6 Hz, 2H), 4.32 (s, 2H), 4.95 (bs, 2H), 6.48 (s, 1H). Mass spectrum: (M+NH$_4$)$^+$=286.

D. Ethyl 3, 4-Diamino-2,6-dimethyl-phenoxyacetate: To a solution of 135 mg (0.5 mmol) of ethyl 4amino-2,6dimethyl-3-nitro-phenoxyacetate in 2 mL of methanol was added 15 mg of Pd/C(10%). The reaction mixture was stirred under one atmosphere of hydrogen overnight. The Pd/C was removed over a celite pad, and the solvent was evaporated to dryness under reduced pressure to give 115 mg (97%) of desired product as a brown solid. $^1$H NMR (CDCl$_3$) δ 1.33 (t, J=6.9 Hz, 3H), 2.15 (s, 3H), 2.17 (s, 3H), 3.33 (bs, 4H), 4.30 (q, J=6.9 Hz, 2H), 4.32 (s, 2H), 6.53 (s, 1H). Mass spectrum: (M+NH$_4$)$^+$=256.

E. 4,6-Dimethyl-benzimidazolyl-5-oxy-acetic Acid: A solution of 100 mg (0.42 mmol) of ethyl 3, 4-diamino-2,6-dimethyl-phenoxyacetate in 2 mL of formic acid (98% wt.) was refluxed for 48 h. The formic acid was evaporated to dryness under reduced pressure to give 80 mg (86%) of 4,6-dimethyl-5-oxy-benzimidazolyl acetic acid as a dark brown solid. $^1$H NMR (DMSO-d6): d 2.32 (s, 3H), 2.43 (s, 3H), 4.36 (s, 2H), 7.00 (s, 1H), 8.07 (s, 1H). Mass spectrum: (M+NH$_4$)$^+$=221.

F. (2S,3S,5S)-5-(4,6-Dimethyl-benzimidazolyl-5-oxy-acetyl)amino-2-((3R,3aS,6aR)-bis-tetrahydrofuran-3-yl-oxycarbonyl)amino-1,6-diphenyl-3-hydroxyhexane: To a solution of 100 mg (0.23 mmol) of (2S,3S,5S)-2-((3R,3aS,6aR)-bis-tetrahydrofuran-3-yl-oxycarbonyl)amino-3-hydroxy-5-amino-1,6-diphenylhexane in 1 mL of THF and 1 mL of methylene chloride was subsequently added 50 mg (0.23 mmol) of 4,6-dimethyl-5-oxy-benzimidazolyl acetic acid, 44 mg (0.23 mmol) of EDIC, 3 mg (0.023 mmol) of HOBT, and 63 μL (0.46 mmol) of triethyl amine. The resulting solution was allowed to stir at ambient temperature for 8 h, and concentrated in vacuo. The resulting product mixture was purified by silica gel chromatography using 5% methanol:chloroforrn to give 114 mg (78%) of desired compound. $^1$H NMR (CDCl$_3$) δ 1.27 (m, 1H), 1.68–1.86 (m, 6H), 2.24 (s, 3H), 2.37 (s, 3H), 2.96 (m, 6H), 3.80 (m, SH), 3.98 (dd, J=6.0, 9.3 Hz, 1H), 4.23 (s, 2H), 4.35 (m, 1H), 5.11 (m, 2H), 5.72 (d, J=5.4 Hz, 1H), 7.04–7.33 (m, 10H), 8.00 (s, 1H). Mass spectrum: (M+H)$^+$=643.

EXAMPLE 25

(2S,3S,5S)-5-(4,6-Dimethyl-benzimidazolinon-5-yloxy-acetyl)amino-2-((3R,3aS,6aR)-bis-tetrahydrofuran-3-yl-oxycarbonyl)amino-1,6-diphenyl-3-hydroxyhexane A. Ethyl 4-(Ethoxycarbonyl)amino-2,6-Dimethyl-phenoxyacetate: To a solution of 2.64 g (11.8 mmol) of 2,6-dimethyl-4-amino phenylacetate in 25 mL of ethanol cooled at room temperature was added 2.40 mL (29.6 mmol) of pyridine and 1.36 mL (14.2 mmol) of ethyl chloroformate. After the reaction mixture was stirred 2 h, it was partitioned between 3N HCl and ethyl acetate. The combined organic extracts were washed with saturated sodium bicarbonate, brine, dried over anhydrous sodium sulfate, filtered and evaporated to dryness under reduced pressure to give 3.4 g (98%) of ethyl 4-(ethyloxycarbonyl)amino-2,6-dimethyl-phenoxyacetate as a brown oil. $^1$H NMR (CDCl$_3$) δ 1.30 (t, J=6.3 Hz, 3H), 1.33 (t, J=6.3 Hz, 3H), 2.28 (s, 6H), 4.20 (q, J=6.3 Hz, 2H), 4.30 (q, J=6.3 Hz, 2H), 4.36 (s, 2H), 6.42 (s, 1H), 7.02 (s, 2H). Mass spectrum: (M+NH$_4$)$^+$=313.

B. Ethyl 4-(Ethoxycarbonyl)amino-2,6-Dimethyl-3-nitro-phenoxyacetate: To a solution of 3.40 g (11.5 mmol) of ethyl 4-(ethoxycarbonyl)amino-2,6-dimethyl-phenoxyacetate in 2.4 mL of water was added 3.8 mL of ice and 1.4 mL of acetic anhydride followed by 1.2 mL concentrated nitric acid slowly. After the reaction mixture was stirred at 60° C. for 10 min, it was carefully partitioned between water and methylene chloride. The organic extracts were washed with saturated sodium bicarbonate solution, brine and dried over anhydrous sodium sulfate, filtered and evaporated to dryness under reduced pressure. The residues was purified by silica gel chromatography by eluting with 20% of ethyl acetate-:hexanes to provide 3.02 g (77%) of the desired compound as light yellow solid. $^1$H NMR (CDCl$_3$) δ 1.32 (t, J=6.0 Hz, 3H), 1.34 (t, J=6.0 Hz, 3H), 2.35 (s, 3H), 2.37 (s, 3H), 4.21 (q, J=6.0 Hz, 2H), 4.31 (q, J=6.0 Hz, 2H), 4.37 (s, 2H), 7.70 (s, 1H), 7.82 (s, 1H). Mass spectrum: (M+NH$_4$)$^+$=358.

C. Ethyl 3-Amino-4-(Ethoxycarbonvy)amino-2,6-Dimethyl-phenoxyacetate: To a solution of 2.36 g (6.94 mmol) of ethyl 4-(ethyloxycarbonyl)amino-2,6-dimethyl-3-nitro-phenoxyacetate in 15 mL of tetrahydrofuran was added 120 mg of Pd/C(10%). The reaction mixture was stirred under one atmosphere of hydrogen overnight. The Pd/C was removed over a celite pad, and the solvent was evaporated to dryness under reduced pressure to give 2.15 g (100%) of desired product as a yellow solid. $^1$H NMR (CDCl$_3$) δ 1.31 (t, J=7.5 Hz, 3H), 1.34 (t, J=7.5 Hz, 3H), 2.15 (s, 3H), 2.20 (s, 3H), 4.21 (q, J=7.5 Hz, 2H), 4.30 (q, J=7.5 Hz, 2H), 4.34 (s, 2H), 6.18 (bs, 1H), 6.95 (s, 1H). Mass spectrum: (M+NH$_4$)$^+$=328.

D. 4,6-Dimethyl-benzimidazolinone-5-oxy-acetic Acid: To a 7.5 mL of sodium ethoxide (1.2M) in ethanol solution was added 100 mg (0.32 mmol) of ethyl 3-amino-4-(ethyloxycarbonyl)amino-2,6-dimethyl-phenoxyacetate. After the reaction mixture was refluxed for 3 h, it was carefully evaporated to dryness. The residue was acidified with 3N HCl, and the resulting yellow solid was filtered, washed with small amount of water and ether. The solid was dried over vacumn to yield 50 mg (66%) of the desired compound as yellow solid. $^1$H NMR (CDCl$_3$) δ 2.17 (s, 3H), 2.19 (s, 3H), 4.28 (s, 2H), 6.55 (s, 1H), 10.38 (s, 1H), 10.56 (s, 1H), 12.83 (s, 1H). Mass spectrum: (M+NH$_4$)$^+$=254.

E. (2S,3S,5S)-5-(4,6-Dimethyl-2-benzimidazolinone-acetv)amino-2-((3R,3aS,6aR)-bis-tetrahydrofuran-3-yl-oxycarbonyl)amino-1,6-diphenyl-3-hydroxyhexane: To a solution of 83 mg (0.18 mmol) of (2S,3S,5S)-2-((3R,3aS,6aR)-bis-tetrahydrofuran-3-yl-oxycarbonyl)amino-3-hydroxy-5-amino-1,6-diphenylhexane in 1 mL of THF and 2 mL of DMF was subsequently added 44 mg (0.18 mmol) of 4,6-Dimethyl-benzimidazolinone-5-oxy-acetic Acid, 36 mg (0.18 mmol) of EDIC, 3 mg (0.02 mmol) of HOBT, and 53 μL (0.38 mmol) of triethyl amine. The resulting solution was allowed to stir at ambient temperature for 8 h, and concentrated in vacuo. The resulting product mixture was purified by thin layer silica gel chromatography using 8% methanol:chloroform to give 95 mg (80%) of desired compound. $^1$H NMR (CDCl$_3$) δ 1.48 (m, 1H), 1.54–1.74 (m, 3H), 2.13 (s, 3H), 2.15 (s, 3H), 2.78 (m, 2H), 2.83 (m, 2H), 2.88 (m, 2H), 2.97 (s, 1H), 3.69 (m, 2H), 3.77 (m, 1H), 3.92 (dd, J=6.0, 9.3 Hz, 2H), 4.03 (AB, J=15 Hz, 2H), 4.09 (m, 1H), 4.53 (m, 1H), 5.58 (d, J=6.0 Hz, 1H), 6.67 (s, 1H), 7.12–7.25 (m, 10H), 7.95 (s, 1H). Mass spectrum: (M+H)$^+$=659.

EXAMPLE 26

(2S,3S,5S)-5-(4,6-Dimethyl-benzoxazol-5-yloxy-acetyl)amino-2-((3R,3aS,6aR)-bis-tetrahydrofuran-3-yl-oxycarbonyl)amino-1,6-diphenyl-3-hydroxyhexane A. Ethyl 4-Anino-2,6-Dimethyl-3-Hydroxyl-phenoxyacetate: To a solution of 900 mg (4.0 mmol) of ethyl 2,6-dimethyl-3-hydroxyl-phenoxyacetate in 40 mL of acetonitrile at room temperature was added 4 mL (4.0 mmol) of N-methyl-2-O-nitropyridinium nitrite in acetonitrile. The reaction mixture was stirred for 10 min, then partitioned between water and methylene chloride. The combined organic extracts were washed with saturated sodium bicarbonate, brine, dried over anhydrous sodium sulfate, filtered and evaporated to dryness under reduced pressure to give 650 mg (60%) of ethyl 2,6-dimethyl-3-hydroxyl-4-nitro-phenoxyacetate as a yellow powder.

To a solution of 250 mg (0.93 mmol) of ethyl 2,6-dimethyl-3-hydroxyl-4-nitro-phenoxyacetate in 3 mL of tetrahydrofuran was added 10 mg of Pd/C(10%). The reaction mixture was stirred under one atmosphere of hydrogen overnight. The Pd/C was removed over a celite pad, and the solvent was evaporated to dryness under reduced pressure to give 220 mg (99%) of desired product as a light brown solid. $^1$H NMR (CDCl$_3$) δ 1.33 (t, J=7.5 Hz, 3H), 2.18 (s, 3H), 2.20 (s, 3H), 3.30 (bs, 2H), 4.30 (q, J=7.5 Hz, 2H), 4.32 (s, 2H), 4.88 (s, 1H), 6.49 (s, 1H). Mass spectrum: (M+NH$_4$)$^+$=257.

B. 4,6-Dimethyl-benzoxazolyl-5-oxy-acetic Acid: A solution of 150 mg (0.63 mmol) of ethyl 4-amino-2,6-dimethyl-3-hydroxyl-phenoxyacetate in 2 mL of formic acid (98% wt.) was refluxed overnight. The formic acid was evaporated to dryness under reduced pressure. The residue was directly sublimated to give 75 mg (54%) of 4,6-dimethyl-5-oxy-benzoxazolyl acetic acid as a dark brown solid. $^1$H NMR (DMSO-d$_6$): d 2.34 (s, 3H), 2.42 (s, 3H), 4.45 (s, 2H), 7.46 (s, 1H), 8.64 (s, 1H), 12.95 (bs, 1H). Mass spectrum: (M+NH$_4$)$^+$=239.

C. (2S,3S,5S)-5-(4,6-Dimethyl-benzoxazolyl-5-oxy-acetyl)amino-2-((3R,3aS,6aR)-bis-tetrahydrofuran-3-yl-oxycarbonyl)amino-1,6-diphenyl-3-hydroxyhexane: To a solution of 100 mg (0.23 mmol) of (2S,3S,5S)-2-((3R,3aS,6aR)-bis-tetrahydrofuran-3-yl-oxycarbonyl)amino-3-hydroxy-5-amino-1,6-diphenylhexane in 1 mL of THF and 1 mL of methylene chloride was subsequently added 50 mg (0.23 mmol) of 4,6-dimethyl-benzoxazolyl-5-oxy-acetic Acid, 44 mg (0.23 mmol) of EDIC, 3 mg (0.02 mmol) of HOBT, and 63 μL (0.38 mmol) of triethyl amine. The resulting solution was allowed to stir at ambient temperature for 8 h, and concentrated in vacuo. The resulting product mixture was purified by thin layer silica gel chromatography using 5% methanol:chloroform to give 120 mg (81%) of desired compound.

$^1$H NMR (CDCl$_3$) δ 1.26 (m, 1H), 1.67 (m, 2H), 1.83 (m, 2H), 2.20 (s, 3H), 2.27 (s, 3H), 2.94 (m, 2H), 3.64 (d, J=3.9 Hz, 1H), 3.76 (dd, J=9.3, 6.0 Hz, 2H), 3.80 (t, J=6.6 Hz, 1H), 3.90 (td, J=3.0, 7.5 Hz, 2H), 4.12 (d, J=15.0 Hz, 1H), 4.29 (d, J=15.0 Hz, 1H), 4.33 (m, 1H), 5.08 (dd, J=3.9, 6.0 Hz, 1H), 5.10 (t, J=6.0 Hz, 1H), 5.69 (d, J=6.0 Hz), 1H), 6.95 (d, J=7.5 Hz, 1H), 7.16–7.33 (m, 10H), 7.40 (s, 1H), 8.05 (s, 1H). Mass spectrum: (M+H)$^+$=661.

EXAMPLE 27

(2S,3S,5S)-2-(2,6-Dimethylphenoxyacetyl)amino-5-(3(R,S)-2(R,S)-isopropyl-tetrahydrothienyloxycarbonyl)amino-1,6-diphenyl-3-hydroxyhexane A. (2S,3 S,5S)-2-(t-butyloxycarbonylamino)-5-(3(R,S)-2(R,S)-isopropyl-tetrahydrothienyloxycarbonyl)amino-1,6-diphenyl-3-hydroxyhexane: 3(R,S)-(2(R,S)-Isopropyl) tetrahydrothienyl pyridyl carbonate was prepared according to the procedure reported in US94/01370, published to Merck and incorporated herein by reference. To a solution of 500 mg (1.87 mmol) of carbonate in 5 mL of methylene chloride was added 791 mg (2.06 mmol) of (2S,3S,5S)-2-amino-3-hydroxy-5-(t-butyloxycarbonylamino)-1,6-diphenylhexane. The resulting solution was stirred for 12 h. After washing with 10% aqueous citric acid, sodium bicarbonate and one portion of saturated brine, the solution was dried over Na$_2$SO$_4$ and concentrated in vacuo. The residue was purified by silica gel chromatography to provide 781 mg (73%) of the desired compound.

B. (2S,3S,5S)-2-(2,6-Dimethylphenoxyacetyl)amino-5-(3(R,S)-2(R,S)-isopropyl-tetrahydrothienyloxycarbonyl) amino-1,6-diphenyl-3-hydroxyhexane: The Boc protecting group of the compound from Example 27A was removed using trifuoroacetic acid in methylene chloride and the resulting (2S,3S,5S)-2-amino-5-(3(R,S)-2(R,S)-isopropyl-tetrahydrothienyloxycarbonyl)amino-1,6-diphenyl-3-hydroxyhexane was coupled with 2,6-dimethylphenoxy acetic acid using standard coupling procedures yield desired compound.

EXAMPLE 28

(2S,3S,5S)-2-(2,6-Dimethylphenoxyacetyl)amino-5-(1,1-dioxo-3(R,S)-2(R,S)-isopropyl-tetrahydrothienyloxycarbonyl)amino-1,6-diphenyl-3-hydroxyhexane A. (2S,3S,5S)-2-(t-butyloxycarbonylamino)-5-(1,1-dioxo-3(R,S)-2(R,S)-isopropyl-tetrahydrothienyloxycarbonyl)amino-1,6-diphenyl-3-hydroxyhexane: To a solution of 523 mg (0.91 mmol) of compound from Example 27A in 5 mL of acetone and 0.5 mL of water was added 839 mg (1.37 mmol) of Oxone™ and 152 mg (1.82 mmol) of sodium bicarbonate. The resulting solution was stirred for 2 h. After partition between ethyl acetate and aqueous sodium bisulfite, the organic layer was washed with sodium bicarbonate and one portion of saturated brine. The solution was dried over Na$_2$SO$_4$ and concentrated in vacua. The residue was purified by silica gel chromatography eluted with 2% of methanol and chloroform to provide 422 mg of the desired compound.

B. (2S,3S,5S)-2-(2,6-Dimethyllphenoxyacetyl)amino-5-(1,1-dioxo-3(R,S)-2(R,S)-isopropyl-tetrahydrothienyloxycarbonyl)amino-1,6-diphenyl-3-hydroxyhexane. The Boc protecting group of the compound from Example 28A was removed using trifuoroacetic acid in methylene chloride and the resulting (2S,3S,5S)-2-amino-5-(1,1-dioxo-3(R,S)-2(R,S)-isopropyl-tetrahydrothienyloxycarbonyl)amino-1,6-diphenyl-3-hydroxyhexane was coupled with 2,6-dimethylphenoxy acetic acid using standard coupling procedures to give the desired compound.

EXAMPLE 29

(2S,3S,5S)-2-(2,6-Dimethylphenoxyacetyl)amino-5-(1,1-dioxo-3(R,S)-tetrahydrothiopyranyloxycarbonyl)amino-1,6-diphenyl-3-hydroxyhexane A. (2S,3S,5S)-2-(t-butyloxycarbonylamino)-5-(3(R,S)-tetrahydrothiopyranyloxycarbonyl)amino-1,6-diphenyl-3-hydroxyhexane. A solution of tetrahydrothiopyran-3-ol in methylene chloride was added Hünig's base and di-(2-pyridyl)carbonate. After the reaction was stirred at ambient temperature for 18 h, the reaction was diluted with chloroform, sequentially washed with 10% citric acid, sodium bicarbonate, brine, and dried over sodium sulfate. The product was isolated as a white solid which was purified by flash chromatography. Using the procedure of Example 27A, the above carbonate was reacted with (2S,3S,5S)-2-amino-3-hydroxy-5-(t-butyloxycarbonylamino)-1,6-diphenylhexane to give the desired compound.

B. (2S,3S,5S)-2-(t-butyloxycarbonylamino)-5-(1,1-dioxo-3(R,S)-tetrahydrothiopyranyloxycarbonyl)amino-1,6-diphenyl-3-hydroxyhexane. Oxidation of the above coupling product with Oxone™ according to the procedure of Example 28A provided (2S,3S,5S)-2-(t-butyloxycarbonylamino)-5-(1,1-dioxo-3(R,S)-tetrahydrothiopyranyloxycarbonyl)amino-1,6-diphenyl-3-hydroxyhexane.

C. (2S,3S,5S)-2-(2,6-Dimethylphenoxyacetyl)amino-5-(1,1-dioxo-3(R,S)-tetrahydrothiopyranyloxycarbonyl) amino-1,6-diphenyl-3-hydroxyhexane The Boc protecting group of the compound from Example 29B was removed using trifuoroacetic acid in methylene chloride and the resulting (2S,3S,5S)-2-amino-5-(1,1-dioxo-3(R,S)-tetrahydrothiopyranyloxycarbonyl)amino-1,6-diphenyl-3-hydroxyhexane with 2,6-dimethylphenoxy acetic acid using standard coupling procedures to give the desired compound.

$^1$H NMR (CDCl$_3$) δ 1.5–2.13 (m, 8H), 2.18 (s, 6H), 2.6–3.4 (m, 6H), 3.7–3.8 (m, 1H), 3.90–4.15 (m, 2H), 4.15–4.2 (m, 2H), 4.95–5.1 (m, 2H), 7.05–6.9 (m, 3H), 7.1–7.37 (m, 13H). Mass spectrum: (M+H)$^+$=623.

EXAMPLE 30

(2S,3S,5S)-2-(2,6-Dimethylphenoxyacetyl)amino-5-(3(R,S)-tetrahydrothienyloxycarbonyl)amino-1,6-diphenyl-3-hydroxyhexane A. (2S,3S,5S)-2-(t-butloxycarbonylamino)-5-(3(R,S)-tetrahydrothienyloxycarbonyl)amino-1,6-diphenyl-3-hydroxyhexane. 3(R,S)-tetrahydrothienyl pyridyl carbonate is prepared according to the procedure reported by Merck US94/01370. To a solution of carbonate in methylene chloride was added (2S,3S,5S)-2-amino-3-hydroxy-5-(t-butyloxycarbonylamino)-1,6-diphenylhexane. The resulting solution was stirred for 12 h. After washing with 10% aqueous citric acid, sodium bicarbonate and one portion of saturated brine, the solution was dried over $Na_2SO_4$ and concentrated in vacuo. The residue was purified by silica gel chromatography to provide the desired compound.

B. (2S,3S,5S)-2-(2,6-Dimethylphenoxyacetyl)amino-5-(3 (R,S)-tetrahydrothienyloxycarbonyl)amino-1,6-diphenyl-3-hydroxyhexane. The Boc protecting group of the compound from Example 27A was removed using trifuoroacetic acid in methylene chloride and the resulting (2S,3S,5S)-2-amino-5-(3(R,S)-tetrahydrothienyloxycarbonyl)amino-1,6-diphenyl-3-hydroxyhexane coupled with 2,6-dimethylphenoxy acetic acid using standard coupling procedures to yield the desired compound. $^1$H NMR (CDCl$_3$) δ 1.57–1.75 (m, 4H), 1.82–2.0 (m, 1H), 2.17 (m, 6H), 2.73–3.10 (m, 11H), 4.12–4.25 (m, 4H), 3.90–4.03 (m, 1H), 4.77–4.85 (m, 1H), 5.4–5.42 (m, 1H), 6.9–7.05 (m, 3H), 7.1–7.37 (m, 13H). Mass spectrum: (M+H)$^+$=577.

EXAMPLE 31

(2S,3S,5S)-2-(2,6-Dimethylphenoxyacetyl)amino-5-(3(R,S)-tetrahydrothiopyranyloxycarbonyl)amino-1, 6-diphenyl-3-hydroxyhexane The Boc protecting group of the compound from Example 29A was removed using trifuoroacetic acid in methylene chloride and the resulting (2S,3S,5S)-2-amino-5-(3(R,S)-tetrahydrothiopyranyloxycarbonyl)amino-1,6-diphenyl-3-hydroxyhexane coupled with 2,6-dimethylphenoxy acetic acid using standard coupling procedures to yield the desired compound.

$^1$H NMR (CDCl$_3$) δ 1.5–2.0 (br m, 5H), 2.05–2.15 (m, 1H), 2.18 (s, 6H), 2.45–2.55 (m, 3H), 2.65–2.85 (m, 4H), 2.95–3.0 (d, 2H), 3.4–3.53 (m, 1H), 3.7–3.8 (m, 1H), 3.9–4.0 (m, 1H), 4.1–4.1–4.22 (m, 2H), 4.7–4.8 (m, 2H), 6.9–7.05 (m, 3H), 7.1–7.37 (m, 13H). Mass spectrum: (M+H)$^+$=591.

EXAMPLE 32

(2S,3S,5S)-2-(2,6-Dimethylphenoxyacetyl)amino-5-(3R-2,2-dimethyl-tetrahydrothienyloxycarbonyl) amino-1,6-diphenyl-3-hydroxyhexane A. 2,2-Dimethyl-3R-hydroxy-tetrahydothiophene: The 2,2-Dimethyl-tetrahydrothiophene-3-one was prepared substantially in accordance with the procedure described in Merck US94/01370 except that ethyl-2-bromoisobutyrate was used in place of ethyl-2-bromoisovalerate. The ketone from the above experiment was combined in THF with the oxazaborolidine catalyst (prepared as described by Mathre, et. al. JOC 1991, 56, 751–762) and cooled to −15° C. Then, BH$_3$.DMS was added dropwise to a rapidly stirring solution. The reaction mixture was stirred for 1 hour and quenched by the cautious addition of methanol. The crude reaction mixture was concentrated in vacuo to an oil, and then azeotroped with methanol. The product was purified by flash chromatography using 20% ethyl acetate in hexane to provide the alcohol in 75% yield. $^1$H NMR (CDCl$_3$) δ 1.37 (d, 6H) 2.10 (m, 1H), 2.28 (m, 1H), 2.95 (m, 2H), 3.89 (m, 1H).

B. (2S,3S,5S)-2-(t-butyloxycarbonylamino)-5-(3R-2,2-dimethyl-tetrahydrothienyloxycarbonyl)amino-1,6-diphenyl-3-hydroxyhexane: 2,2-Dimetlyl-3R-tetrahydrothienyl pyridyl carbonate was prepared according to the procedure reported by Merck US94/01370. To a solution of carbonate in methylene chloride was added (2S,3S,5S)-2-amino-3-hydroxy-5-(t-butyloxycarbonylamino)-1,6-diphenylhexane. The resulting solution was stirred for 12 h. After washing with 10% aqueous citric acid, sodium bicarbonate and one portion of saturated brine, the solution was dried over $Na_2SO_4$ and concentrated in vacuo. The residue was purified by silica gel chromatography to provide the desired compound.

C. (2S,3S,5S)-2-(2,6-Dimethylphenoxyacetyl)amino-5-(3 (R,S)-tetrahydrothienyloxycarbonyl)amino-1,6-diphenyl-3-hydroxyhexane: The Boc protecting group of the compound from Example 32B was removed using trifuoroacetic acid in methylene chloride and the resulting (2S,3S,5S)-2-amino-5-(2,2-dimethyl-3R-tetrahydrothienyloxycarbonyl)amino-1, 6-diphenyl-3-hydroxyhexane coupled with 2,6-dimethylphenoxy acetic acid using standard coupling procedures to yield the desired compound.

EXAMPLE 33

(2S,3S,5S)-2-(2,6-Dimethylphenoxyacetyl)amino-5-(3R-2,2-dimethyl-1,1-dioxy-tetrahydrothienyloxycarbonyl)amino-1,6-diphenyl-3-hydroxyhexane.

A. (2S,3S,5S)-2-(t-butyloxycarbonylamino)-5-(2,2-dimethyl-1,1-dioxo-3R-tetrahydrothienyloxycarbonyl) amino-1,6-diphenyl-3-hydroxyhexane: To a solution of compound from Example 32B in acetone and water was added Oxone™ and sodium bicarbonate. The resulting solution was stirred for 2 h. After partition between ethyl acetate and aqueous sodium bisulfite, the organic layer was washed with sodium bicarbonate and one portion of saturated brine. The solution was dried over $Na_2SO_4$ and concentrated in vacuo. The residue was purified by silica gel chromatography eluted with methanol and chloroform to provide the desired compound.

B. (2S,3S,5S)-2-(2,6-Dimethylphenoxyacetyl)amino-5-(1,1-dioxo-3(R,S)-2(R,S)-isopropyl-tetrahydrothienyloxycarbonyl)amino-1,6-diphenyl-3-hydroxyhexane: The Boc protecting group of the compound from Example 33A was removed using trifuoroacetic acid in methylene chloride and the resulting (2S,3S,5S)-2-amino-5-(2,2-dimethyl-1,1-dioxo-3R-tetrahydrothienyloxycarbonyl)amino-1,6-diphenyl-3-hydroxyhexane coupled with 2,6-dimethylphenoxy acetic acid using standard coupling procedures to give the desired compound $^1$H NMR (CDCl$_3$) δ 1.25 (s, 3H), 1.47 (s, 3H), 1.8–1.6 (m, 3H), 1.9–2.07 (m, 1H), 2.17 (s, 6H), 2.30–2.45 (m, 1H), 2.77–2.85 (d, 2H), 2.96–3.04 (d, 2H) 3.1–3.2 (m, 2H), 3.95–4.07(m, 1H), 4.15–4.25 (m, 3H), 5.0–5.1 (dd, 2H), 6.97–7.05 (m, 3H), 7.1–7.37 (m, 13H). Mass spectrum: (M+H)$^+$=637.

EXAMPLE 34

(2S,3S,5S)-5-(N-(N-((N-Methyl-N-((2-isopropyl-4-thiazolyl)methyl)amino)carbonyl)-L-valinyl)amino)-2-((3R,3aS,6aR), (3S,3aR,6aS)-bis-tetrahydrofuran-3-yl-oxycarbonyl)amino-1,6-diphenyl-3-hydroxyhexane A. (2S,3S,5S)-2-((3R,3aS,6aR), (3S,3aR,6aS)-bis-tetrahydrofuran-3-yl-oxycarbonyl)amino-3-hydroxy-5-(t-butyloxycarbonylamino)-1,6-diphenylhexane: The desired compound was prepared according to the procedure described in Example 1 except that a mixture of 3-hydroxyl-(3R,3aS,6aR), (3S,3aR,6aS)-bis-tetrahydrofuran was used in place of 3-hydroxyl-(3R,3aS,6aR)-bis-tetrahydrofuran.

B. (2S,3S,5S)-5-(N-(N-((N-Methyl-N-((2-isopropy-4-thiazolyl)methyl)amino)carbonyl)-L-valinyl)amino)-2-

43

((3R,3aS,6aR), (3S,3aR,6aS)-bis-tetrahydrofuran-3-yl-oxycarbonyl)amino-1,6-diphenyl-3-hydroxyhexane: The Boc protecting group of the compound from Example 34A was removed using trifuoroacetic acid in methylene chloride and the resulting (2S,3S,5S)-5-amino-2-((3R,3aS,6aR), (3S,3aR,6aS)-bis-tetrahydrofuran-3-yl-oxycarbonyl)amino-1,6-diphenyl-3-hydroxyhexane coupled with N-((N-methyl-N-((2-isopropyl-4-thiazolyl)methyl)amino)carbonyl)-L-valine using standard coupling procedures to give the desired compound. $^1$H NMR (CDCl$_3$) δ 0.83 (d, J=6.0 Hz, 6H), 0.92 (d, J=6.0 Hz, 6H), 1.37 (d, J=6.0 Hz, 12H), 1.60 (m, 2H), 1.67 (m, 2H), 1.85 (m, 2H), 2.01 (m, 2H,), 2.31 (m, 2H), 2.74 (m, 6H), 2.85 (m, 4H), 2.93 (m, 2H), 2.99 (s, 6H), 3.26 (m, 2H), 3.60–3.78 (m, 8H), 3.85 (m, 2H), 3.95–4.02 (m, 4H), 4.20 (m, 2H), 4.38 (AB, J=15.0 Hz, 4H), 5.04 (m, 2H), 5.12 (dd, J=3.9, 3.3 Hz, 2H), 5.68 (d, J=5.7 Hz, 1H), 5.70 (d, J=5.7 Hz, 1H), 6.38 (bs, 2H), 6.57 (d, J=9.0 Hz, 1H), 6.60 (d, J=9.0 Hz, 1H), 7.12–7.29 (m, 22H). Mass spectrum: (M+H)$^+$=736.

EXAMPLE 35

(2S,3S,5S)-2-((5-Thiazolyl)methoxycarbonyl)amino-5-((3R,3aS,6aR), (3S,3aR,6aS)-bis-tetrahydrofuran-3-yl-oxycarbonyl)amino-1,6-diphenyl-3-hydroxyhexane (2S,3S,5S)-5-Amino-2-(N-((5-thiazolyl)methoxycarbonyl)amino)-1,6-diphenyl-3-hydroxyhexane dihydrochloride was synthesized according PCT Patent Application No. WO94/14436, published Jul. 7, 1994. The amine was reacted with ((3R,3aS,6aR), (3S,3aR,6aS)-bis-tetrahydrofiuran-3-yl-oxycarbonyl)oxy-4-nitro benzene using procedure Example 1B to yield the desired compound. $^1$H NMR (CDCl$_3$) δ 1.60–1.68 (m, 4H), 1.85 (m, 1H), 1.91 (m, 1H), 2.69–2.80 (m, 4H), 2.86 (m, 4H), 2.97 (m, 2H), 3.68 (m, 4H), 3.97 (m, 4H), 4.75 (d, J=9.0 Hz, 1H), 4.80 (d, J=9.0 Hz, 1H), 5.05 (m, 4H), 5.25 (s, 2H), 5.26 (s, 2H), 5.68 (d, J=5.7 Hz, 1H), 5.70 (d, J=5.7 Hz, 1H), 7.09 (m, 4H), 7.13–7.28 (m, 16H), 7.75 (s, 2H), 8.80 (s, 2H). Mass spectrum: (M+H)$^+$=582.

EXAMPLE 36

(2S,3S,5S)-5-(N-(N-((2-Isopropyl-4-thiazolyl)methyl)oxyqarbonyl)-D-valinyl)amnino)-2-((3R,3aS,6aR), (3S,3aR,6aS)-bis-tetrahydrofuran-3-yl-oxycarbonyl)amino-1,6-diphenyl-3-hydroxyhexane (2S,3S,5S)-5-Amino-2-((3R,3aS,6aR), (3S,3aR,6aS)-bis-tetrahydrofuran-3-yl-oxycarbonyl)amino-1,6-diphenyl-3-hydroxyhexane from Example 34B was coupled with N-((2-isopropyl-4-thiazolyl)methyl)oxycarbonyl)-D-valine using standard coupling procedures to give the desired compound. $^1$H NMR (CDCl$_3$) δ 0.78 (m, 12H), 1.39 (dm, J=6.0 Hz, 12H), 1.60–1.75 (m, 8H), 1.88 (m, 4H), 2.00 (m, 2H), 2.77 (m, 6H), 2.82 (d, J=7.5 Hz, 4H), 2.94 (m, 1H), 3.01 (m, 1H), 3.32 (m, 2H), 3.63 (m, 6H), 3.86 (m, 4H), 3.98 (m, 4H), 4.23 (m, 2H), 4.32 (m, 2H), 5.06 (m, 4H), 5.17 (m, 8H), 5.68 (d, J=5.7 Hz, 1H), 5.70 (d, J=5.7 Hz, 1H), 6.01 (m, 2H), 7.01–7.28 (m, 22H). Mass spectrum: (M+H)$^+$=723.

EXAMPLE 37

(2S,3S,5S)-5-(N-(N-((2-Isopropyl-4-thiazolyl)methy)oxycarbonyl)-L-valinyl)amino)-2-((3R,3aS,6aR), (3S,3aR,6aS)-bis-tetrahydrofuran-3-yl-oxycarbonyl)amino-1,6-diphenyl-3-hydroxyhexane (2S,3S,5S)-5-Amino-2-((3R,3aS,6aR), (3S,3aR,6aS)-bis-tetrahydrofuran-3-yl-oxycarbonyl)amino-1,6-diphenyl-3-hydroxyhexane from Example 34B was coupled with N-((2-isopropyl-4-thiazolyl)methyl)oxycarbonyl)-L-valine using standard coupling procedures to give the desired compound. $^1$H NMR (CDCl$_3$) δ 0.68 (m, 6H), 0.87 (m, 6H), 1.41 (d, J=7.5 Hz, 12H), 1.58–1.73 (m, 8H), 1.83 (m, 2H), 2.00 (m, 2H), 2.17 (m, 4H), 2.78 (m, 6H), 2.83 (m, 4H), 2.93 (m, 2H), 3.47 (m, 2H), 3.63 (m, 4H), 3.72 (m, 4H), 3.87 (m, 4H), 3.98 (m, 4H), 4.18 (m, 4H), 5.05 (AB, J=15.0 Hz, 2H), 5.09 (m, 2H), 5.17 (AB, J=15.0 Hz, 2H), 5.67 (d, J=5.7 Hz, 1H), 5.70 (d, J=5.7 Hz, 1H), 6.22 (m, 2H), 7.12 (m, 4H), 7.18–7.28 (m, 18H). Mass spectrum: (M+H)$^+$=723.

EXAMPLE 38

(2S,3S,5S)-2-((5-Thiazolyl)methoxycarbonyl)amino-5-((3S,3aR,6aS)-bis-tetrahydrofuran-3-yl-oxycarbonyl)amino-1,6-diphenyl-3-hydroxyhexane (2S,3S,5S)-5-Amino-2-(N-((5-thiazolyl)methoxycarbonyl)amino)-1,6-diphenyl-3-hydroxyhexane dihydrochloride was reacted with ((3S,3aR,6aS)-bis-tetrahydrofuran-3-yl-oxycarbonyl)oxy-4-nitro benzene using procedure Example 1B to give the desired compound. $^1$H NMR (CDCl$_3$) δ 1.63 (m, 4H), 2.68 (m, 1H), 2.81 (m, 1H), 2.87 (d, J=7.5 Hz, 2H), 2.97 (m, 2H), 3.69 (m, 3H), 3.86 (m, 2H), 3.97 (m, 2H), 4.79 (d, J=8.4 Hz, 1H), 5.09 (m, 2H), 5.75 (s, 2H), 5.68 (d, J=5.7 Hz, 1H), 7.09 (m, 2H), 7.17–7.28 (m, 8H), 7.86 (s, 1H), 8.80 (s, 1H). Mass spectrum: (M+H)$^+$=582.

EXAMPLE 39

(2S,3S,5S)-5-(N-(N-((N-Methyl-N-((2-isopropv-4-thiazolyl)methyl)amino)carbonyl)-D-valinvyl)amino)-2-((3R,3aS,6aR), (3S,3aR,6aS)-bis-tetrahydrofuran-3-yl-oxycarbonyl)amino-1,6-diphenyl-3-hydroxyhexane (2S,3S,5S)-5-Amino-2-((3R,3aS,6aR), (3S,3aR,6aS)-bis-tetrahydrofuran-3-yl-oxycarbonyl)amino-1,6-diphenyl-3-hydroxyhexane from Example 34B was coupled with N-((N-methyl-N-((2-isopropyl-4-thiazolyl)methyl)amino)carbonyl)-D-valine using standard coupling procedures to give the desired compound. $^1$H NMR (CDCl$_3$) δ 0.84 (d, J=6.0 Hz, 3H), 0.87 (d, J=6.0 Hz, 3H), 0.92 (d, J=6.0 Hz, 3H), 0.96 (d, J=6.0 Hz, 3H), 1.48 (dm, J=6.0 Hz, 12H), 1.62 (m, 2H), 1.67 (m, 2H), 1.85 (m, 2H), 2.00 (m, 4H), 2.67 (m, 2H), 2.77 (m, 6H), 2.85 (m, 2H), 2.93 (m, 2H), 2.98 (s, 6H), 3.02 (m, 2H), 3.27 (m, 2H), 3.45 (m, 2H), 3.61 (m, 4H), 3.87 (m, 2H), 3.99 (m, 2H), 4.27 (m, 2H), 4.35 (AB, J=15.0 Hz, 2H), 4.51 (AB, J=15.0 Hz, 2H), 5.07 (m, 2H), 5.15 (m, 2H), 5.69 (d, J=5.7 Hz, 1H), 5.70 (d, J=5.7 Hz, 1H), 6.21(d, J=9.0 Hz, 2H), 6.33 (bs, 2H), 6.99 (s, 2H), 7.12–7.22 (m, 20H). Mass spectrum: (M+H)$^+$=736.

EXAMPLE 40

(2S,3S,5S)-5-((5-Thiazolyl)methoxycarbonyl)amino-2-((3R,3aS,6aR), (3S,3aR,6aS)-bis-tetrahydrofuran-3-yl-oxycarbonyl)amino-1,6-diphenyl-3-hydroxyhexane (2S,3S,5S)-5-Amino-2-((3R,3aS,6aR), (3S,3aR,6aS)-bis-tetrahydrofuran-3-yl-oxycarbonyl)amino-1,6-diphenyl-3-hydroxyhexane from Example 34B was coupled with 5-(4-Nitrophenoxycarbonyloxymethyl)thiazole using procedure Example 1B to give the desired compound. $^1$H NMR (CDCl$_3$) δ 1.58–1.70 (m, 8H), 1.82 (m, 1H), 1.99 (m, 1H), 2.78 (m, 4H), 2.85 (m, 4H), 2.97 (m, 4H), 3.60–3.78 (m, 6H), 3.85 (m, 2H), 3.98 (m, 4H), 4.80 (d, J=9.0 Hz, 2H), 5.02 (m, 4H), 5.23 (s, 4H), 5.68 (d, J=5.7 Hz, 1H), 5.70 (d, J=5.7 Hz, 1H), 7.08 (m, 4H), 7.15–7.30 (m, 16H), 7.85 (s, 2H), 8.82 (s, 2H). Mass spectrum: (M+H)$^+$=582.

EXAMPLE 41

(2S,3S,5S)-2,5-((3R,3aS,6aR)-bis-Tetrahydrofuran-3-yl-oxycarbonyl)amino-1,6-diphenyl-3-hydroxyhexane (2S,3S,5S)-5-Amino-2-((3R,3aS,6aR), (3S,3aR,6aS)-bis-tetrahydrofuran-3-oxycarbonyl)amino-1,6-diphenyl-3-hydroxyhexane from Example 34B was coupled with ((3R,3aS,6aR), (3S,3aR,6aS)-bis-tetrahydrofuran-3-yl-oxycarbonyl)oxy-4-nitro benzene using procedure Example 1B to give the desired compound. $^1$H NMR (CDCl$_3$) δ 1.68 (m, 16H), 1.87 (m, 4H), 1.97 (m, 4H), 2.72 (m, 4H), 2.80 (m, 8H), 2.86 (m, 8H), 2.99 (m, 8H), 3.65–3.77 (m, 16H), 3.82–3.90 (m, 8H), 4.08 (m, 4H), 5.00 (m, 4H), 5.08 (m, 8H), 5.69 (m, 8H), 7.11 (m, 8H), 7.18–7.23 (m, 32H). Mass spectrum: (M+H)$^+$=597.

EXAMPLE 42

(2S,3S,5S)-5-(N-(N-((5-Thiazolyl)methoxycarbonyl)-L-valinyl)amino)-2-((3R,3aS,6aR)-bis-tetrahydrofuran-3-yl-oxycarbonyl)amino-1,6-diphenyl-3-hydroxyhexane (2S,3S,5S)-5-Amino-2-((3R,3aS,6aR)-bis-tetrahydrofuran-3-yl-oxycarbonyl)amino-1,6-diphenyl-3-hydroxyhexane from Example 1C was coupled with N-(((5-thiazolyl)methyl)oxycarbonyl)-L-valine using standard coupling procedures to give the desired compound. $^1$H NMR (CDCl$_3$) δ 0.77 (d, J=6.0 Hz, 6H), 1.38 (m, 1H), 1.45 (m, 2H), 1.83 (m, 1H), 2.53 (m, 1H), 2.62 (m, 1H), 2.67 (m, 2H), 2.78 (m, 1H), 3.48 (m, 2H), 3.52 (dd, J=9.0, 6.0 Hz, 1H), 3.61 (m, 2H), 3.77 (m, 2H), 3.82 (m, 2H), 4.15 (m, 1H), 4.63 (d, J=6.0 Hz, 1H), 4.83 (m, 1H), 5.28 (s, 2H), 5.51 (d, J=5.7 Hz, 1H), 6.87 (d, J=9.0 Hz, 1H), 7.12–7.21 (m, 10H), 7.79 (d, J=9.0 Hz, 1H), 7.93 (s, 1H), 9.09 (s, 1H). Mass spectrum: (M+H)$^+$=681.

EXAMPLE 43

(2S,3S,5S)-5-(N-(N-((5-Thiazolyl)methoxycarbonyl)-D-valinyl)amino)-2-((3R,3aS,6aR)-bis-tetrahydrofuran-3-yl-oxycarbonyl)amino-1,6-diphenyl-3-hydroxyhexane (2S,3S,5S)-5-Amino-2-((3R,3aS,6aR)-bis-tetrahydrofuran-3-yl-oxycarbonyl)amino-1,6-diphenyl-3-hydroxyhexane from Example 1C was coupled with N-(((5-thiazolyl)methyl)oxycarbonyl)-D-valine using standard coupling procedures to give the desired compound. $^1$H NMR (DMSO-d$_6$) δ 0.58 (d, J=6.0 Hz, 3H), 0.61 (d, J=6.0 Hz, 3H), 1.36 (m, 1H), 1.49 (m, 2H), 1.71 (m, 1H), 2.56 (m, 1H), 2.67 (m, 2H), 2.75 (m, 1H), 3.01 (m, 2H), 3.55 (dd, J=9.0, 6.0 Hz, 1H), 3.61 (m, 2H), 3.72 (m, 2H), 3.85 (dd, J=9.0, 6.0 Hz, 1H), 3.90 (m, 1H), 4.27 (m, 1H), 4.61 (d, J=6.0 Hz, 1H), 4.86 (m, 1H), 5.22 (AB, J=15.0 Hz, 2H), 5.51 (d, J=5.7 Hz, 1H), 6.01 (m, 1H), 6.86 (d, J=9.0 Hz, 1H), 7.11–7.22 (m, 10H), 7.75 (d, J=9.0 Hz, 1H), 7.89 (s, 1H), 9.03 (s, 1H). Mass spectrum: (M+H)$^+$=681.

EXAMPLE 44

(2S,3S,5S)-5-(N-(N-((N-Methyl-N-((5-thiazolyl)methyl)amino)carbonyl)-D-valinyl)amino)-2-((3R,3aS,6aR)-bis-tetrahydrofuran-3-yl-oxycarbonyl)amino-1,6-diphenyl-3-hydroxyhexane (2S,3S,5S)-5-Amino-2-((3R,3aS,6aR)-bis-tetrahydrofuran-3-yl-oxycarbonyl)amino-1,6-diphenyl-3-hydroxyhexane from Example 1C was coupled with N-((5-thiazolylmethyl)amino)carbonyl-D-valine using standard coupling procedures to give the desired compound. $^1$H NMR (CDCl$_3$) δ 0.78 (d, J=6.0 Hz, 3H), 0.87 (d, J=6.0 Hz, 3H), 1.63 (m, 2H), 1.69 (m, 2H), 2.13 (m, 2H), 2.80 (d, J=6.6 Hz, 2H), 2.84 (m, 2H), 2.89 (s, 3H), 2.93 (m, 2H), 3.63 (m, 1H), 3.73 (m, 2H), 3.88 (dt, J=8.7, 3.0 Hz, 1H), 3.99 (m, 2H), 4.18 (m, 1H), 4.68 (AB, J=15.0 Hz, 2H), 4.73 (m, 1H), 5.07 (m, 2H), 5.68 (d, J=5.7 Hz, 1H), 6.27 (d, J=9.0 Hz, 1H), 7.12–7.28 (m, 10H), 7.78 (s, 1H), 8.77 (s, 1H). Mass spectrum: (M+H)$^+$=694.

EXAMPLE 45

(2S,3S,5S)-5-(N-(N-((N-Methyl-N-((5-thiazolyl)methyl)amino)carbonyl)-L-valinyl)amino)-2-((3R,3aS,6aR)-bis-tetrahydrofuran-3-yl-oxycarbonyl)amino-1,6-diphenyl-3-hydroxyhexane (2S,3S,5S)-5-Amino-2-((3R,3aS,6aR)-bis-tetrahydrofuran-3-yl-oxycarbonyl)amino-1,6-diphenyl-3-hydroxyhexane from Example 1C was coupled with N-(5-thiazolylmethyl)amino)carbonyl-L-valine using standard coupling procedures to give the desired compound. $^1$H NMR (CDCl$_3$) δ 0.68 (d, J=6.0 Hz, 3H), 0.85 (d, J=6.0 Hz, 3H), 1.64 (m, 2H), 1.68 (m, 2H), 2.14 (m, 2H), 2.80 (d, J=6.6 Hz, 2H), 2.83 (m, 2H), 2.89 (s, 3H), 2.90 (m, 2H), 3.62–3.71 (m, 3H), 3.88 (m, 1H), 4.01 (m, 2H), 4.20 (m, 1H), 4.68 (AB, J=15.0 Hz, 2H), 4.73 (m, 1H), 5.07 (m, 2H), 5.68 (d, J=5.7 Hz, 1H), 6.45 (d, J=9.0 Hz, 1H), 7.12–7.28 (m, 10H), 7.82 (s, 1H), 8.91 (s, 1H). Mass spectrum: (M+H)$^+$=694.

EXAMPLE 46

(2S,3S,5S)-2-(N-(N-((N-Methyl-N-((2-isopropyl-4-thiazolyl)methyl)amino)carbonyl)-L-valinyl)amino)-5-((3R,3aS,6aR)-bis-tetrahydrofuran-3-yl-oxycarbonyl)amino-1,6-diphenyl-3-hydroxyhexane A. (2S,3S,5S)-2-(N-(N-(N-Methyl-N-((2-isopropyl-4-thiazolyl)methyl)amino)carbonl)-L-valinyl)amino)-5-(t-butyloxycarbonylamino)-1,6-diphenyl-3-hydroxyhexane: (2S,3S,5S)-2-Amino-3-hydroxy-5-(t-butyloxycarbonylamino)-1,6-diphenylhexane was coupled with N-((N-methyl-N-((2-isopropyl-4thiazolyl)methyl)amino)carbonyl)-L-valine using standard coupling procedures to give the desired compound.

B. (2S,3S,5S)-2-(N-(N-((N-Methyl-N-((2-isopropyl-4-thiazolyl)methyl)amino)carbonyl)-L-valinyl)amino)-5-((3R,3aS,6aR)-bis-Tetrahydrofuran-3-yl-oxycarbonyl)amino-1,6-diphenyl-3-hydroxyhexane: The Boc protecting group of compound from Example 46A was removed by treating with TFA and the resulting amine was coupled with ((3R,3aS,6aR)-bis-tetrahydrofuran-3-yl-oxycarbonyl)oxy-4-nitro benzene using the procedure described in Example 1B to give the desired compound. $^1$H NMR (CDCl$_3$) δ 0.86 (d, J=6.0 Hz, 3H), 0.97 (d, J=6.0 Hz, 3H), 1.37 (dd, J=6.0, 3.0 Hz, 6H), 1.67 (m, 4H), 2.28 (m, 1H), 2.77 (m, 2H), 2.83 (dd, J=6.3, 3.0 Hz, 2H), 2.96 (m, 1H), 2.97 (s, 3H), 3.13 (quart, J=7.5 Hz, 2H), 3.27 (hept, J=6.6 Hz, 1H), 3.47 (m, 1H), 3.68 (m, 2H), 3.72 (m, 1H), 3.88 (dt, J=9.0, 3.0 Hz, 1H), 3.95 (m, 1H), 4.00 (m, 1H), 4.10 (m, 1H), 4.40 (AB, J=15.0 Hz, 2H), 5.08 (dd, J=6.6, 3.0 Hz, 1H), 5.17 (d, J=8.7 Hz, 1H), 5.67 (d, J=5.7 Hz, 1H), 6.35 (m, 1H), 6.54 (d, J=9.0 Hz, 1H), 7.00 (s, 1H), 7.11–7.28 (m, 10H). Mass spectrum: (M+H)$^+$=736.

EXAMPLE 47

(2S,3S,5S)-5-(N-(N-(N-Methyl-N-((2-methyl-4-thiazolyl)methyl)amino)carbonyl)-L-valinyl)amino)-2-((3S,3aR,6aS)-bis-tetrahydrofuran-3-yl-oxycarbonyl)amino-1,6-diphenyl-3-hydroxyhexane (2S,3S,5S)-5-Amino-2-((3S,3aR,6aS)-bis-tetrahydrofuran-3-yl-oxycarbonyl)amino-1,6-diphenyl-3- hydroxyhexane from Example 2C was coupled with N-(N-Methyl-N-((2-methyl-4-thiazolyl)methyl)amino)carbonyl-L-valine using standard coupling procedures to give the desired compound. $^1$H NMR (CDCl$_3$) δ 0.81 (d, J=6.0 Hz, 3H), 0.93 (d, J=6.0 Hz, 3H), 1.60 (m, 2H), 1.67 (m, 2H), 1.87 (m, 1H), 2.00 (m, 1H), 2.33 (m, 1H), 2.67 (s, 3H), 2.76 (d, J=7.2 Hz, 2H), 2.85 (t, J=6.0 Hz, 2H), 2.98 (s, 3H), 3.01 (m, 1H), 3.60 (dd, J=9.6, 6.3 Hz, 1H), 3.67 (m, 1H), 3.73 (m, 1H), 3.86 (m, 1H), 3.97 (m, 2H), 4.03 (m, 2H), 4.35 (d, J=6.0 Hz, 2H), 5.05 (quart, J=6.9 Hz, 1H), 5.13 (d, J=9.0 Hz, 1H), 5.70 (d, J=5.7 Hz, 1H), 6.51 (d, J=9.0 Hz, 1H), 7.00 (s, 1H), 7.08–7.22 (m, 10H). Mass spectrum: (M+H)$^+$=708.

EXAMPLE 48

(2S,3S,5S)-5-(N-(N-((N-Methyl-N-((2-isopropyl-4-thiazolyl)methyl)amino)carbonyl)-L-valinyl)amino)-2-((3S,3aR,6aS)-bis-tetrahydrofuran-3-yl-oxycarbon, amino-1,6-diphenyl-3-hydroxyhexane (2S,3S,5S)-5-Amino-2-((3S,3aR,6aS)-bis-tetrahydrofuran-3-yl-oxycarbonyl)amino-1,6-diphenyl-3-hydroxyhexane from Example 2C was coupled with N-(N-methyl-N-((2-isopropyl-4-thiazolyl)methyl)amino) carbonyl-L-valine using standard coupling procedures to give the desired compound. $^1$H NMR (CD$_3$OD) δ 0.82 (d, J=6.0 Hz, 3H), 0.86 (d, J=6.0 Hz, 3H), 1.37 (d, J=6.6 Hz, 6H), 1.61 (m, 1H), 1.67 (m, 2H), 1.81 (m, 1H), 1.87 (m, 1H), 1.92 (m, 1H), 2.00 (m, 2H), 2.70 (m, 1H), 2.77 (m, 2H), 2.80 (m, 2H), 2.97 (s, 3H), 3.50 (m, 1H), 3.53 (m, 1H), 3.71 (m, 1H), 3.86 (m, 1H), 3.89 (m, 1H), 3.95 (m, 2H), 4.30 (m, 1H), 4.50 (AB, J=15.0 Hz, 2H), 5.61 (d, J=5.7 Hz, 1H), 7.12–7.18 (m, 8H), 7.23 (m, 3H). Mass spectrum: (M+H)$^+$=736.

EXAMPLE 49

(2S,3S,5S)-5-(N-(N-((N-Methyl-N-(2-methyl-4-thiazolyl)methyl)amino)carbonyl)-L-valinyl)amino)-2-((3R,3aS,6aR)-bis-tetrahydrofuran-3-yl-oxycarbonyl)amino-1,6-diphenyl-3-hydroxyhexane (2S,3S,5S)-5-Amino-2-((3S,3aR,6aS)-bis-tetrahydrofuran-3-yl-oxycarbonyl)amino-1,6-diphenyl-3-hydroxyhexane from Example 2C was coupled with N-(N-methyl-N-((2-methyl-4-thiazolyl)methyl)amino)carbonyl-L-valine using standard coupling procedures to give the desired compound. $^1$H NMR (CD$_3$OD) δ 0.85 (d, J=6.0 Hz, 6H), 1.38 (m, 1H), 1.49 (m, 1H), 1.59 (m, 1H), 1.64 (m, 1H), 1.97 (m, 1H), 2.64 (s, 3H), 2.71 (m, 2H), 2.77 (m, 2H), 2.87 (m, 1H), 2.94 (s, 3H), 3.63 (dd, J=9.0, 6.0 Hz, 2H), 3.73 (m, 2H), 3.89 (dd, J=9.6, 6.0 Hz, 1H), 3.96 (d, J=6.6 Hz, 1H), 4.00 (m, 1H), 4.32 (m, 1H), 4.99 (AB, J=15.0 Hz, 2H), 4.90 (m, 2H), 5.57 (d, J=5.7 Hz, 1H), 7.12–7.18 (m, 8H), 7.23 (m, 3H). Mass spectrum: (M+H)$^+$=708.

EXAMPLE 50

(2S,3S,5S)-5-(N-(N-((N-Methyl-N-((2-isoprolpyl-4-thiazolyl)methyl)amino)carbonyl)-L-valinyl)amino)-2-(3S-tetrahydrofuran-3-yl-oxycarbonyl)amino-1,6-diphenyl-3-hydroxyhexane A. (3S-Tetrahydrofuran-3-yl-oxycarbonyl)oxy-4-nitro-benzene: (3S-Tetrahydrofuran-3-yl-oxycarbonyl)oxy-4-nitro-benzene was synthesized according to the procedure described in Example 1A by replacing 3-hydroxyl-(3R,3aS, 6aR)-bis-tetrahydrofuran with 3S-hydroxy-tetrahydrofuran.

B. (2S,3S,5S)-2-(3S-Tetrahydrofuran-3-yl-oxyarbonyl) amino-3-hydroxy-5-(t-butyloxycarbonylamino)-1,6-diphenylhexane: (2S,3S,5S)-2-(3S-Tetrahydrofuran-3-yl-oxycarbonyl)amino-3-hydroxy-5-(t-butyloxycarbonylamino)-1,6-diphenylhexane was prepared using procedure Example 1B by addition of (3S-tetrahydrofuran-3-yl-oxycarbonyl)oxy-4-nitro-benzene instead of ((3R,3aS,6aR)-bis-tetrahydrofuran-3-yl-oxycarbonyl)oxy-4nitro benzene.

C. (2S,3S,5S)-5-(N-(N-((N-Methyl-N-((2-isopropyl-4-thiazolyl)methyl)amino)carbonyl)-L-valinyl)amino)-2-(3S-Tetrahydrofuran-3-yl-oxycarbonyl)amino-1,6-diphenyl-3-hydroxyhexane.

(2S,3S,5S)-5-Amino-2-(3S-Tetrahydrofuran-3-yl-oxycarbonyl)amino-1,6-diphenyl-3-hydroxyhexane from Example 50B was coupled with N-(N-methyl-N-((2-isopropyl-4-thiazolyl)methyl)amino)carbonyl-L-valine using standard coupling procedures to give the desired compound. $^1$H NMR (CDCl$_3$) δ 0.83 (d, J=6.0 Hz, 3H), 0.92 (d, J=6.0 Hz, 3H), 1.37 (d, J=6.0 Hz, 3H), 1.38 (d, J=6.0 Hz, 3H), 1.65 (m, 2H), 2.00 (m, 1H), 2.13 (m, 1H), 2.31 (m, 1H), 2.75 (m, 2H), 2.83 (dd, J=3.0, 6.6 Hz, 1H), 2.99 (s, 3H), 3.27 (m, 1H), 3.63 (m, 1H), 3.67 (m, 1H), 3.81 (dd, J=10.5, 4.5 Hz, 1H), 3.89 (m, 1H), 4.00 (m, 1H), 4.12 (m, 2H), 4.38 (AB, J=15.0 Hz, 2H), 5.07 (d, J=9.0 Hz, 1H), 5.16 (m, 1H), 6.55 (d, J=9.0 Hz, 1H), 7.01 (s, 1H), 7.08–7.23 (m, 12H). Mass spectrum: (M+H)$^+$=694.

EXAMPLE 51

(2S,3S,5S)-5-(N-(N-((N-Methyl-N-((2-isopropyl-4-thiazolyl)methyl)amino)carbonyl)-D-valinyl)amino)-2-((3R,3aS,6aR)-bis-tetrahydrofuran-3-yl-oxycarbonyl)amino-1,6-diphenyl-3-hydroxyhexane (2S,3S,5S)-5-Amino-2-((3R,3aS,6aR)-bis-tetrahydrofuran-3-yl-oxycarbonyl)amino-1,6-diphenyl-3-hydroxyhexane from Example 1C was coupled with N-(N-methyl-N-((2-isopropyl-4-thiazolyl)methyl)amino) carbonyl-L-valine using standard coupling procedures to give the desired compound. $^1$H NMR (CDCl$_3$) δ 0.81 (d, J=6.0 Hz, 3H), 0.92 (d, J=6.0 Hz, 3H), 1.36 (d, J=6.0 Hz, 3H), 1.37 (d, J=6.0 Hz, 3H), 1.62 (m, 2H), 1.69 (m, 2H), 2.31 (m, 1H), 2.75 (d, J=7.2 Hz, 2H), 2.85 (t, J=7.5 Hz, 2H), 2.93 (m, 1H), 2.99 (s, 3H), 3.27 (m, 1H), 3.68 (m, 1H), 3.73 (m, 1H), 3.79 (m, 2H), 3.89 (dt, J=7.8, 3.0 Hz, 1H), 4.00 (m, 2H), 4.22 (m, 2H), 4.38 (AB, J=15.0 Hz, 2H), 5.05 (quart, J=6.3 Hz, 1H), 5.10 (d, J=5.7 Hz, 1H), 6.35 (m, 1H), 6.55 (d, J=9.0 Hz, 1H), 7.02 (s, 1H), 7.12–7.23 (m, 10H). Mass spectrum: (M+H)$^+$=736.

EXAMPLE 52

(2S,3S,5S)-5-(N-(N-((N-Methyl-N-((2-methyl-4-thiazolyl)methyl)amino)carbonyl)-L-valinyl)amino)-2-((3R,3aS,6aR),(3S,3aR,6aS)-bis-tetrahydrofuran-3-yl-oxycarbonyl)amino-1,6-diphenyl-3-hydroxyhexane (2S,3S,5S)-5-Amino-2-((3S,3aR,6aS),(3S,3aR,6aS)-bis-tetrahydrofuran-3-yl-oxycarbonyl)amino-1,6-diphenyl-3-hydroxyhexane from Example 34A was coupled with N-(N-methyl-N-((2-methyl-4-thiazolyl)methyl)amino)carbonyl-L-valine using standard coupling procedures to give the desired compound. $^1$H NMR (CDCl$_3$) δ 0.80 (t, J=6.0 Hz, 6H), 0.93 (d, J=6.0 Hz, 6H), 1.25 (m, 2H), 1.62 (m, 6H), 2.67 (s, 6H), 2.31 (m, 2H), 2.76 (m, 4H), 2.83 (m, 6H), 2.99 (s, 6H), 3.02 (m, 2H), 3.54–3.78 (m, 8H), 3.87 (m, 2H), 3.95–4.02 (m, 4H), 4.25 (m, 4H), 4.36 (m, 4H), 5.05 (t, J=9.6 Hz, 2H), 5.67 (d, J=5.7 Hz, 1H), 5.70 (d, J=5.7 Hz, 1H), 6.38

(bs, 2H), 6.49 (d, J=9.0 Hz, 1H), 6.52 (d, J=9.0 Hz, 1H), 7.01 (s, 2H), 7.12–7.29 (m, 22H). Mass spectrum: (M+H)$^+$=708.

EXAMPLE 53

(2S,3S,5S)-5-(4-Hydroxy-benzoyl)amino-2-((3S, 3aR,6aS)-bis-tetrahydrofuran-3-yl-oxycarbonyl) amino-1,6-diphenyl-3-hydroxyhexane (2S,3S,5S)-5-Amino-2-((3S,3aR,6aS)-bis-tetrahydrofuran-3-yl-oxycarbonyl)amino-1,6-diphenyl-3-hydroxyhexane from Example 2C was coupled with 4-hydroxy-benzoic acid using standard coupling procedures to give the desired compound. $^1$H NMR (CD$_3$OD) δ 1.75 (m, 2H), 1.79 (m, 1H), 2.00 (m, 1H), 2.75 (m, 1H), 2.80 (m, 2H), 2.85 (t, J=9.0 Hz, 2H), 2.99 (m, 1H), 3.55 (dd, J=9.0, 6.0 Hz, 1H), 3.71 (dt, J=3.0, 6.6 Hz, 1H), 3.82 (m, 1H), 3.97 (m, 1H), 4.47 (m, 1H), 4.90 (m, 1H), 4.95 (m, 2H), 5.62 (d, J=5.7 Hz, 1H), 6.27 (d, J=9.0 Hz, 2H), 7.11–7.22 (m, 11H), 7.52 (d, J=9.0 Hz, 2H). Mass spectrum: (M+H)$^+$=561.

EXAMPLE 54

(2S,3S,5S)-5-(4-Acetoxy-benzoyl)amino-2-((3R, 3aS,6aR)-bis-tetrahydrofuran-3-yl-oxycarbonyl) amino-1,6-diphenyl-3-hydroxyhexane (2S,3S,5S)-5-Amino-2-((3R,3aS,6aR)-bis-tetrahydrofuran-3-yl-oxycarbonyl)amino-1,6-diphenyl-3-hydroxyhexane from Example 1C was coupled with 4-acetoxybenzoic acid using standard coupling procedures to give the desired compound. $^1$H NMR (CDCl$_3$) δ 1.22 (m, 2H), 1.68 (m, 1H), 1.78 (m, 2H), 2.31 (s, 3H), 2.88 (dd, J=6.3, 3.0 Hz, 2H), 2.93 (m, 3H), 3.71 (dd, J=10.5, 7.5 Hz, 2H), 3.79 (quart, J=8.1 Hz, 2H), 3.89 (dt, J=9.0, 4.5 Hz, 1H), 3.99 (dd, J=9.0, 6.0 Hz, 1H), 4.32 (m, 1H), 5.07 (AB, J=15.0 Hz, 2H), 5.67 (d, J=5.7 Hz, 1H), 6.20 (d, J=9.0 Hz, 1H), 7.12 (m, 9.0 Hz, 2H), 7.15–7.30 (m, 11H), 7.62 (d, J=9.0 Hz, 2H). Mass spectrum: (M+H)$^+$=461.

EXAMPLE 55

(2S,3S,5S)-5-(4-Hydroxy-benzoyl)amino-2-((3R, 3aS,6aR)-bis-tetrahydrofuran-3-yl-oxycarbonyl) amino-1,6-diphenyl-3-hydroxyhexane (2S,3S,5S)-5-Amino-2-((3R,3aS,6aR)-bis-tetrahydrofuran-3-yl-oxycarbonyl)amino-1,6-diphenyl-3-hydroxyhexane from Example 1C was coupled with 4-hydroxybenzoic acid using standard coupling procedures to give the desired compound. $^1$H NMR (CD$_3$OD) δ 1.29 (m, 1H0, 146 (m, 1H), 1.57 (m, 2H), 1.77 (m, 2H), 2.78 (m, 2H), 2.83 (m, 1H), 2.88 (2H), 2.92 (m, 1H), 3.35 (m, 1H), 3.67 (dd, J=10.5, 6.0 Hz, 2H), 3.71 (m, 1H), 3.79 (dt, J=9.0, 3.0 Hz, 1H), 3.91 (dd, J=10.5, 6.0 Hz, 1H), 4.07 (m, 1H), 4.51 (m, 1H), 4.91 (m, 2H), 4.95 (m, 1H), 5.59 (d, J=5.7 Hz, 1H), 6.90 (d, J=9.0 Hz, 1H), 7.08 (d, J=9.0 Hz, 2H), 7.11–7.28 (m, 10H). Mass spectrum: (M+H)$^+$=561.

EXAMPLE 56

(2S,3S,5S)-5-(4-Acetoxy-benzoyl)amino-2-((3S, 3aR,6aS)-bis-tetrahydrofuran-3-yl-oxycarbonyl) amino-1,6-diphenyl-3-hydroxyhexane (2S,3S,5S)-5-Amino-2-((3S,3aR,6aS)-bis-tetrahydrofuran-3-yl-oxycarbonyl)amino-1,6-diphenyl-3-hydroxyhexane from Example 2C was coupled with 4-acetoxybenzoic acid using standard coupling procedures to give the desired compound. $^1$H NMR (CD$_3$OD) δ 1.75 (m, 2H), 1.80 (m, 1H), 2.00 (m, 1H), 2.27 (s, 3H), 2.78 (m, 1H), 2.80 (m, 2H), 2.85 (m, 2H), 2.99 (m, 1H), 3.54 (dd, J=9.0, 6.0 Hz, 1H), 3.70 (m, 1H), 3.81 (m, 1H), 3.86 (m, 2H), 3.97 (m, 1H), 4.49 (m, 1H), 4.94 (m, 1H), 5.60 (d, J=5.7 Hz, 1H), 6.69 (d, J=9.0 Hz, 1H), 7.11 (d, J=9.0 Hz, 2H), 7.13–7.22 (m, 10H), 7.61 (d, J=9.0 Hz, 2H), 8.13 (J=9.0 Hz, 1H). Mass spectrum: (M+H)$^+$=603.

EXAMPLE 57

(2S,3S,5S)-5-(2-Chloro-4-hydroxy-benzoyl)amino-2-((3R,3aS,6aR)-bis-tetrahydrofuran-3-yl-oxycarbonyl)amino-1,6-diphenyl-3-hydroxyhexane (2S,3S,5S)-5-Amino-2-((3R,3aS,6a6)-bis-tetrahydrofuran-3-yl-oxycarbonyl)amino-1,6-diphenyl-3-hydroxyhexane from Example 1C was coupled with 2-chloro-4-hydroxybenzoic acid using standard coupling procedures to give the desired compound. $^1$H NMR (DMSO-d$_6$) δ 1.36 (m, 1H), 1.46 (m, 1H), 1.63 (m, 2H), 2.57 (m, 1H), 2.73 (m, 1H), 2.82 (m, 2H), 2.85 (m, 1H), 3.53 (dd, J=9.0, 6.0 Hz, 1H), 3.63 (m, 2H), 3.85 (m, 2H), 3.98 (m, 1H), 4.33 (m, 1H), 4.74 (d, J=6.0 Hz, 1H), 4.86 (m, 1H), 5.52 (d, J=5.7 Hz, 1H), 6.71 (dd, J=8.1, 2.1 Hz, 2H), 6.80 (d, J=2.1 Hz, 1H), 7.02 (d, J=8.1 Hz, 1H), 7.12–7.28 (m, 11H), 7.83 (d, J=9.0 Hz, 1H), 10.13 (s, 1H). Mass spectrum: (M+H)$^+$=595.

EXAMPLE 58

(2S,3S,5S)-5-(3-Hydroxy-benzoyl)amino-2-((3S, 3aR,6aS)-bis-tetrahydrofuran-3-yl-oxycarbonyl) amino-1,6-diphenyl-3-hydroxyhexane (2S,3S,5S)-2-Amino-3-hydroxy-5-(t-butyloxycarbonylamino)-1,6-diphenylhexane was coupled with 3-hydroxybenzoic acid using standard coupling procedures followed by TFA treatment and coupling with ((3S, 3aR,6aS)-bis-tetrahydrofuran-3-yl-oxycarbonyl)oxy-4-nitro benzene using the procedure described in Example 46B to give the desired compound. $^1$H NMR (CD$_3$OD) δ 1.28 (m, 1H), 1.73 (m, 1H), 1.79 (m, 1H), 1.99 (m, 1H), 2.75 (m, 1H), 2.82 (m, 2H), 2.85 (m, 2H), 2.99 (m, 1H), 3.33 (m, 1H), 3.53 (dd, J=9.0, 6.0 Hz, 1H), 3.70 (dt, J=3.0, 6.0 Hz, 1H), 3.84 (m, 1H), 3.87 (m, 2H), 3.96 (m, 1H), 4.45 (m, 1H), 4.93 (m, 1H), 5.60 (d, J=5.7 Hz, 1H), 6.88 (m, 1H), 7.03 (m, 1H), 7.12 (m, 2H), 7.15 (d, J=9.0 Hz, 2H), 7.18–7.23 (m, 10H). Mass spectrum: (M+H)$^+$=561.

EXAMPLE 59

(2S,3S,5S)-2-(3-Hydroxy-2-methyl-benzoyl)amino-5-((3R,3aS,6aR)-bis-tetrahydrofuran-3-yl-oxycarbonyl)amino-1,6-diphenyl-3-hydroxyhexane (2S,3S,5S)-2-Amino-3-hydroxy-5-(t-butyloxycarbonylamino)-1,6-diphenylhexane was coupled with 3-hydroxy-2-methyl-benzoic acid using standard coupling procedures followed by TFA treatment and coupling with ((3R,3aS,6aR)-bis-tetrahydrofaran-3-yl-oxycarbonyl) oxy-4-nitro benzene using the procedure described in Example 46B to give the desired compound. $^1$H NMR (DMSO-d$_6$) δ 1.38 (m, 1H), 1.47 (m, 1H), 1.61 (m, 2H), 1.88 (s, 3H), 2.55 (m, 1H), 2.75 (m, 1H), 2.82 (m, 3H), 3.55 (dd, J=9.0, 6.0 Hz, 1H), 3.61 (m, 1H), 3.68 (m, 1H), 3.74 (dt, J=3.0, 6.0 Hz, 1H), 3.85 (dd, J=9.0, 6.0 Hz, 1H), 3.99 (m, 1H), 4.36 (m, 1H), 4.73 (d, J=6.3 Hz, 1H), 4.88 (m, 1H), 5.52 (d, J=5.7 Hz, 1H), 6.50 (d, J=7.8 Hz, 1H), 6.79 (d, J=7.8 Hz, 1H), 6.96 (t, J=7.8 Hz, 1H), 7.13–7.28 (m, 10H), 7.69 (d, J=9.0 Hz, 1H), 9.40 (s, 1H). Mass spectrum: (M+H)$^+$=575.

EXAMPLE 60

(2S,3S,5S)-2-(3-Hydroxy-2-methyl-benzoyl)amino-5-((3S,3aR,6aS)-bis-tetrahydrofuran-3-yl-oxycarbonyl)amino-1,6-diphenyl-3-hydroxyhexane (2S,3S,5S)-2-Amino-3-hydroxy-5-(t-butyloxycarbonylamino)-1,6-diphenylhexane was coupled with 3-hydroxy-2-methyl-benzoic acid using standard coupling procedures followed by TEA treatment and coupling with ((3S,3aR,6aS)-bis-tetrahydrofuran-3-yl-oxycarbonyl)oxy-4-nitro benzene using the procedure described in Example 46B to give the desired compound. $^1$H NMR (DMSO-d$_6$) δ 1.24 (m, 1H), 1.62 (m, 2H), 1.69 (m, 1H), 1.86 (s, 3H), 2.64 (m, 1H), 2.72 (m, 1H), 2.82 (m, 2H), 2.94 (m, 1H), 3.44 (m, 2H), 3.71 (m, 1H), 3.82 (m, 1H), 4.32 (m, 1H), 4.71 (d, J=6.0 Hz, 1H), 4.88 (m, 1H), 5.57 (d, J=5.7 Hz, 1H), 6.47 (d, J=7.8 Hz, 1H), 6.79 (d, J=7.8 Hz, 1H), 6.95 (t, J=7.8 Hz, 1H), 7.15–7.28 (m, 10H), 7.68 (d, J=9.0 Hz, 1H), 9.39 (s, 1H). Mass spectrum: (M+H)$^+$=575.

EXAMPLE 61

(2S,3S,5S)-2-(3-Amino-2-methyl-benzoyl)amino-5-((3R,3aS,6aR)-bis-tetrahydrofuran-3-yl-oxycarbonyl)amino-1,6-diphenyl-3-hydroxyhexane (2S,3S,5S)-2-Amino-3-hydroxy-5-(t-butyloxycarbonylamino)-1,6-diphenylhexane was coupled with 3-amino-2-methyl-benzoic acid using standard coupling procedures followed by TFA treatment and coupling with ((3R,3aS,6aR)-bis-tetrahydrofuran-3-yl-oxycarbonyl)oxy-4-nitro benzene using the procedure described in Example 46B to give the desired compound. $^1$H NMR (DMSO-d$_6$) δ 1.38 (m, 1H), 1.46 (m, 1H), 1.62 (m, 2H), 1.79 (s, 3H), 2.55 (m, 1H), 2.75 (m, 1H), 2.81 (m, 3H), 3.55 (dd, J=9.0, 6.0 Hz, 1H), 3.60 (m, 1H), 3.67 (m, 1H), 3.73 (m, 1H), 3.79 (m, 1H), 3.86 (dd, J=9.0, 6.0 Hz, 1H), 4.35 (m, 1H), 4.71 (d, J=6.3 Hz, 1H), 4.87 (m, 1H), 4.89 (m, 2H), 5.53 (d, J=5.7 Hz, 1H), 6.28 (d, J=7.8 Hz, 1H), 6.62 (d, J=7.8 Hz, 1H), 6.85 (t, J=7.8 Hz, 1H), 7.13–7.28 (m, 10H), 7.61 (d, J=9.0 Hz, 1H). Mass spectrum: (M+H)$^+$=574.

EXAMPLE 62

(2S,3S,5S)-2-(3-Amino-6-chloro-benzoyl)amino-5-((3R,3aS,6aR)-bis-tetrahydrofuran-3-yl-oxycarbonyl)amino-1,6-diphenyl-3-hydroxyhexane (2S,3S,5S)-2-Amino-3-hydroxy-5-(t-butyloxycarbonylamino)-1,6-diphenylhexane was coupled with 3-amino-6-chloro-benzoic acid using standard coupling procedures followed by TFA treatment and coupling with ((3R,3aS,6aR)-bis-tetrahydrofuran-3-yl-oxycarbonyl)oxy-4-nitro benzene using the procedure described in Example 46B to give the desired compound. $^1$H NMR (DMSO-d$_6$) δ 1.32 (m, 1H), 1.45 (m, 1H), 1.60 (m, 1H), 1.67 (m, 2H), 2.74 (dd, J=9.0, 6.0 Hz, 1H), 2.81 (m, 4H), 3.53 (dd, J=9.0, 6.0 Hz, 1H), 3.59 (m, 1H), 3.62 (m, 1H), 3.73 (dt, J=7.5, 3.0 Hz, 1H), 3.96 (m, 1H), 4.34 (m, 1H), 4.68 (m, 1H), 4.84 (m, 1H), 5.38 (br s, 2H), 5.52 (d, J=5.7 Hz, 1H), 6.43 (d, I=2.7 Hz, 1H), 6.57 (dd, J=2.7, 8.7 Hz, 1H), 7.03 (d, J=8.7 Hz, 1H), 7.13–7.28 (m, 10H), 7.87 (d, J=9.0 Hz, 1H). Mass spectrum: (M+H)$^+$=594.

EXAMPLE 63

(2S,3S,5S)-2-(3-Amino-6-chloro-benzoyl)amino-5-((3S,3aR,6aS)-bis-tetrahydrofuran-3-yl-oxycarbonyl)amino-1,6-diphenyl-3-hydroxyhexane (2S,3S,5S)-2-Amino-3-hydroxy-5-(t-butyloxycarbonylamino)-1,6-diphenylhexane was coupled with 3-amino-6-chloro-benzoic acid using standard coupling procedures followed by TFA treatment and coupling with ((3S,3aR,6aS)-bis-tetrahydrofuran-3-yl-oxycarbonyl)oxy-4-nitro benzene using the procedure described in Example 46B to give the desired compound. $^1$H NMR (DMSO-d$_6$) δ 1.65 (m, 2H), 1.72 (m, 2H), 1.83 (m, 1H), 2.59 (m, 1H), 2.72 (m, 1H), 2.82 (m, 2H), 2.93 (m, 1H), 3.41 (m, 1H), 3.67 (m, 1H), 3.71 (m, 1H), 3.81 (m, 2H), 3.93 (m, 1H), 4.29 (m, 1H), 4.69 (d, J=6.6 Hz, 1H), 4.83 (m, 1H), 5.37 (br s, 2H), 5.57 (d, J=5.7 Hz, 1H), 6.42 (d, J=2.7 Hz, 1H), 6.57 (dd, J=2.7, 8.7 Hz, 1H), 7.02 (d, J=8.7 Hz, 1H), 7.13–7.28 (m, 10H), 7.87 (d, J=9.0 Hz, 1H). Mass spectrum: (M+H)$^+$=594.

EXAMPLE 64

(2S,3S,5S)-2-(4-Hydroxy-benzoyl)amino-5-((3R,3aS,6aR)-bis-tetrahydrofuran-3-yl-oxycarbonyl)amino-1,6-diphenyl-3-hydroxyhexane (2S,3S,5S)-2-Amino-3-hydroxy-5-(t-butyloxycarbonylamino)-1,6-diphenylhexane was coupled with 4-hydroxybenzoic acid using standard coupling procedures followed by TFA treatment and coupling with ((3R,3aS,6aR)-bis-tetrahydrofuran-3-yl-oxycarbonyl)oxy-4-nitro enzene using the procedure described in Example 46B to give the desired compound. $^1$H NMR (DMSO-d$_6$) δ 1.37 (m, 1H), 1.41 (m, 1H), 1.47 (m, 1H), 1.52 (m, 2H), 2.68 (m, 1H), 2.71 (m, 1H), 2.82 (m, 1H), 2.88 (m, 3H), 3.51 (dd, J=9.0, 6.0 Hz, 1H), 3.59 (m, 1H), 3.67 (m, 1H), 3.73 (dt, J=3.0, 7.8 Hz, 1H), 3.81 (dd, J=9.0, 6.0 Hz, 1H), 3.96 (m, 1H), 4.32 (m, 1H), 4.84 (m, 2H), 5.51 (d, J=5.7 Hz, 1H), 6.77 (d, J=8.4 Hz, 2H), 7.13–7.28 (m, 10H), 7.67 (d, J=8.4 Hz, 2H), 9.92 (s, 1H). Mass spectrum: (M+H)$^+$=561.

EXAMPLE 65

(2S,3S,5S)-2-(4-Hydroxy-benzoyl)amino-5-((3S,3aR,6aS)-bis-tetrahydrofuran-3-yl-oxycarbonyl)amino-1,6-diphenyl-3-hydroxyhexane (2S,3S,5S)-2-Amino-3-hydroxy-5-(t-butyloxycarbonylamino)-1,6-diphenylhexane was coupled with 4-hydroxybenzoic acid using standard coupling procedures followed by TFA treatment and coupling with ((3S,3aR,6aS)-bis-tetrahydrofuran-3-yl-oxycarbonyl)oxy-4-nitro benzene using the procedure described in Example 46B to give the desired compound. $^1$H NMR (DMSO-d$_6$) δ 1.24 (m, 1H), 1.52 (m, 2H), 1.65 (m, 1H), 1.79 (m, 1H), 2.60 (m, 1H), 2.65 (m, 1H), 2.71 (m, 1H), 2.87 (m, 3H), 3.43 (m, 1H), 3.67 (m, 2H), 3.77 (m, 1H), (m, 1H), 3.96 (m, 1H), 4.30 (m, 1H), 4.85 (m, 2H), 5.55 (d, J=5.7 Hz, 1H), 6.77 (d, J=8.4 Hz, 2H), 7.11–7.27 (m, 10H), 7.64 (d, J=8.4 Hz, 2H), 9.91 (s, I1H). Mass spectrum: (M+H)$^+$=561.

EXAMPLE 66

(2S,3S,5S)-2-(3-Hydroxy-benzoyl)amino-5-((3R,3aS,6aR)-bis-tetrahydrofuran-3-yl-oxycarbonyl)amino-1,6-diphenyl-3-hydroxyhexane (2S,3S,5S)-2-Amino-3-hydroxy-5-(t-butyloxycarbonylamino)-1,6-diphenylhexane was coupled with 3-hydroxybenzoic acid using standard coupling procedures followed by TFA treatment and coupling with ((3R,3aS,6aR)-bis-tetrahydrofuran-3-yl-oxycarbonyl)oxy-4-nitro benzene using the procedure described in Example 46B to give the desired compound. $^1$H NMR (DMSO-d$_6$) δ 1.37 (m, 1H), 1.45 (m, 1H), 1.53 (m, 3H), 2.55 (m, 1H), 2.67 (m, 1H), 2.70 (m, 1H), 2.82 (m, 1H), 2.87 (m, 2H), 3.50 (dd, J=9.0, 6.0 Hz, 1H), 3.59 (m, 1H), 3.68 (m, 1H), 3.72 (m, 1H), 3.82 (dd, J=9.0, 6.0 Hz, 1H), 3.97 (m, 1H), 4.35 (m, 1H), 4.82 (d, J=6.0 Hz, 1H), 4.87 (m, 1H), 5.52 (d, J=5.7 Hz, 1H), 6.87 (d, J=6.6 Hz, 1H), 7.13–7.28 (m, 12H), 7.68 (d, J=6.6 Hz, 1H), 9.61 (s, 1H). Mass spectrum: (M+H)$^+$=561.

EXAMPLE 67

(2S,3S,5S)-2-(3-Hydroxy-benzoyl)amino-5-((3S, 3aR,6aS)-bis-tetrahydrofuran-3-yl-oxycarbonyl) amino-1 6-diphenyl-3-hydroxyhexane (2S,3S,5S)-2-Amino-3-hydroxy-5-(t-butyloxycarbonylamino)-1,6-diphenylhexane was coupled with 3-hydroxybenzoic acid using standard coupling procedures followed by TFA treatment and coupling with ((3S, 3aR,6aS)-bis-tetrahydrofuran-3-yl-oxycarbonyl)oxy-4-nitro benzene using the procedure described in Example 46B to give the desired compound. $^1$H NMR (DMSO-d$_6$) δ 1.38 (m, 1H), 1.53 (m, 3H), 1.64 (m, 1H), 1.79 (m, 1H), 2.62 (m, 2H), 2.70 (m, 1H), 2.88 (m, 2H), 2.91 (m, 1H), 3.40 (m, 2H), 3.68 (m, 1H), 3.77 (m, 1H), 3.82 (m, 1H), 3.92 (m, 1H), 4.31 (m, 1H), 4.81 (d, J=6.0 Hz, 1H), 4.86 (m, 1H), 5.54 (d, J=5.7 Hz, 1H), 6.88 (d, J=6.6 Hz, 1H), 7.11–7.28 (m, 12H), 7.68 (d, J=6.6 Hz, 1H), 9.60 (s, 1H). Mass spectrum: (M+H)$^+$=561.

EXAMPLE 68

(2S,3S,5S)-2-(Benzoyl)amino-5-((3R,3aS,6aR)-bis-tetrahydrofuran-3-yl-oxycarbonyl)amino-1,6-diphenyl-3-hydroxyhexane (2S,3S,5S)-2-Amino-3-hydroxy-5-(t-butyloxycarbonylamino)-1,6-diphenylhexane was coupled with benzoic acid using standard coupling procedures followed by TFA treatment and coupling with ((3R,3aS,6aR)-bis-tetrahydrofuran-3-yl-oxycarbonyl)oxy-4-nitro benzene using the procedure described in Example 46B to give the desired compound. $^1$H NMR (DMSO-d$_6$) δ 1.40 (m, 1H), 1.47 (m, 1H), 1.54 (m, 2H), 2.54 (m, 1H), 2.70 (m ,1H), 2.82 (m, 1H), 2.89 (m, 2H), 3.51 (dd, J=9.0, 6.0 Hz, 1H), 3.60 (m, 1H), 3.71 (m, 2H), 3.81 (dd, J=9.3, 6.0 Hz, 1H), 3.98 (m, 1H), 4.37 (m, 1H), 4.86 (m, 2H), 5.52 (d, J=5.7 Hz, 1H), 7.11–7.28 (m, 11H), 7.47 (m, 3H), 7.78 (d, J=7.5 Hz, 2H), 7.93 (d, J=9.0 Hz, 1H), Mass spectrum: (M+H)$^+$=545.

EXAMPLE 69

(2S,3S,5S)-2-(Benzoyl)amino-5-((3S,3aR,6aR)-bis-tetrahyddrofuran-3-yl-oxycarbonyl)amino-1,6-diphenyl-3-hydroxyhexane (2S,3S,5S)-2-Amino-3-hydroxy-5-(t-butyloxycarbonylamino)-1,6-diphenylhexane was coupled with benzoic acid using standard coupling procedures followed by TFA treatment and coupling with ((3S,3aR,6aS)-bis-tetrahydrofuran-3-yl-oxycarbonyl)oxy-4-nitro benzene using the procedure described in Example 46B to give the desired compound. $^1$H NMR (DMSO-d$_6$) δ 1.55 (m, 2H), 1.65 (m, 1H), 1.70 (m, 1H), 2.65 (m, 2H), 2.90 (m, 3H), 3.45 (dd, J=9.0, 6.0 Hz, 1H), 3.69 (m, 2H), 3.83 (dd, J=9.3, 6.0 Hz, 1H), 3.93 (m, 1H), 4.36 (m, 1H), 4.85 (m, 2H), 5.56 (d, J=5.7 Hz, 1H), 7.11–7.28 (m, 11H), 7.47 (m, 3H), 7.75 (d, J=7.5 Hz, 2H), 7.91 (d, J=9.0 Hz, 1H). Mass spectrum: (M+H)$^+$=545.

EXAMPLE 70

(2S,3S,5S)-2-(4-Acetoxy-benzoyl)amino-5-((3R, 3aS,6aR)-bis-tetrahydrofuran-3-yl-oxycarbonyl) amino-1,6-diphenyl-3-hydroxyhexane (2S,3S,5S)-2-Amino-3-hydroxy-5-(t-butyloxycarbonylamino)-1,6-diphenylhexane was coupled with 4-acetoxybenzoic acid using standard coupling procedures followed by TFA treatment and coupling with ((3R, 3aS,6aR)-bis-tetrahydrofuran-3-yl-oxycarbonyl)oxy-4-nitro benzene using the procedure described in Example 46B to give the desired compound. $^1$H NMR (DMSO-d$_6$) δ 1.39 (m, 1H), 1.47 (m, 1H), 1.52 (m, 2H), 2.29 (s, 3H), 2.55 (m, 1H), 2.68 (m, 1H), 2.72 (m, 1H), 2.82 (m, 1H), 2.89 (m, 2H1), 3.51 (dd, J=9.0, 6.0 Hz, 1H), 3.71 (m, 1H), 3.81 (m, 1H), 3.87 (m, 1H), 3.97 (dd, J=9.6, 6.6 Hz, 1H), 3.98 (m, 1H), 4.37 (m, 1H), 4.85 (m, 2H), 5.52 (d, J=5.7 Hz, 1H), 5.62 (d, J=5.4 Hz, 1H), 3.98 (m, 1H), (m, 10H), 7.83 (d, J=8.7 Hz, 2H), 7.97 (d, J=9.0 Hz, 1H). Mass spectrum: (M+H)$^+$=603.

EXAMPLE 71

(2S,3S,5S)-2-(4-Amino-2-chloro-benzoyl)amino-5-((3R,3aS,6aR)-bis-tetrahydrofuran-3-yl-oxycarbonyl)amino-1,6-diphenyl-3-hydroxyhexane (2S,3S,5S)-2-Amino-3-hydroxy-5-(t-butyloxycarbonylamino)-1,6-diphenylhexane was coupled with 4-amino-2-chloro-benzoic acid using standard coupling procedures followed by TFA treatment and coupling with ((3R,3aS,6aR)-bis-tetrahydrofuran-3-yl-oxycarbonyl)oxy-4-nitro benzene using the procedure described in Example 46B to give the desired compound. $^1$H NMR (DMSO-d$_6$) δ 1.38 (m, 1H), 1.47 (m, 1H), 1.60 (m, 2H), 2.60 (m, 1H), 2.70 (m, 1H), 2.82 (m, 3H), 3.53 (m, 1H), 3.61 (m, 2H), 3.72 (m, 1H), 3.83 (m, 1H), 3.95 (m, 1H), 4.30 (m, 1H), 4.77 (m, 1H), 4.85 (m, 1H), 5.52 (d, J=5.7 Hz, 1H), 5.67 (m, 2H), 6.46 (d, J=6.6 Hz, 1H), 6.56 (d, J=2.7 Hz, 1H), 6.88 (d, J=9.0 Hz, 1H), 7.11–7.28 (m, 11H), 7.58 (d, J=6.6 Hz, 1H). Mass spectrum: (M+H)$^+$=594.

EXAMPLE 72

(2S,3S,5S)-2-(4-Amino-2-chloro-benzoyl)amino-5-((3S,3aR,6aS)-bis-tetrahydrofuran-3-yl-oxycarbonyl) amino-1,6-diphenyl-3-hydroxyhexane (2S,3S,5S)-2-Amino-3-hydroxy-5-(t-butyloxycarbonylamino)-1,6-diphenylhexane was coupled with 4-amino-2-chloro-benzoic acid using standard coupling procedures followed by TFA treatment and coupling with ((3S,3aR,6aS)-bis-tetrahydrofuran-3-yl-oxycarbonyl)oxy-4-nitro benzene using the procedure described in Example 46B to give the desired compound. $^1$H NMR (DMSO-d$_6$) δ 1.59 (m, 2H), 1.69 (m, 1H), 1.80 (m, 1H), 2.57 (m, 1H), 2.70 (m, 1H), 2.80 (m, 2H), 2.91 (m, 1H), 3.41 (m, 1H), 3.65 (m, 2H), 3.70 (m, 1H), 3.80 (m 2H), 3.90 (m, 1H), 4.26 (m, 1H), 4.76 (d, J=6.0 Hz, 1H), 4.85 (m, 1H), 5.58 (d, J=5.7 Hz, 1H), 5.67 (s, 2H), 6.46 (dd, J=2.7, 6.6 Hz, 1H), 6.56 (d, J=2.7 Hz, 1H), 6.93 (d, J=9.0 Hz, 1H), 7.11–7.28 (m, 11H), 7.56 (d, J=6.6 Hz, 1H). Mass spectrum: (M+H)$^+$=594.

EXAMPLE 73

(2S,3S,5S)-2-(3-Methoxy-4-hydroxy-benzoyl) amino-5-((3R,3aS,6aR)-bis-tetrahydrofuran-3-yl-oxycarbonyl)amino-1,6-diphenyl-3-hydroxyhexane (2S,3S,5S)-2-Amino-3-hydroxy-5-(t-butyloxycarbonylamino)-1,6-diphenylhexane was coupled with 3-methoxyl-4-hydroxy-benzoic acid using standard coupling procedures followed by TFA treatment and coupling with ((3R,3aS,6aR)-bis-tetrahydrofuran-3-yl-oxycarbonyl)oxy-4-nitro benzene using the procedure described in Example 46B to give the desired compound. $^1$H NMR (DMSO-d$_6$) δ 1.48 (m, 1H), 1.49 (m, 1H), 1.54 (m, 1H), 2.53 (m, 1H), 2.72 (dd, J=9.0, 2.7 Hz, 1H), 2.83 (m, 1H), 2.89 (m, 2H), 3.51 (dd, J=6.0, 3.0 Hz, 1H), 3.60 (m, 1H), 3.68 (m, 1H), 3.73 (dt, J=4.5, 2.4 Hz, 1H), 3.81 (s, 3H), 3.82 (m, 1H), 3.9 (m, 1H), 4.32 (m, 1H), 4.83 (d, J=4.5 Hz, 1H), 4.85 (m, 1H), 5.52 (d, J=5.7 Hz, 1H), 6.78 (d, J=5.7 Hz, 1H), 7.09–7.30 (m, 12H), 7.35 (d, J=2.4 Hz, 1H), 7.66 (d, J=5.7 Hz, 1H), 9.43 (s, 1H). Mass spectrum: (M+H)⁺=591.

EXAMPLE 74

(2S,3S,5S)-5-(2,6-Dimethyl-3-hydroxy-phenoxyacetyl)amino-2-((3R,3aS,6aR)-bis-tetrahydrofuran-3-yl-oxycarbonyl)amino-1,6-diphenyl-3-hydroxyhexane To a solution of (2S,3S,5S)-2-((3R,3aS,6aR)-bis-tetrahydrofuran-3-yl-oxycarbonyl)amino-3-hydroxy-5-amino-1,6-diphenylhexane in THF and methylene chloride was subsequently added 2,6-dimethyl-3-hydroxy-phenoxy acetic acid, EDIC, HOBT, and triethyl amine. The resulting solution was allowed to stir at ambient temperature for 6 hr, and concentrated in vacuo. The residue was taken up in ethyl acetate, washed with one portion of 3N HCl, one portion of 10% aqueous NaHCO₃, and one portion of saturated brine, dried over MgSO₄, and concentrated in vacuo. The resulting product mixture was purified by silica gel chromatography using 70% ethyl acetate:hexanes as an eluent to provide the desired compound. ¹H NMR (CDCl₃) δ 1.67 (m, 2H), 1.80 (t, J=6.0 Hz, 2H), 2.00 (s, 3H), 2.03 (s, 3H), 2.82–3.00 (m, 5H), 3.76 (m, 2H), 3.88 (m, 2H), 4.00 (dd, J=9.0, 6.0 Hz, 2H), 4.14 (AB, J=15.0 Hz, 2H), 4.31 (m, 1H), 4.97 (bs, 1H), 5.10 (m, 2H), 5.69 (d, J=5.4 Hz, 1H), 6.53 (d, J=8.1 Hz, 1H), 6.85 (d, J=9.0 Hz, 1H), 6.97 (d, J=7.5 Hz, 1H), 7.15–7.31 (m, 12H). Mass spectrum: (M+H)⁺=619.

EXAMPLE 75

(2S,3S,5S)-2-(N-(N-((2-isopropyl-4-thiazolyl)methoxycarbonyl)-L-valinyl)amino)-5-(3R-2,2-dimethyl-1,1-dioxy-tetrahydrothienyloxycarbonyl)amino-1,6-diphenyl-3-hydrohexane The Doe protecting group of the compound from Example 33A was removed using tifluoroacetic acid in methylene chloride and the resulting (2S,3S,5S)-2-amino-5-(2,2,-dimethyl-1,1-dioxo-3R-tetrahydrothienyloxycarbonyl)amino-1,6-diphenyl-3-hydroxyhexane coupled with N-(N-((2-isopropyl-4-thiazolyl)methoxycarbonyl)-L-vaayl)amino-L-valine using standard coupling procedures to give the desired compound.

The biological activity of the compounds of the invention is illustrated by the following data.

Fluorogenic Assay for Screening Inhibitors of HIV Protease

The inhibitory potency of the compounds of the invention were determined by the following method: The compound of the invention was dissolved in DMSO and a small aliquot further diluted with DMSO to 100 times the final concentration desired for testing. The reaction was carried out in a 6×50 mm tube in a total volume of 300 microliters. The final concentrations of the components in the reaction buffer were: 125 mM sodium acetate, 1M sodium chloride, 5 mM dithiotlreitol, 0.5 mg/mL bovine serum albumin, 1.3 mM fluorogenic substrate consisting of Dabcyl-Gaba-Ser-Gln-Asn-Tyr-Pro-Ile-Val-Gln-EDANS wherein DABCYL=4-(4-dimethylamino-phenyl)azobenzoic acid, Gaba=γ-aminobutyric acid, and EDANS=5-((2-aminoethyl)amino)-naphthalene-1-sulfonic acid, and 2% (v/v) dimethylsulfoxide, pH 4.5. After addition of inhibitor, the reaction mixture was placed in the fluorometer cell holder and incubated at 30° C. for several minutes. The reaction was initiated by the addition of a small aliquot of cold HIV protease. The fluorescence intensity (excitation 340 nM, emission 490 nM) was recorded as a function of time. The reaction rate was determined for the first six to eight minutes. The observed rate was directly proportional to the moles of substrate cleaved per unit time. The percent inhibition was calculated according to the equation: 100×(1−(rate of inhibitor)/(rate in absence of inhibitor)). As a control, duplicate reactions were performed identically as above but without the addition of an inhibitor compound.

Table 1 shows the inhibitory potencies (designated as % inhibition) of the specified Examples against HIV-1 protease when tested in the fluorogenic assay at the indicated concentrations. the data points are representative of two duplicate determinations.

TABLE 1

| Example | % Inhibition | Inhibitor Concentration (nM) |
|---|---|---|
| 1 | 78 | 0.5 |
| 2 | 60 | 0.5 |
| 3 | 91 | 0.5 |
| 4 | 74 | 0.5 |
| 5 | 87 | 0.5 |
| 6 | 91 | 0.5 |
| 7 | 88 | 0.5 |
| 8 | 56 | 0.5 |
| 9 | 69 | 0.5 |
| 10 | 49 | 0.5 |
| 11 | 82 | 0.5 |
| 12 | 74 | 0.5 |
| 13 | 50 | 2.4 |
| 14 | 69 | 0.5 |
| 15 | 43 | 0.5 |
| 16 | 87 | 0.5 |
| 17 | 50 | 1 |
| 20 | 64 | 0.5 |
| 22 | 73 | 0.5 |
| 23 | 39 | 0.5 |
| 24 | 80 | 0.5 |
| 25 | 85 | 0.5 |
| 26 | 80 | 0.5 |
| 27 | 50 | 1.3 |
| 30 | 52 | 0.5 |
| 31 | 52 | 0.5 |
| 32 | 50 | 0.5 |
| 33 | 84 | 0.5 |
| 34 | 52 | 0.5 |
| 35 | 52 | 0.5 |
| 36 | 66 | 0.5 |
| 37 | 83 | 0.5 |
| 38 | 53 | 0.5 |
| 39 | 66 | 0.5 |
| 40 | 43 | 0.5 |
| 41 | 53 | 0.5 |
| 42 | 80 | 0.5 |
| 43 | 42 | 0.5 |
| 44 | 72 | 0.5 |
| 45 | 56 | 0.5 |
| 46 | 74 | 0.5 |
| 47 | 82 | 0.5 |
| 48 | 80 | 0.5 |
| 49 | 74 | 0.5 |
| 50 | 68 | 0.5 |
| 51 | 83 | 0.5 |
| 52 | 69 | 0.5 |
| 53 | 56 | 1 |
| 54 | 50 | 1.4 |
| 55 | 82 | 0.5 |
| 57 | 78 | 0.5 |
| 58 | 50 | 1.1 |
| 59 | 67 | 0.5 |

TABLE 1-continued

| Example | % Inhibition | Inhibitor Concentration (nM) |
|---|---|---|
| 60 | 50 | 2.2 |
| 62 | 70 | 0.5 |
| 63 | 50 | 2.9 |
| 64 | 64 | 0.5 |
| 66 | 68 | 0.5 |
| 68 | 65 | 0.5 |
| 71 | 72 | 0.5 |
| 74 | 89 | 0.5 |

Antiviral Activity

The anti-HIV activity of the compound of the invention was determined in MF4 cells according to the following procedure: MT4 cells were infected with cell-free supernatant of HIVIIIB (previously frozen with known 50% tissue culture infectious dose ($TCID_{50}$) at 0.003 multiplicity of infection (MOI)) for one hour. After one hour infection, cells were washed twice to remove residual viruses, resuspended in culture media and seeded into 96-well tissue culture plates at $1\times10^4$ cells per well with various half-log dilutions of compounds. Uninfected cells were included a toxicity and cell controls. RPMI 1640 media (GIBCO) with 10% fetal bovine serum was used as culture media. Various concentrations (50%, 25% and 12.5%) of human serum (SIGMA) were added to culture media resulting in final concentrations of 60%, 35% and 22.5% total serum. All assay plates were incubated in a 37° C. incubator for 5 days. The compound 3-[4,5-dimethylthiozol-2-yl]-2,5-diphenyltetrazolium bromide (MTT, SIGMA, 5 mg .mL stock in PBS) was then added to all wells at 25 μL per well and incubated for 4 hours. SDS (20%) with 0.02N HCl in water was added at 50 μL per well to lyse cells. Plates were incubated overnight for complete cell lysis and then read on a microtiter plate reader at 570/650 nm wavelengths to determine cell optical density (O.D.). Raw data was analysed for percent inhibition by the following formula:

$$\frac{O.D.\ \text{test well} - O.D.\ \text{virus control}}{O.D.\ \text{cell control} - O.D.\ \text{virus control}} \times 100$$

The 50% effective concentration ($EC_{50}$) was calculated by the median effect equation (Chou, 1975, Proc. Int. Cong. Pharmacol. 6th p. 619) to determine the efficacy of compound. The 50% cytotoxicity concentration ($CTC_{50}$) was calculated using uninfected MT4 cells Under these conditions, the data of Table 2 was obtained (n=four duplicate determinations).

TABLE 2

| Example | $EC_{50}$ (μM) | $CTC_{50}$ (μM) |
|---|---|---|
| 1 | 0.009 | 95 |
| 2 | 0.17 | 90 |
| 3 | 0.008 | 61 |
| 4 | 0.032 | 41 |
| 5 | 0.041 | >100 |
| 6 | 0.061 | >100 |
| 7 | 0.037 | 82 |
| 8 | 0.815 | >100 |
| 9 | 0.253 | 56 |
| 10 | 0.184 | >100 |
| 11 | 0.205 | 48 |
| 12 | 0.353 | >32 |
| 13 | 2.914 | 18 |
| 14 | 0.268 | 64 |
| 15 | 0.16 | 46 |
| 16 | <0.032 | >100 |
| 17 | 5.793 | 56 |
| 20 | 0.034 | >100 |
| 22 | 0.107 | >100 |
| 23 | 0.891 | >100 |
| 24 | 0.114 | >100 |
| 25 | 0.972 | >100 |
| 26 | 0.157 | 29.8 |
| 30 | 1.003 | 13.5 |
| 31 | 1.101 | 53.3 |
| 32 | 1.184 | >100 |
| 33 | 0.442 | 18.26 |
| 34 | 0.009 | 56.3 |
| 35 | 0.428 | >100 |
| 36 | 0.03 | 27.75 |
| 37 | 0.014 | >100 |
| 38 | 0.14 | >100 |
| 39 | 0.055 | 56.23 |
| 40 | 0.502 | >100 |
| 41 | 0.043 | >100 |
| 42 | 0.07 | >100 |
| 43 | 0.27 | >100 |
| 44 | 0.37 | >100 |
| 45 | 0.45 | >100 |
| 46 | 0.034 | 56.23 |
| 47 | 0.055 | >100 |
| 48 | 0.011 | 46.56 |
| 49 | 0.042 | >100 |
| 50 | 0.032 | 56.23 |
| 51 | 0.012 | >100 |
| 52 | 0.072 | >100 |
| 53 | 0.704 | >100 |
| 54 | 0.145 | >100 |
| 55 | 0.011 | 49.46 |
| 57 | 0.12 | 80.92 |
| 58 | 2.609 | >100 |
| 59 | 0.153 | >100 |
| 60 | 1.123 | >100 |
| 62 | 0.081 | >100 |
| 63 | 1.565 | >100 |
| 64 | 0.2 | >100 |
| 66 | 0.644 | — |
| 68 | 0.233 | >32 |
| 71 | 0.101 | >100 |
| 74 | 0.007 | 50.5 |

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

Preferred salts of the compounds of the invention include hydrochloride, methanesulfonate, sulfonate, phosphonate and isethionate.

The compounds of the present invention can also be used in the form of esters. Examples of such esters include compounds wherein a hydroxyl group in the compound of this invention has been acylated with an N-protected or unprotected amino acid residue, a phosphate function, a hemisuccinate residue, an acyl residue of the formula $R^*C(O)$— or $R^*C(S)$— wherein $R^*$ is hydrogen, loweralkyl, haloalkyl, alkoxy, thioalkoxy, alkoxyalkyl, thioalkoxyalkyl or haloalkoxy, or an acyl residue of the formula $R_a$—$C(R_b)(R_d)$—$C(O)$— or $R_a$—$C(R_b)(R_d)$—$C(S)$—$0$ wherein $R_b$ and $R_d$ are independently selected from hydrogen or loweralkyl and $R_a$ is —$N(R_e)(R_f)$, $OR_e$ or —$SR_e$ wherein $R_e$ and $R_f$ are independently selected from hydrogen, loweralkyl and haloalkyl, or an amino-acyl residue of the formula $R_{28}NH(CH_2)_2NHCH_2C(O)$— or $R_{28}NH(CH_2)_2OCH_2C(O)$— wherein $R_{28}$ is hydrogen, loweralkyl, arylalkyl, cycloalkylalkyl, alkanoyl, benzoyl or an -amino acyl group. The amino acid esters of particular interest are glycine and lysine; however, other amino acid residues can also be used, including those wherein the amino acyl group is —$C(O)CH_2NR_{29}R_{30}$ wherein $R_{29}$ and $R_{30}$ are independently selected from hydrogen and loweralkyl or the group —$NR_{29}R_{30}$ forms a nitrogen containing heterocyclic ring. These esters serve as pro-drugs of the compound of the present invention and serve to increase the solubility of these substances in the gastrointestinal tract. These esters also serve to increase solubility for intravenous administration of the compound. Other prodrugs include compounds wherein a hydroxyl group in the compound of this invention is functionalized with a substituent of the formula —$CH(R_g)OC(O)R_{31}$ or —$CH(R_g)OC(S)R_{31}$ wherein $R_{31}$ is loweralkyl, haloalkyl, alkoxy, thioalkoxy or haloalkoxy and $R_g$ is hydrogen, loweralkyl, haloalkyl, alkoxycarbonyl, aminocarbonyl, alkylaminocarbonyl or dialkylaminocarbonyl. Such prodrugs can be prepared according to the procedure of Schreiber (Tetrahedron Lett. 1983, 24, 2363) by ozonolysis of the corresponding methallyl ether in methanol followed by treatment with acetic anhydride.

The prodrugs of this invention are metabolized in mix to provide the compound of this invention. The preparation of the prodrug esters is carried out by reacting the compound of the invention with an activated amino acyl, phosphoryl, hemisuccinyl or acyl derivative as defined above. The resulting product is then deprotected to provide the desired pro-drug ester. Prodrugs of the invention can also be prepared by alkylation of the hydroxyl group with (haloalkyl) esters, transacetalization with bis-(alkanoyl)acetals or condensation of the hydroxyl group with an activated aldehyde followed by acylation of the intermediate hemiacetal.

The compounds of the invention are useful for inhibiting retroviral protease, in particular HIV protease, in vitro or in vivo (especially in mammals and in particular in humans). The compounds of the present invention are also useful for the inhibition of retroviruses in vivo, especially human immunodeficiency virus (HIV). The compounds of the present invention are also useful for the treatment or prophylaxis of diseases caused by retroviruses, especially acquired immune deficiency syndrome or an HIV infection in a human or other mammal.

Total daily dose administered to a human or other mammal host in single or divided doses may be in amounts, for example, from 0.001 to 300 mg/kg body weight daily and more usually 0.1 to 10 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrastemal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically aceptable and metabolizable lipid capabale of forming liposomes can be used. The present compositions in liposome form can contain, in addition to the compound of the present invention, stabilizers, preservatives, excipients, and the like. The preferred lipids are the phospholipids and phosphatidyl cholines (lecithins), both natureal and synthetic.

Methods to form liposomes are known in the art. See, for example, Prescott, Ed., Methods in Cell Biology, Volume XIV, Academic Press, New York, N.Y. (1976), p. 33 et seq.

While the compound of the invention can be administered as the sole active pharmaceutical agent, it can also be used in combination with one or more immunomodulators, antiviral agents, other antiinfective agents or vaccines. Other antiviral agents to be administered in combination with a compound of the present invention include AL-72 1, beta interferon, polymannoacetate, reverse transcriptase inhibitors (for example, dideoxycytidine (ddC; zalcitabine), dideoxyinosine (ddI; didanosine), BCH-189, AzdU, carbovir, ddA, d4C, d4T (stavudine), 3TC (lamivudine) DP-AZT, FLT (fluorothymidine), BCH-189, 5-halo-3'-thiadideoxycytidine, PMEA, bis-POMPMEA, zidovudine (AZT), delavirdine, MSA-300, trovirdine and the like), non-nucleoside reverse transcriptase inhibitors (for example, R82193, L-697,661, BI-RG-587 (nevirapine) and the like), retroviral protease inhibitors (for example, HIV protease inhibitors such as ritonavir, Ro 31-8959 (saquinavir), SC-52151, VX-478, AG1343 (nelfinavir), BMS 186,318, SC-55389a, BILA 1096 BS, DMP-450, KNI-227, KNI-272, indinavir and the like), HEPT compounds, L,697,639, R82150, U-87201E and the like), TAT inhibitors (for example, RO-24-7429 and the like), trisodium phosphonoformate, HPA-23, eflonithine, Peptide T, Reticulose (nucleophosphoprotein), ansamycin LM 427, trimetrexate, UA001, ribavirin, alpha interferon, oxetanocin, oxetanocin-G, cylobut-G, cyclobut-A, ara-M, BW882C87, foscamet, BW256U87, BW348U87, L-693,989, BV ara-U, CMV triclonal antibodies, FIAC, HOE-602, HPMPC, MSL-109, TI-23, trifluridine, vidarabine, famciclovir, penciclovir, acyclovir, ganciclovir, castanospermine, rCD4/CD4-IgG, CD4-PE40, butyl-DNJ, hypericin, oxamyristic acid, dextran sulfate and pentosan polysulfate. Immunomodulators that can be administered in combination with the compound of the present invention include bropirimine, Ampligen, anti-human alpha interferon antibody, colony stimulting factor, CL246,738, Imreg-1, Imreg-2, diethydithiocarbamate, interleukin-2, alpha-interferon, inosine pranobex, methionine enkephalin, muramyl-tripeptide, TP-5, erythropoietin, naltrexone, tumor necrosis factor, beta interferon, gamma interferon, interleukin-3, interleukin-4, autologous CD8+ infusion, alpha interferon immunoglobulin, IGF-1, anti-Leu-3A, autovaccination, biostimulation, extracorporeal photophoresis, cyclosporin, rapamycin, FK-565, FK-506, G-CSF, GM-CSF, hyperthermia, isopinosine, IVG, HIVIG, passive immunotherapy and polio vaccine hyperimmunization. Other antiinfective agents that can be administered in combination with the compound of the present invention include pentamidine isethionate. Any of a variety of HIV or AIDS vaccines (for example, gp120 (recombinant), Env 2-3 (gp120), HIVAC-le (gp120), gp160 (recombinant), VaxSyn HIV-1 (gp160), Immuno-Ag (gp160), HGP-30, HIV-Immunogen, p24 (recombinant), VaxSyn HIV-1 (p24) can be used in combination with the compound of the present invention.

Other agents that can be used in combination with the compound of this invention are ansamycin LM 427, apurinic acid, ABPP, A1-721, carrisyn, AS-101, avarol, azimexon, colchicine, compound Q, CS-85, N-acetyl cysteine, (2-oxothiazolidine-4-carboxylate), D-penicflamine, diphenylhydantoin, EL-10, erythropoieten, fusidic acid, glucan, HPA-23, human growth hormone, hydroxchloroquine, iscador, L-ofloxacin or other quinolone antibiotics, lentinan, lithium carbonate, MM-1, monolaurin, MTP-PE, naltrexone, neurotropin, ozone, PAI, panax ginseng, pentofylline, pentoxifylline, Peptide T, pine cone extract, polymannoacetate, reticulose, retrogen, ribavirin, ribozymes, RS-47, Sdc-28, silicotungstate, THA, thymic humoral factor, thymopentin, thymosin fraction 5, thymosin alpha one, thymostimulin, UA001, uridine, vitamin B12 and wobemugos.

Other agents that can be used in combination with the compound of this invention are antifungals such as amphotericin B, clotrimazole, flucytosine, fluconazole, itraconazole, ketoconazole and nystatin and the like.

Other agents that can be used in combination with the compound of this invention are antibacterials such as amikacin sulfate, azithromycin, ciprofloxacin, tosufloxacin, clarithromycin, clofazimine, ethambutol, isoniazid, pyrazinamide, rifabutin, rifampin, streptomycin and TLC G-65 and the like.

Other agents that can be used in combination with the compound of this invention are anti-neoplastics such as alpha interferon, COMP (cyclophosphamide, vincristine, methotrexate and prednisone), etoposide, mBACOD (methotrexate, bleomycin, doxorubicin, cyclophosphamide, vincristine and dexamethasone), PRO-MACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, pentosan polysulfate, platelet factor 4 and SP-PG and the like.

Other agents that can be used in combination with the compound of this invention are drugs for treating neurological disease such as peptide T, ritalin, lithium, elavil, phenytoin, carbamazipine, mexitetine, heparin and cytosine arabinoside and the like.

Other agents that can be used in combination with the compound of this invention are anti-protozoals such as albendazole, azithromycin, clarithromycin, clindamycin, corticosteroids, dapsone, DIMP, eflomithine, 566C80, fansidar, furazolidone, L,671,329, letrazuril, metronidazole, paromycin, pefloxacin, pentamidine, piritrexim, primaquine, pyrimethamine, somatostatin, spiramycin, sulfadiazine, trimethoprim, TMP/SMX, trimetrexate and WR 6026 and the like.

Among the preferred agents for inhibition or treatment of HIV or AIDS in combination with the compound of this invention are reverse transcriptase inhibitors, especially, AZT (zidovudine), ddI (didanosine), ddC (zalcitabine), d4T (stavudine), 3TC (lamivudine), nevirapine, delavirdine, trovirdine, PMEA, bis-POMPMEA and MSA-300.

Other preferred agents for inhibition or treatment of HIV or AIDS in combination with the compound of this invention are HIV protease inhibitors, especially, ABT-538 (i.e. ritonavir) disclosed in PCT Patent Application No. WO94/14436, published Jul. 7, 1994, which is incorporated herein by reference;

N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide (i.e.

indinavir) and related compounds, disclosed in European Patent Application No. EP541168, published May 12, 1993, and U.S. Pat. No. 5,413,999, issued May 9, 1995 which are incorporated herein by reference;

N-tert-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide (i.e., saquinavir) and related compounds, disclosed in U.S. Pat. No. 5,196,438, issued Mar. 23, 1993, which is incorporated herein by reference;

5(S)-Boc-amino-4(S)-hydroxy-6-phenyl-2(R)-phenylmethylhexanoyl-(L)-Val-(L)-Phe-morpholin-4-ylamide and related compounds, disclosed in European Patent Application No. EP532466, published Mar. 17, 1993, which is incorporated herein by reference;

1-Naphthoxyacetyl-beta-methylthio-Ala-(2S,3S)-3-amino-2-hydroxy-4-butanoyl-1,3-thiazolidine-4-t-butylamide (i.e., 1-Naphthoxyacetyl-Mta-(2S,3S)-AHPBA-Thz-NH-tBu), 5-isoquinolinoxyacetyl-beta-methylthio-Ala-(2S,3S)-3-amino-2-hydroxy-4-butanoyl-1,3-thiazolidine-4-t-butylamide (i.e., iQoa-Mta-Apns-Thz-NHtBu) and related compounds, disclosed in European Patent Application No. EP490667, published Jun. 17, 1992 and Chem. Pharm. Bull. 40 (8) 2251 (1992), which are incorporated herein by reference;

[1S-[1R*(R*),2S*]}-$N^1$[3-[[[(1,1-dimethylethyl)amino]carbonyl](2-methylpropyl)amino]-2-hydroxy-1-(phenylmethyl)propyl]-2-[(2-quinolinylcarbonyl)amino]-butanediamide (i.e., SC-52151) and related compounds, disclosed in PCT Patent Application No. WO92/08701, published May 29, 1992 and PCT Patent Application No. WO93/23368, published Nov. 25, 1993, both of which are incorporated herein by reference;

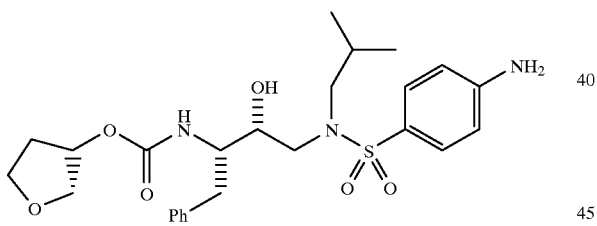

(i.e., VX-478) and related compounds, disclosed in PCT Patent Application No. WO94/05639, published Mar. 17, 1994, which is incorporated herein by reference;

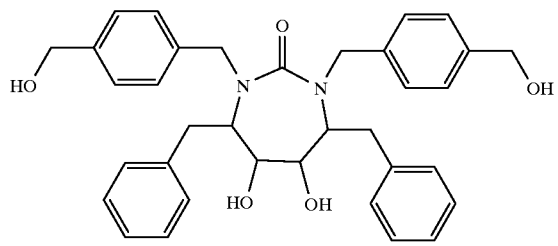

(i.e., DMP-323) or

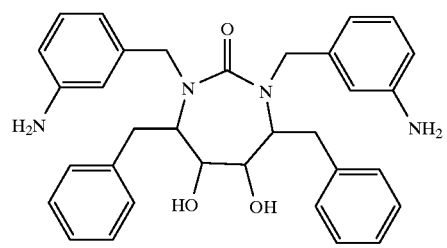

(i.e., DMP-450)

and related compounds, disclosed in PCT Patent Application No. WO93/07128, published Apr. 15, 1993, which is incorporated herein by reference;

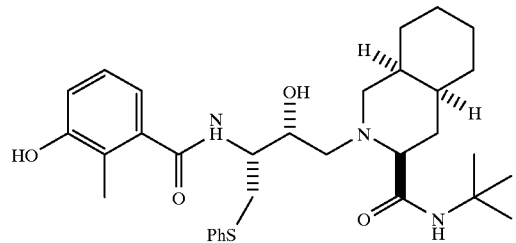

(i.e., AG1343, (nelfinavir)), disclosed in PCT Patent Application No. WO95/09843, published Apr. 13, 1995 and U.S. Pat. No. 5,484,926, issued Jan. 16, 1996, which are incorporated herein by reference;

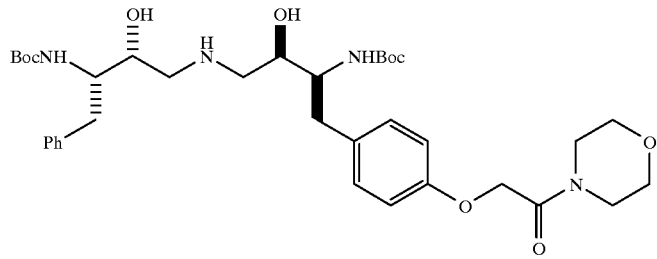

(i.e., BMS 186,318) disclosed in European Patent Application No. EP580402, published Jan. 26, 1994, which is incorporated herein by reference;

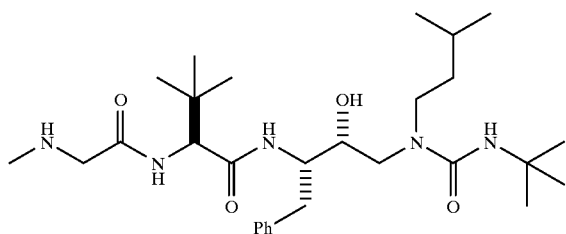

(i.e., SC-55389a) disclosed at 2nd National Conference on Human Retroviruses and Related Infections, (Washington, D,.C., Jan 29–Feb. 2, 1995), Session 88; and

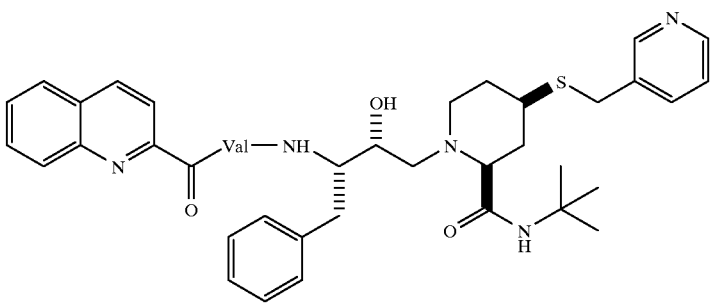

(i.e. BILA 1096 BS) and related compounds disclosed in European Patent Application No. EP560268, published Sep. 15, 193, which is incorporated herein by reference;

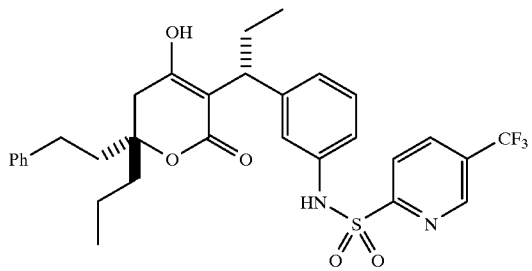

(i.e., U-140690) and related compounds disclosed in PCT Patent Application No. WO 9530670, published No. 16, 1995, which is incorporated herein by reference.

In a most preferred combination, a compound of this invention is administered in combination with ritonavir. Such a combination is especially useful for inhibiting HIV protease in a human. Such a combination is also especially useful for inhibiting or treating an HIV infection in a human. When used in such a combination the compound of this invention and ritonavir can be administered as separate agents at the same or different times or they can be formulated as a single composition comprising both compounds.

In a second most preferred combination, a compound of this invention is administered in a triple combination regimen, for example, with a second HIV protease inhibitor and a reverse transcriptase inhibitor or with two reverse transcriptase inhibitors. Triple combination therapy is especially useful for inhibiting or treating an HIV infection in humans. For example, triple combination therapy using two reverse transcriptase inhibitors (AZT and 3TC), in combination with an HIV protease inhibitor (ritonavir) was shown to significantly reduce plasma viremia in patients having symptoms of acute infection. (Markowitz, M., et al, Program Supplement, Abstract Th.B.930 entitled "Triple Therapy with AZT, 3TC, and Ritonavir in 12 Subjects Newly Infected with HIV-1", XI International Conference on AIDS, Vancouver, Jul. 7–12, 1996). A regimen of triple combination therapy using AZT and 3TC in combination with the HIV protease inhibitor indinavir also proved to be safe and well tolerated in humans, with potent antiretroviral activity and CD4 cell increases sustained for at least 24 weeks. (See Gulick, R., et al., Abstract LB7 entitled "Potent and Sustained Antiretroviral Acitivty of Indinavir in Combination with Zidovudine and Lamivudine", 3rd Conference on Retroviruses and Opportunistic Infections, Washington, D.C., Jan. 28–Feb. 1, 1996).

When triple combination therapy is administered, for example, using a compound of this invention in combination with two other compounds, those compounds may be selected from any of the group of protease inhibitors and/or reverse transcriptase inhibitors described above. A preferred HIV protease inhibitor (i.e. as second protease inhibitor) is selected from the group consisting of ritonavir, saquinavir, indinavir, nelfinavir, VX-478 and U-140690. A most preferred second HIV protease inhibitor is ritonavir. Preferred reverse transcriptase inhibitors include both nucleoside reverse transcriptase inhibitors such as zidovudine, didanosine, zalcitabine, stavudine, lamivudine, PMEa and bis-POMPMEA and non-nucleoside reverse transcriptase inhibitors such as nevirapine, delavirdine, UC-781, trovirdine, loviride, HEPT compounds and TSAO. A most preferred reverse transcriptase inhibitor in triple combination therapy is lamivudine. When used in such a combination, the compound of this invention and the other two compounds can be administered as separate agents at the same or different times or they can be formulated as a single compound comprising all three compounds.

When administered in combination with a compound of this invention, ritonavir causes an improvement in the pharmacokinetics (i.e., increases half-life, increases the time to peak plasma concentration, increases blood levels) of the compound of this invention.

Preferred dosage forms for ritonavir include (a) a liquid dosage form for oral administration as disclosed in U.S. Pat. No. 5,484,801, issued Jan. 19, 1996, which is incorporated herein by reference, (b) an encapsulated solid or semi-solid dosage form as disclosed in PCT Patent Application No. WO95/07696, published Mar. 23, 1995 and U.S. Ser. No. 08/402,690, filed Mar. 13, 1995, both of which are incorporated herein by reference and (c) an encapsulated solid dosage form as disclosed in PCT Patent Application No.

WO95/09614, published Apr. 13, 1995, which is incorporated herein by reference.

Total daily dose of ritonavir (administered in combination with a compound of this invention) to be administered to a human or other mammal host in single or divided doses may be in amounts, for example, from 0.001 to 300 mg/kg body weight daily and more usually 0.1 to 10 mg of ritonavir. Dosage unit compositions may contain such amounts of submultiples thereof to make up the daily dose.

It will be understood that agents which can be combined with the compound of the present invention for the inhibition, treatment or prophylaxis of AIDS or an HIV infection are not limited to those listed above, but include in principle any agents useful for the treatment or prophylaxis of AIDS or an HIV infection.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula I:

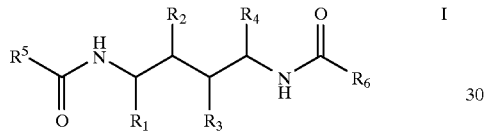

or a pharmaceutically acceptable salt, ester or prodrug thereof wherein $R_1$ and $R_4$ are independently selected from the group consisting of $C_1$-to-$C_6$-loweralkyl, $C_3$-to-$C_8$-cycloalkyl-$C_1$-to-$C_6$-alkyl and aryl-$C_1$-to-$C_6$-alkyl;

$R_2$ is —H and $R_3$ is —OH or $R_2$ is —OH and $R_3$ is —H;

one of $R_5$ and $R_6$ is —$L_1L_2$ wherein $L_1$ is —O— or —$NR_{101}$— wherein $R_{101}$ is hydrogen or $C_1$-to-$C_6$-loweralkyl and $L_2$ is -bis-tetrahydrofuran which is unsubstituted or substituted with $C_1$-to-$C_6$-loweralkyl or $C_3$-to-$C_8$-cycloalkyl; and the other of $R_5$ and $R_6$ is 1) —$L_1L_2$ wherein $L_1$ and $L_2$ are independently as defined above, 2) —$L_3L_4R_7$ wherein
$L_3$ is $C_1$-to-$C_{10}$-alkylenyl-, $C_2$-to-$C_{10}$-alkenylenyl- or —$OCH_2$;
$L_4$ is absent or is selected from the group consisting of —O—, —S—, —S(O)—, —S(O)$_2$—, and —N($R_8$)— wherein
$R_8$ is —H, $C_1$-to-$C_6$-loweralkyl, $C_3$-to-$C_8$-cycloalkyl or
$C_3$-to-$C_8$-cycloalkyl-$C_1$-to-$C_6$-alkyl; and
$R_7$ is aryl or a heterocycle selected from the group consisting of i) pyridyl, ii) pyrimidinyl, iii) benzimidazolyl, iv) benzoxazolyl, v) benzimidazolinone and vi) thiazolyl wherein the heterocycle is unsubstituted or substituted with one, two or three substituents independently selected from the group consisting of aa) $C_1$-to-$C_6$-loweralkyl, bb) hydroxy, cc) amino, and dd) halogen, or 3) aryl with the proviso that when $R_5$ is —O-bis-tetrahydrofuran, $R_6$ is other than —O-bis-tetrahydrofuran.

2. A compound according to claim 1 wherein
$R_1$ and $R_4$ are independently selected from the group consisting of (i) benzyl unsubstituted or substituted with one, two or three of —OH or —$C_1$-$C_3$-alkoxy and (ii) —$C_5$-$C_7$-cycloalkylmethyl unsubstituted or substituted with one, two or three of —OH or —$C_1$-$C_3$-alkoxy, and $R_2$, $R_3$, $R_5$, and $R_6$ are as defined therein.

3. A compound according to claim 2 wherein $R_1$ and $R_4$ are unsubstituted benzyl and $R_2$, $R_3$, $R_5$, and $R_6$ are as defined therein.

4. A compound according to claim 3 wherein
$R_1$ and $R_4$ are as defined therein;
$R_2$ and $R_3$ are as defined therein;
one of $R_5$ and $R_6$ is —$L_1L_2$ wherein $L_1$ is —O— and $L_2$ is -bis-tetrahydrofuran; and
the other of $R_5$ and $R_6$ is —$L_3L_4R_7$(C) wherein $L_3$ is $C_1$-to-$C_{10}$-alkylenyl-, $L_4$ is —O—, and $R_7$ is
a) phenyl substituted with one to five substituents independently selected from the group consisting of i) $C_1$-to-$C_6$-loweralkyl, ii) hydroxy, iii) amino, iv) hydroxy-$C_1$-to-$C_6$-alkyl, and v) halogen or
b) a heterocycle selected from the group consisting of i) pyridyl, ii) pyrimidinyl, iii) benzimidazolyl, iv) benzoxazolyl, v) benzimidazolinone and vi) thiazolyl wherein the heterocycle is unsubstituted or substituted with one, two or three substituents independently selected from the group consisting of aa) $C_1$-to-$C_6$-loweralkyl, bb) hydroxy, cc) amino, and dd) halogen.

5. A compound according to claim 4 wherein
$R_1$ and $R_4$ are as defined therein;
$R_2$ and $R_3$ are as defined therein;
one of $R_5$ and $R_6$ is —$L_1L_2$ wherein —$L_1L_2$ is as defined therein; and
the other of $R_5$ and $R_6$ is —$L_3L_4R_7$(C) wherein $L_3$ is $C_1$-to-$C_{10}$-alkylenyl-, $L_4$ is —O— and $R_7$ is
a) phenyl substituted with one or two substituents independently selected from the group consisting of methyl, ethyl and propyl and optionally further substituted with $C_1$-to-$C_6$-loweralkyl, amino, halogen, hydroxy or hydroxymethyl or
b) a heterocycle selected from the group consisting of i) pyridyl, ii) pyrimidinyl, iii) benzimidazolyl, iv) benzoxazolyl,v) benzimidazolinone and vi) thiazolyl wherein the heterocycle is unsubstituted or substituted with two methyl substituents and optionally with a third substituent selected from the group consisting of aa) $C_1$-to-$C_6$-loweralkyl, bb) hydroxy, cc) amino, and dd) halogen.

6. A compound selected from the group consisting of:
(2S,3S,5S)-5-(2,6-Dimethyl-4-amino-phenoxyacetyl) amino-2-((3R,3aS,6aR)-bis-tetrahydrofuran-3-yl-oxycarbonyl)amino-1,6-diphenyl-3-hydroxyhexane;
(2S,3S,5S)-5-(2,6-Dimethyl-4-amino-phenoxyacetyl) amino-2-((3S,3aR,6aS)-bis-tetrahydrofuran-3-yl-oxycarbonyl)amino-1,6-diphenyl-3-hydroxyhexane;
(2S,3S,5S)-2-(2,6-Dimethyl-4-amino-phenoxyacetyl) amino-5-((3R,3aS,6aR)-bis-tetrahydrofuran-3-yl-oxycarbonyl)amino-1,6-diphenyl-3-hydroxyhexane;
(2S,3S,5S)-5-(2,4,6-Trimethyl-3-amino-phenoxyacetyl) amino-2-((3R,3aS,6aR)-bis-tetrahydrofuran-3-yl-oxycarbonyl)amino-1,6-diphenyl-3-hydroxyhexane;
(2S,3S,5S)-5-(2,6-Dimethyl-phenoxyacetyl)amino-2-((3R,3aS,6aR)-bis-tetrahydrofuran-3-yl-oxycarbonyl) amino-1,6-diphenyl-3-hydroxyhexane;

(2S,3S,5S)-2-(2,6-Dimethyl-phenoxyacetyl)amino-5-((3R,3aS,6aR)-bis-tetrahydrofuran-3-yl-oxycarbonyl)amino-1,6-diphenyl-3-hydroxyhexane;

(2S,3S,5S)-5-(2-Hydroxymethyl-6-methyl-phenoxyacetyl)amino-2-((3R,3aS,6aR)-bis-tetrahydrofuran-3-yl-oxycarbonyl)amino-1,6-diphenyl-3-hydroxyhexane;

(2S,3S,5S)-5-(4,6-Dimethyl-pyrimidinyl-5-oxyacetyl)amino-2-((3R,3aS,6aR)-bis-tetrahydrofuran-3-yl-oxycarbonyl)amino-1,6-diphenyl-3-hydroxyhexane;

(2S,3S,5S)-5-(N-(2,6-Dimethyl-phenyl)aminoacetyl)amino-2-((3R,3aS,6aR)-bis-tetrahydrofuran-3-yl-oxycarbonyl)amino-1,6-diphenyl-3-hydroxyhexane;

(2S,3S,5S)-5-(2,6-Dimethyl-pyridin-3-yl-oxyacetyl)amino-2-((3R,3aS,6aR)-bis-tetrahydrofuran-3-yl-oxycarbonyl)amino-1,6-diphenyl-3-hydroxyhexane;

(2S,3S,5S)-5-(2,4,6-Trimethyl-phenoxyacetyl)amino-2-((3R,3aS,6aR)-bis-tetrahydrofuran-3-yl-oxycarbonyl)amino-1,6-diphenyl-3-hydroxyhexane;

(2S,3S,5S)-5-(2-Methoxy-6-methylphenoxyacetyl)amino-2-((3R,3aS,6aR)-bis-tetrahydrofuran-3-yl-oxycarbonyl)amino-1,6-diphenyl-3-hydroxyhexane;

(2S,3S,5S)-5-(N-(2,6-Dimethyl-phenyl)-N-methyl-aminoacetyl)amino-2-((3R,3aS,6aR)-bis-tetrahydrofuran-3-yl-oxycarbonyl)amino-1,6-diphenyl-3-hydroxyhexane;

(2S,3S,5S)-5-(2,6-Dimethyl-4-fluoro-phenoxyacetyl)amino-2-((3R,3aS,6aR)-bis-tetrahydrofuran-3-yl-oxycarbonyl)amino-1,6-diphenyl-3-hydroxyhexane;

(2S,3S,5S)-5-(2,6-Dimethyl-4-fluoro-phenoxyacetyl)amino-2-((3R,3aS,6aR)-bis-tetrahydrofuran-3-yl-oxycarbonyl)amino-1,6-diphenyl-3-hydroxyhexane;

(2S,3S,5S)-5-(2,6-Dimethyl-3-amino-phenoxyacetyl)amino-2-((3R,3aS,6aR)-bis-tetrahydrofuran-3-yl-oxycarbonyl)amino-1,6-diphenyl-3-hydroxyhexane;

(2S,3S,5S)-5-(2,6-Dimethyl-4-aminoacetyl)amino-2-((3R,3aS,6aR)-bis-tetrahydrofuran-3-yl-oxycarbonyl)amino-1,6-diphenyl-3-hydroxyhexane;

(2S,3S,5S)-5-(2,6-Dimethyl-4-amino-phensulfonylacetyl)amino-2-((3R,3aS,6aR)-bis-tetrahydrofuran-3-yl-oxycarbonyl)amino-1,6-diphenyl-3-hydroxyhexane;

(2S,3S,5S)-5-(2,6-Dimethyl-4-amino-phenylsulfinylacetyl)amino-2-((3R,3aS,6aR)-bis-tetrahydrofuran-3-yl-oxycarbonyl)amino-1,6-diphenyl-3-hydroxyhexane;

(2S,3S,5S)-5-(4,6-Dimethyl-benzimidazol-5-yloxy-acetyl)amino-2-((3R,3aS,6aR)-bis-tetrahydrofuran-3-yl-oxycarbonyl)amino-1,6-diphenyl-3-hydroxyhexane;

(2S,3S,5S)-5-(4,6-Dimethyl-benzimidazolinon-5-yloxy-acetyl)amino-2-((3R,3aS,6aR)-bis-tetrahydrofuran-3-yl-oxycarbonyl)amino-1,6-diphenyl-3-hydroxyhexane;

(2S,3S,5S)-5-(4,6-Dimethyl-benzoxazol-5-yloxy-acetyl)amino-2-((3R,3aS,6aR)-bis-tetrahydrofuran-3-yl-oxycarbonyl)amino-1,6-diphenyl-3-hydroxyhexane;

(2S,3S,5S)-2-((5-Thiazolyl)methoxycarbonyl)amino-5-((3R,3aS,6aR), (3S,3-aR,6aS)-bis-tetrahydrofuran-3-yl-oxycarbonyl)amino-1,6-diphenyl-3-hydroxyhexane;

(2S,3S,5S)-2-((5-Thiazolyl)methoxycarbonyl)amino-5-((3S,3aR,6aS)-bis-tetrahydrofuran-3-yl-oxycarbonyl)amino-1,6-diphenyl-3-hydroxyhexane;

(2S,3S,5S)-5-((5-Thiazolyl)methoxycarbonyl)amino-2-((3R,3aS,6aR), (3S,3-aR,6aS)-bis-tetrahydrofuran-3-yl-oxycarbonyl)amino-1,6-diphenyl-3-hydroxyhexane;

(2S,3S,5S)-5-(4-Hydroxy-benzoyl)amino-2-((3S,3aR,6aS)-bis-tetrahydrofuran-3-yl-oxycarbonyl)amino-1,6-diphenyl-3-hydroxyhexane;

(2S,3S,5S)-5-(4-Acetoxy-benzoyl)amino-2-((3S,3aS,6aR)-bis-tetrahydrofuran-3-yl-oxycarbonyl)amino-1,6-diphenyl-3-hydroxyhexane;

(2S,3S,5S)-5-(4-Hydroxy-benzoyl)amino-2-((3R,3aS,6aR)-bis-tetrahydrofuran-3-yl-oxycarbonyl)amino-1,6-diphenyl-3-hydroxyhexane;

(2S,3S,5S)-5-(4-Acetoxy-benzoyl)amino-2-((3S,3aR,6aS)-bis-tetrahydrofuran-3-yl-oxycarbonyl)amino-1,6-diphenyl-3-hydroxyhexane;

(2S,3S,5S)-5-(2-Chloro-4-hydroxy-benzoyl)amino-2-((3R,3aS,6aR)-bis-tetrahydrofuran-3-yl-oxycarbonyl)amino-1,6-diphenyl-3-hydroxyhexane;

(2S,3S,5S)-5-(3-Hydroxy-benzoyl)amino-2-((3S,3aR,6aS)-bis-tetrahydrofuran-3-yl-oxycarbonyl)amino-1,6-diphenyl-3-hydroxyhexane;

(2S,3S,5S)-2-(3-Hydroxy-2-methyl-benzoyl)amino-5-((3R,3aS,6aR)-bis-tetrahydrofuran-3-yl-oxycarbonyl)amino-1,6-diphenyl-3-hydroxyhexane;

(2S,3S,5S)-2-(3-Hydroxy-2-methyl-benzoyl)amino-5-((3S,3aR,6aS)-bis-tetrahydrofuran-3-yl-oxycarbonyl)amino-1,6-diphenyl-3-hydroxyhexane;

(2S,3S,5S)-2-(3-Amino-2-methyl-benzoyl)amino-5-((3R,3aS,6aR)-bis-tetrahydrofuran-3-yl-oxycarbonyl)amino-1,6-diphenyl-3-hydroxyhexane;

(2S,3S,5S)-2-(3-Amino-6-chloro-benzoyl)amino-5-((3R,3aS,6aR)-bis-tetrahydrofuran-3-yl-oxycarbonyl)amino-1,6-diphenyl-3-hydroxyhexane;

(2S,3S,5S)-2-(3-Amino-6-chloro-benzoyl)amino-5-((3S,3aR,6aS)-bis-tetrahydrofuran-3-yl-oxycarbonyl)amino-1,6-diphenyl-3-hydroxyhexane;

(2S,3S,5S)-2-(4-Hydroxy-benzoyl)amino-5-((3R,3aS,6aR)-bis-tetrahydrofuran-3-yl-oxycarbonyl)amino-1,6-diphenyl-3-hydroxyhexane;

(2S,3S,5S)-2-(4-Hydroxy-benzoyl)amino-5-((3S,3aR,6aS)-bis-tetrahydrofuran-3-yl-oxycarbonyl)amino-1,6-diphenyl-3-hydroxyhexane;

(2S,3S,5S)-2-(3-Hydroxy-benzoyl)amino-5-((3R,3aS,6aR)-bis-tetrahydrofuran-3-yl-oxycarbonyl)amino-1,6-diphenyl-3-hydroxyhexane;

(2S,3S,5S)-2-(3-Hydroxy-benzoyl)amino-5-((3S,3aR,6aS)-bis-tetrahydrourayn-3-yl-oxycarbonyl)amino-1,6-diphenyl-3-hydroxyhexane;

(2S,3S,5S)-2-(Benzoyl)amino-5-((3R,3aS,6aR)-bis-tetrahydrofuran-3-yl-oxycarbonyl)amino-1,6-diphenyl-3-hydroxyhexane;

(2S,3S,5S)-2-(Benzoyl)amino-5-((3S,3 aR,6aS)-bis-tetrahydrofuran-3-yl-oxycarbonyl)amino-1,6-diphenyl-3-hydroxyhexane;

(2S,3S,5S)-2-(4-Acetoxy-benzoyl )amino-5-((3R,3aS,6aR)-bis-tetrahydrofuran-3-yl-oxycarbonyl)amino-1,6-diphenyl-3-hydroxyhexane;

(2S,3S,5S)-2-(4-Amino-2-chloro-benzoyl)amino-5-((3R,3aS,6aR)-bis-tetrahydrofuran-3-yl-oxycarbonyl)amino-1,6-diphenyl-3-hydroxyhexane;

(2S,3S,5S)-2-(4-Amino-2-chloro-benzoyl)amino-5-((3S,3aR,6aS)-bis-tetrahydrofuran-3-yl-oxycarbonyl)amino-1,6-diphenyl-3-hydroxyhexane;

(2S,3S,5S)-2-(3-Methoxy-4-hydroxy-benzoyl)amino-5-((3R,3aS,6aR)-bis-tetrahydrofuran-3-yl-oxycarbonyl)amino-1,6-diphenyl-3-hydroxyhexane; and (2S,3S,5S)-5-(2,6-Dimethyl-3-hydroxy-phenoxyacetyl)amino-2-((3R,3aS,6aR)-bis-tetrahydrofuran-3-yl-oxycarbonyl)amino-1,6-diphenyl-3-hydroxyhexane;

or a pharmaceutically acceptable salt, ester or prodrug thereof.

7. A compound selected from the group consisting of (2S,3S,5S)-5-(2,6-Dimethyl-3-amino-phenoxyacetyl)amino-2-((3R, 3aS,6aR)-bis-tetrahydrofuran-3-yl-oxycarbonyl)amino-1,6-diphenyl-3-hydroxyhexane and (2S,3S,5S)-5-(2,6-Dimethyl-3-hydroxy-phenoxyacetyl)amino-2-((3R, 3aS,6aR)-bis-tetrahydrofuran-3-yl-oxycarbonyl)amino-1,6-diphenyl-3-hydroxyhexane or a pharmaceutically acceptable salt, ester or prodrug thereof.

8. A pharmaceutical composition for inhibiting HIV protease comprising a pharmaceutical carrier and a therapeutically effective amount of the compound of claim 1.

9. A pharmaceutical composition for inhibiting HIV protease comprising a pharmaceutical carrier and a therapeutically effective amount of the compound of claim 7.

10. A method for inhibiting HIV protease comprising administering to a human in need of such treatment a therapeutically effective amount of the compound of claim 1.

11. A method for inhibiting HIV protease comprising administering to a human in need of such treatment a therapeutically effective amount of the compound of claim 7.

12. A method for inhibiting an HIV infection comprising administering to a human in need of such treatment a therapeutically effective amount of the compound of claim 1.

13. A method for inhibiting an HIV infection comprising administering to a human in need of such treatment a therapeutically effective amount of the compound of claim 7.

* * * * *

UNITED STATES PATENT AND TRADEMARK OFFICE
CERTIFICATE OF CORRECTION

PATENT : 5,905,068
DATED : May 18, 1999
INVENTOR(S): Xiaoqi Chen et al.

It is certified that error appears in the above-identified patent and that said Letters Patent is hereby corrected as shown below:

Col. 69, line 60
  replace "(3S,3-aR,6aS)"
  with --(3S,3aR,6aS)--.

Col. 69, line 66
  replace "(3S,3-aR,6aS)"
  with --(3S,3aR,6aS)--.

Col. 70, line 7
  replace "((3R ,3aS,6aR)"
  with --((3R,3aS,6aR)--.

Col. 70, line 49
  replace "tetrahydrourayn"
  with --tetrahydrofuran--.

Col. 70, line 55
  replace "((3S,3 aR,6aS)"
  with --((3S,3aR,6aS)--.

Col. 71, line 11
  replace "((3R, 3aS,6aR)"
  with --((3R,3aS,6aR)--.

Col. 71, line 15
  replace "((3R, 3aS,6aR)"
  with --((3R,3aS,6aR)--.

Signed and Sealed this

Third Day of April, 2001

Attest:

NICHOLAS P. GODICI

Attesting Officer

Acting Director of the United States Patent and Trademark Office